United States Patent
Chen et al.

(10) Patent No.: US 12,263,234 B2
(45) Date of Patent: *Apr. 1, 2025

(54) ANTI-PD-L1 DIABODIES AND THE USE THEREOF

(71) Applicant: Tayu Huaxia Biotech Medical Group Co., Ltd., Beijing (CN)

(72) Inventors: Lieping Chen, Beijing (CN); Zhenguo Wen, Beijing (CN); Liqun Luo, Beijing (CN); Qianyong Liu, Beijing (CN)

(73) Assignee: Tayu Huaxia Biotech Medical Group Co., Ltd., Beijing (CN)

( * ) Notice: Subject to any disclaimer, the term of this patent is extended or adjusted under 35 U.S.C. 154(b) by 861 days.

This patent is subject to a terminal disclaimer.

(21) Appl. No.: 17/425,296

(22) PCT Filed: Jan. 17, 2020

(86) PCT No.: PCT/CN2020/072572
§ 371 (c)(1),
(2) Date: Jul. 22, 2021

(87) PCT Pub. No.: WO2020/151572
PCT Pub. Date: Jul. 30, 2020

(65) Prior Publication Data
US 2022/0088232 A1 Mar. 24, 2022

(51) Int. Cl.
*A61K 51/10* (2006.01)
*A61K 39/00* (2006.01)
*C07K 16/28* (2006.01)

(52) U.S. Cl.
CPC ...... *A61K 51/1093* (2013.01); *C07K 16/2827* (2013.01); *A61K 2039/505* (2013.01); *C07K 2317/56* (2013.01); *C07K 2317/622* (2013.01); *C07K 2317/626* (2013.01); *C07K 2317/92* (2013.01)

(58) Field of Classification Search
CPC .......... A61K 51/1093; A61K 2039/505; C07K 16/2827; C07K 2317/56; C07K 2317/622; C07K 2317/626; C07K 2317/92
See application file for complete search history.

(56) References Cited

U.S. PATENT DOCUMENTS

| | | |
|---|---|---|
| 4,816,567 A | 3/1989 | Cabilly |
| 5,500,362 A | 3/1996 | Robinson |
| 5,591,828 A | 1/1997 | Bosslet |
| 5,624,821 A | 4/1997 | Winter |
| 5,648,260 A | 7/1997 | Winter |
| 5,750,373 A | 5/1998 | Garrard |
| 5,753,206 A | 5/1998 | Mcbride et al. |
| 5,770,429 A | 6/1998 | Lonberg et al. |
| 5,821,333 A | 10/1998 | Carter |
| 5,821,337 A | 10/1998 | Carter |
| 6,075,181 A | 6/2000 | Kucherlapati |
| 6,150,584 A | 11/2000 | Kucherlapati |
| 6,194,551 B1 | 2/2001 | Idusogie |
| 6,602,684 B1 | 8/2003 | Umana |
| 6,737,056 B1 | 5/2004 | Presta |
| 6,953,567 B2 | 10/2005 | Griffiths |
| 6,982,321 B2 | 1/2006 | Winter |
| 7,041,870 B2 | 5/2006 | Tomizuka |
| 7,087,409 B2 | 8/2006 | Barbas, III |
| 7,189,826 B2 | 3/2007 | Rodman |
| 7,332,581 B2 | 2/2008 | Presta |
| 7,371,849 B2 | 5/2008 | Honda |
| 7,521,541 B2 | 4/2009 | Eigenbrot |
| 7,527,791 B2 | 5/2009 | Adams |
| 7,642,228 B2 | 1/2010 | Carter |
| 8,313,913 B2 | 11/2012 | Nakamura |
| 8,679,491 B2 | 3/2014 | Hanai |
| 8,754,287 B2 | 6/2014 | Macdonald |
| 8,945,862 B2 | 2/2015 | Wu et al. |
| 9,884,131 B2 | 2/2018 | Kjaer et al. |
| 10,465,007 B2 | 11/2019 | Chen et al. |
| 11,987,629 B2* | 5/2024 | Chen ........................ A61K 9/19 |
| 12,060,425 B2* | 8/2024 | Wu ..................... C07K 16/2803 |
| 2002/0164328 A1 | 11/2002 | Shinkawa |
| 2003/0115614 A1 | 6/2003 | Kanda |
| 2003/0157108 A1 | 8/2003 | Presta |
| 2004/0093621 A1 | 5/2004 | Shitara |
| 2004/0109865 A1 | 6/2004 | Niwa |
| 2004/0110282 A1 | 6/2004 | Kanda |

(Continued)

FOREIGN PATENT DOCUMENTS

| | | |
|---|---|---|
| CN | 1315967 A | 10/2001 |
| CN | 1905900 A | 1/2007 |

(Continued)

OTHER PUBLICATIONS

Winkler et al. (Journal of Immunology (2000) 165(8): 4505-4514) (Year: 2000).*
Edwards et al. (Journal of Molecular Biology (2003) 334(1):103-118) (Year: 2003).*
Lloyd et al. (Protein Engineering, Design and Selection (2009) 22(3): 159-168) (Year: 2009).*
Schroeder and Cavacini (Journal of Allergy and Clinical Immunology (2010) 125(2, Suppl.2): S41-S52) (Year: 2010).*
Sela-Culang et al. (Frontiers in Immunology (2013) 4: 302) (Year: 2013).*
Forsström et al. (PLoS One (2015) 10(3): e0121673) (Year: 2015).*
Kwon et al. (Methods (2019) 154: 136-142) (Year: 2019).*
Chen et al. U.S. Appl. No. 15/733,835. Compositions and Methods for Imaging. (Year: 2020).*
Abhinandan, K.R. et al. (Aug. 2008, e-pub. Jul. 9, 2008). "Analysis and Improvements To Kabat and Structurally Correct Numbering Of Antibody Variable Domain," Molecular Immunology 45(14):3832-3839.

(Continued)

*Primary Examiner* — Brad Duffy
*Assistant Examiner* — Elizabeth A Shupe
(74) *Attorney, Agent, or Firm* — MORRISON & FOERSTER LLP

(57) ABSTRACT

Provided are anti-PD-L1 diabodies, imaging agents, methods and kits for determination of the distribution and expression levels of PD-L1 in an individual having a disease or condition. Anti-PD-L1 diabody agents, and methods for treating diseases or disorders are also provided.

24 Claims, 8 Drawing Sheets

Specification includes a Sequence Listing.

(56) References Cited

U.S. PATENT DOCUMENTS

| | | |
|---|---|---|
| 2004/0110704 A1 | 6/2004 | Yamane |
| 2004/0132140 A1 | 7/2004 | Satoh |
| 2005/0014934 A1 | 1/2005 | Hinton |
| 2005/0031613 A1 | 2/2005 | Nakamura |
| 2005/0079574 A1 | 4/2005 | Bond |
| 2005/0119455 A1 | 6/2005 | Fuh |
| 2005/0123546 A1 | 6/2005 | Umana |
| 2005/0216958 A1 | 9/2005 | Yamane et al. |
| 2005/0266000 A1 | 12/2005 | Bond |
| 2006/0270045 A1 | 11/2006 | Cregg |
| 2007/0061900 A1 | 3/2007 | Murphy |
| 2007/0117126 A1 | 5/2007 | Sidhu |
| 2007/0134759 A1 | 6/2007 | Nishiya |
| 2007/0160598 A1 | 7/2007 | Dennis |
| 2007/0237764 A1 | 10/2007 | Birtalan |
| 2007/0292936 A1 | 12/2007 | Barthelemy |
| 2008/0241884 A1 | 10/2008 | Shitara |
| 2009/0002360 A1 | 1/2009 | Chen |
| 2009/0307787 A1 | 12/2009 | Grosveld |
| 2010/0122358 A1 | 5/2010 | Brueggemann |
| 2010/0329977 A1 | 12/2010 | Hengerer et al. |
| 2011/0287009 A1 | 11/2011 | Scheer |
| 2015/0289489 A1 | 10/2015 | Macdonald |
| 2015/0346208 A1 | 12/2015 | Couto |
| 2016/0009805 A1* | 1/2016 | Kowanetz ........ C07K 14/70532 530/391.1 |
| 2016/0052990 A1 | 2/2016 | Ring et al. |
| 2016/0331852 A1 | 11/2016 | Zeglis |
| 2017/0157265 A1 | 6/2017 | Junutula et al. |
| 2017/0218066 A1 | 8/2017 | Zhou |
| 2018/0071413 A1 | 3/2018 | Olive |
| 2018/0305464 A1 | 10/2018 | Li et al. |
| 2019/0077867 A1 | 3/2019 | Zhu et al. |
| 2019/0144543 A1 | 5/2019 | Chen et al. |
| 2019/0330348 A1* | 10/2019 | Qian ................. C07K 16/2863 |
| 2020/0115454 A1 | 4/2020 | Chen et al. |
| 2020/0407447 A1* | 12/2020 | Nicosia ................. A61P 35/00 |
| 2021/0213145 A1 | 7/2021 | Chen et al. |
| 2021/0214444 A1 | 7/2021 | Chen et al. |
| 2021/0261665 A1 | 8/2021 | Chen et al. |
| 2021/0309745 A1 | 10/2021 | Chen et al. |

FOREIGN PATENT DOCUMENTS

| | | |
|---|---|---|
| CN | 101927007 A | 12/2010 |
| CN | 106459200 A | 2/2017 |
| CN | 107847574 A | 3/2018 |
| CN | 107921131 A | 4/2018 |
| CN | 107922503 A | 4/2018 |
| EP | 0404097 A2 | 12/1990 |
| EP | 3309177 A1 | 4/2018 |
| WO | 198704462 A1 | 7/1987 |
| WO | 199311161 A1 | 6/1993 |
| WO | 199429351 A2 | 12/1994 |
| WO | 199429351 A3 | 2/1995 |
| WO | 199704801 A1 | 2/1997 |
| WO | 199730087 A1 | 8/1997 |
| WO | 199858964 A1 | 12/1998 |
| WO | 199922764 A1 | 5/1999 |
| WO | 199951642 A1 | 10/1999 |
| WO | 200061739 A1 | 10/2000 |
| WO | 200129246 A1 | 4/2001 |
| WO | 2002031140 A1 | 4/2002 |
| WO | 2003011878 A2 | 2/2003 |
| WO | 2003048731 A2 | 6/2003 |
| WO | 2003084570 A1 | 10/2003 |
| WO | 2003085107 A1 | 10/2003 |
| WO | 2003011878 A3 | 11/2003 |
| WO | 2003048731 A3 | 1/2004 |
| WO | 2004049794 A2 | 6/2004 |
| WO | 2004056312 A2 | 7/2004 |
| WO | 2004049794 A3 | 12/2004 |
| WO | 2005035586 A1 | 4/2005 |
| WO | 2005035778 A1 | 4/2005 |
| WO | 2004056312 A3 | 5/2005 |
| WO | 2005053742 A1 | 6/2005 |
| WO | 2003085119 A1 | 8/2005 |
| WO | 2005100402 A1 | 10/2005 |
| WO | 2006029879 A2 | 3/2006 |
| WO | 2006029879 A3 | 9/2006 |
| WO | 2006121168 A1 | 11/2006 |
| WO | 2007005874 A2 | 1/2007 |
| WO | 2007005874 A3 | 7/2007 |
| WO | 2008077546 A1 | 7/2008 |
| WO | 2013055958 A1 | 4/2013 |
| WO | 2013173223 A1 | 11/2013 |
| WO | 2015048520 A1 | 4/2015 |
| WO | 2015143382 A1 | 9/2015 |
| WO | 2016079049 A1 | 5/2016 |
| WO | 2016086021 A1 | 6/2016 |
| WO | 2016089873 A1 | 6/2016 |
| WO | 2016130819 A2 | 8/2016 |
| WO | 2016149188 A1 | 9/2016 |
| WO | 2016162368 A1 | 10/2016 |
| WO | 2017019846 A1 | 2/2017 |
| WO | 2017020291 A1 | 2/2017 |
| WO | 2017020858 A1 | 2/2017 |
| WO | 2017034916 A1 | 3/2017 |
| WO | 2017059397 A1 | 4/2017 |
| WO | 2017079112 A1 | 5/2017 |
| WO | 2017118321 A1 | 7/2017 |
| WO | 2017134305 A1 | 8/2017 |
| WO | 2017148424 A1 | 9/2017 |
| WO | 2017161976 A1 | 9/2017 |
| WO | 2017210302 A1 | 12/2017 |
| WO | 2017210335 A1 | 12/2017 |
| WO | 2017215590 A1 | 12/2017 |
| WO | 2018017673 A1 | 1/2018 |
| WO | 2018054940 A1 | 3/2018 |
| WO | 2018080812 A1 | 5/2018 |
| WO | 2018102682 A1 | 6/2018 |
| WO | 2018133837 A1 | 7/2018 |
| WO | 2019227490 A1 | 12/2019 |
| WO | 2019228509 A1 | 12/2019 |
| WO | 2019228514 A1 | 12/2019 |
| WO | 2020015722 A1 | 1/2020 |
| WO | 2020019232 A1 | 1/2020 |

OTHER PUBLICATIONS

Adolf-Bryfogle, J. et al. (2015, e-pub. Nov. 11, 2014). "PyIgClassify: A Database of Antibody CDR Structural Classifications," Nucleic Acids Res. 43:D432-D438.

Al-Lazikani, B. et al. (1997). "Standard Conformations for the Canonical Structures of Immunoglobulins," J. Mol. Biol. 273:927-948.

Almagro, J. et al. (Jan. 1, 2008). "Humanization of Antibodies," Frontiers in Bioscience 13:1619-1633.

Baca, M. et al. (Apr. 18, 1997). "Antibody Humanization Using Monovalent Phage Display," J. Biol. Chem. 272(16):10678-10684.

Boerner, P. et al. (Jul. 1, 1991). "Production of Antigen-Specific Human Monoclonal Antibodies From in Vitro-Primed Human Splenocytes," J. Immunol. 147(1):86-95.

Brodeur, B.R. et al. (1987). "Mouse-Human Myeloma Partners for the Production of Heterohybridomas," Chapter 4 in Monoclonal Antibody Production Techniques and Applications, Marcel Dekker, Inc. New York, New York, pp. 51-63.

Brüggemann, M. et al. (Nov. 1, 1987). "Comparison of the Effector Functions of Human Immunoglobulins Using a Matched Set of Chimeric Antibodies," J. Exp. Med. 166:1351-1361.

Burton, D.R. (1985). "Immunoglobulin G: Functional Sites," Molec. Immunol. 22(3):161-206.

Burvenich, I.G.J. et al. (Mar. 8, 2018). "Receptor Occupancy Imaging Studies in Oncology Drug Development," The AAPS Journal 20(2):1-16.

Butte, M.J. et al. (Jul. 2007). "Programmed Death-1 Ligand 1 Interacts Specifically with the B7-1 Costimulatory Molecule to Inhibit T Cell Responses," Immunity 27:111-122, 12 pages.

Capel, P.J. et al. (Feb. 1994). "Heterogeneity of Human IgG Fc Receptors," Immunomethods 4(1):25-34.

(56) References Cited

OTHER PUBLICATIONS

Carter, P. et al. (May 1992). "Humanization of an Anti-p185HER2 Antibody for Human Cancer Therapy," Proc. Natl. Acad. Sci. USA 89:4285-4289.
Chen, L. et al. (2015, e-pub. Sep. 1, 2015). "Anti-PD-1/PD-L1 Therapy of Human Cancer: Past, Present, and Future," The Journal of Clinical Investigation 125(9)3384-3391.
Chen, W. et al. (Jan. 2010). "A Large Human Domain Antibody Library Combining Heavy and Light Chain CDR3 Diversity," Mol. Immunol. 47(4):912-921, 23 pages.
Chothia, C. et al. (Aug. 20, 1987). "Canonical Structures for the Hypervariable Regions of Immunoglobulins," J. Mol. Biol. 196(4):901-917.
Chowdhury, P.S. (2008). "Engineering Hot Spots for Affinity Enhancement of Antibodies," Methods Mol. Biol. 207:179-196.
Cierna, Z. et al. (Feb. 2016, e-pub. Nov. 23, 2015). "Prognostic Value of Programmed-Death-1 Receptor (PD-1) and Its Ligand 1 (PD-L1) In Testicular Germ Cell Tumors," Annals of Oncology 27(2):300-305.
Clackson, T. et al. (Aug. 15, 1991). "Making Antibody Fragments Using Phage Display Libraries," Nature 352:624-628.
Clynes, R. et al. (Jan. 1998). "Fc Receptors are Required in Passive and Active Immunity to Melanoma," Proc. Natl. Acad. Sci. U.S.A. 95:652-656.
Cole, S.P.C. et al. (1985). "The EBV-Hybridoma Technique and Its Applicaton to Human Lung Cancer," in Monoclonal Antibodies and Cancer Therapy, Alan R. Liss, p. 77-96.
Cragg, M.S. et al. (Apr. 1, 2004). "Antibody Specificity Controls In Vivo Effector Mechanisms Of Anti-CD20 Reagents," Blood 103(7):2738-2743.
Cragg, M.S. et al. (Feb. 1, 2003). "Complement-Mediated Lysis By Anti-CD20 Mab Correlates With Segregation Into Lipid Rafts," Blood 101(3):1045-1052.
Cunningham, B.C. et al. (Jun. 2, 1989). "High-Resolution Epitope Mapping of hGH-Receptor Interactions by Alanine-Scanning Mutagenesis," Science 244:1081-1085.
Dall'Acqua, W et al. (2005). "Antibody Humanization by Framework Shuffling," Methods 36:43-60.
Daëron, M. (1997). "Fc Receptor Biology," Ann. Rev. Immunol. 15:203-234.
De Haas, M. et al. (1995). "Fcγ Receptor of Phagocytes," J. Lab. Clin. Med. 126(4):330-341.
Dong, H. et al. (Dec. 1999). "B7-H1, A Third Member Of The B7 Family, Co-Stimulates T-Cell Proliferation and Interleukin-10 Secretion," Nature Med. 5(12):1365-1369.
Dong, H. et al. (2002). "Tumor-Associated B7-HI Promotes T-Cell Apoptosis: A Potential Mechanism Of Immune Evasion," Nature Medicine 8(8):793-800.
Dong, H. et al. (Mar. 2004). "B7-H1 Determines Accumulation and Deletion of Intrahepatic CD8+ T Lymphocytes," Immunity 20(3):327-336.
Du, Y. et al. (2018). "Liposomal Nanohybrid Cerasomes Targeted to PD-L1 Enable Dual-modality Imaging and Improve Antitumor Treatments," Cancer Letters 414:230-238.
Duncan, A.R. et al. (Apr. 21, 1988). "The Binding Site for C1q on IgG," Nature 322:738-740.
Edgar, R.C. (2004, e-pub. Mar. 19, 2004). "MUSCLE: Multiple Sequence Alignment With High Accuracy And High Throughput," Nucleic Acids Research 32(5):1792-1797.
Edgar, R.C. (Aug. 19, 2004). "Muscle: A Multiple Sequence Alignment Method With Reduced Time And Space Complexity," BMC Bioinformatics 5(113):1-19.
Ehrenmann, F. et al. (Jan. 2010, e-pub. Nov. 9, 2009). "IMGT/3Dstructure-DB and IMGT/DomainGapAlign: A Database and a Tool For Immunoglobulins or Antibodies, T Cell Receptors, MHC, IgSF and MhcSF," Nucleic Acids Res. 38:D301-D307.
Endo, Y. et al. (2003). "High-Throughput, Genome-Scale Protein Production Method Based On The Wheat Germ Cell-Free Expression System," Biotechnol. Adv. 21:695-713.

Extended European Search Report, dated Feb. 8, 2022, for European Patent Application No. 18927730.4, 17 pages.
Extended European Search Report, dated Feb. 9, 2022, for European Patent Application No. 19810897.9, 14 pages.
Fellouse, F.A. et al. (Aug. 24, 2004). "Synthetic Antibodies From a Four-Amino-Acid Code: A Dominant Role for Tyrosine in Antigen Recognition," Proc. Natl. Acad. Sci. USA 101(34):12467-12472.
Freeman, G.J. et al. (2000, e-pub. Oct. 2, 2000). "Engagement of the PD-1 Immunoinhibitory Receptor by a Novel B7 Family Member Leads to Negative Regulation of Lymphocyte Activation," J. Exp. Med. 192:1027-1034.
Gandini, S. et al. (Apr. 2016, e-pub. Feb. 10, 2016). "PD-L1 Expression In Cancer Patients Receiving Anti PD-1/PD-L1 Antibodies: A Systematic Review and Meta-Analysis," Critical Reviews In Oncology/Hematology 100:88-98.
Gazzano-Santoro, H. et al. (Mar. 28, 1997). "A Non-Radioactive Complement-Dependent Cytotoxicity Assay for Anti-CD20 Monoclonal Antibody," J. Immunol. Methods 202:163-171.
Goding, J.W. (1983). "Production of Monoclonal Antibodies," Chapter 3 in Monoclonal Antibodies: Principles and Practice, Academic Press, pp. 59-103.
Griffiths, A.D. et al. (1993). "Human Anti-Self Antibodies with High Specificity from Phage Display Libraries," EMBO J. 12(2):725-734.
Guyer, R.L. et al. (Aug. 1976). "Immunoglobulin Binding By Mouse Intestinal Epithelial Cell Receptors," J. Immunol. 117(2):587-593.
Hellstrom, I. et al. (Mar. 1985). "Strong Antitumor Activities of lgG3 Antibodies to a Human Melanoma-associated Ganglioside," Proc. Natl. Acad. Sci. USA 82:1499-1502.
Hellstrom, I. et al. (Sep. 1986). "Antitumor Effects of L6, an IgG2a Antibody That Reacts With Most Human Carcinomas," Proc. Natl. Acad. Sci. USA 83:7059-7063.
Hettich, M. et al. (Jun. 18, 2016). "High-Resolution PET Imaging With Therapeutic Antibody-Based PD-1/PD-L1 Checkpoint Tracers," Theranostics 6(10):1629-1640.
Hirano, F. et al. (Feb. 1, 2005). "Blockade of B7-H1 and PD-1 By Monoclonal Antibodies Potentiates Cancer Therapeutic Immunity," Cancer Research 65(3):1089-1096.
Hollinger, P. et al. (Jul. 1993). "Diabodies: Small Bivalent And Bispecific Antibody Fragments," Proc. Natl. Acad. Sci. USA 90:6444-6448.
Honegger, A. et al. (2001). "Yet Another Numbering Scheme for Immunoglobulin Variable Domains: An Automatic Modeling and Analysis Tool," J Mol Biol. 309(3):657-670.
Hoogenboom, H.R. et al. (2001). "Overview of Antibody Phage-Display Technology and Its Applications," Chapter 1 in Methods in Molecular Biology, O'Brien et al. ed., Humana Press, Totowa, NJ, 178:1-37.
Hoogenboom, H.R. et al. (Sep. 20, 1992). "By-Passing Immunisation Human Antibodies From Synthetic Repertoires Of Germline VH Gene Segments Rearranged In Vitro," J. Mol. Biol. 227(2):381-388.
Idusogie, E.E. et al. (2000). "Mapping of the C1q Binding Site on Rituxan, a Chimeric Antibody With a Human IgG1 Fc," J. Immunol. 164:4178-4184.
International Preliminary Report on Patentability, issued Dec. 1, 2020, for PCT Application No. PCT/CN2018/089672, filed Jun. 1, 2018, 6 pages.
International Preliminary Report on Patentability, issued December 1. 2020, for PCT Application No. PCT/CN2019/08606, filed May 31, 2019, 5 pages.
International Preliminary Report on Patentability, issued December 1. 2020, for PCT Application No. PCT/CN2019/089571, filed May 31, 2019, 6 pages.
International Preliminary Report On Patentability, issued Jan. 26, 2021, for PCT Application No. PCT/CN2018/097175, filed Jul. 26, 2018, 7 pages.
International Preliminary Report on Patentability, issued Jul. 27, 2021, for PCT Application No. PCT/CN2020/072572, filed Jan. 17, 2020, 9 pages.

(56) References Cited

OTHER PUBLICATIONS

International Search Report and Written Opinion, mailed Feb. 25, 2019, for PCT Application No. PCT/CN2018/089672, filed Jun. 1, 2018, 14 pages.
International Search Report and Written, mailed Apr. 16, 2020, for PCT Application No. PCT/CN2020/072572, filed Jan. 17, 2020, 16 pages.
International Search Report and Written, mailed Aug. 27, 2019, for PCT Application No. PCT/CN2019/089571, filed May 31, 2019, 14 pages.
International Search Report and Written, mailed Sep. 10, 2019, for PCT Application No. PCT/CN2019/08606, filed May 31, 2019, 12 pages.
International Search Report, mailed Apr. 30, 2019, for PCT Application No. PCT/CN2018/09715, filed Jul. 26, 2018, 12 pages.
Ishida, Y. et al. (1992). "Induced Expression Of PD-1, A Novel Member Of The immunoglobulin Gene Superfamily, Upon Programmed Cell Death," EMBO J. 11(11):3887-3895.
Jones, P.T. et al. (May 29, 1986). "Replacing the Complementarity-Determining Regions in a Human Antibody With Those From a Mouse," Nature 321:522-525.
Kabat, E.A et al. (1991). Sequences of Proteins of Immunological Interest, 5th ed., Public Health Service, National Institutes of Health, Bethesda, MD. TOC, 21 pages.
Kabat, E.A. et al. (Oct. 10, 1977). "Unusual Distribution Of Amino Acids In Complementarity-Determining (Hypervariable) Segments Of Heavy and Light Chains Of Immunoglobulins and Their Possible Roles In Specificity Of Antibody-Combining Sites," J. Biol. Chem. 252(19):6609-6616.
Kanda, Y. et al. (Jul. 5, 2006, e-pub. Apr. 11, 2006). "Comparison of Cell Line for Stable Production of Fucose-Negative Antibodies with Enhanced ADCC," Biotechnol. Bioeng. 94(4):680-688.
Kashmiri, S.V. et al. (2005). "SDR grafting—A New Approach to Antibody Humanization," Methods 36:25-34.
Keir, M.E. et al. (2008, e-pub. Jan. 2, 2008). "PD-1 and Its Ligands in Tolerance and Immunity," Annu. Rev. Immunol. 26:677-704.
Kenanova, V. et al. (Jan. 1, 2010). "Chapter 27: Engineering of the Fc Region for Improved PK (FcRn Interaction)," Antibody Engineering pp. 411-430. Abstract Only.
Kenanova, V. et al. (Jan. 15, 2005). "Tailoring the Pharmacokinetics and Positron Emission Tomography Imaging Properties of Anti-Carcinoembryonic Antigen Single-Chain Fv-Fc Antibody Fragments," Cancer Research 65(2):622-631, 23 pages.
Kim, H.-Y. et al. (2018, e-pub. Mar. 12, 2018). "RAGE-Specific Single Chain Fv For PET Imaging of Pancreatic Cancer," PLoS ONE 13(3):e0192821, 14 pages.
Kim, J-K. et al. (1994). "Localization of the Site of the Murine IgGI Molecule That is Involved in Binding to the Murine Intestinal Fc Receptor," Eur. J. Immunol. 24:2429-2434.
Klimka, A. et al. (2000). "Human Anti-CD30 Recombinant Antibodies by Guided Phage Antibody Selection Using Cell Panning," Br. J. Cancer 83(2):252-260.
Kohler, G. et al. (Aug. 7, 1975) "Continuous Cultures Of Fused Cells Secreting Antibody Of Predefined Specificity," Nature 256:495-497.
Kozbor, D. (Dec. 1984). "A Human Hybrid Myeloma for Production of Human Monoclonal Antibodies," J. Immunol. 133(6):3001-3005.
Latchman, Y. et al. (Mar. 2001). "PD-L2 Is A Second Ligand For PD-1 and Inhibits T Cell Activation," Nature Immunol. 2(3):261-268.
Lee, C.V. et al. (2004). "Bivalent Antibody Phage Display Mimics Natural Immunoglobulin," .J. Immunol. Methods 284(1-2):119-132.
Lee, C.V. et al. (2004). "High-Affinity Human Antibodies From Phage-Displayed Synthetic Fab Libraries With A Single Framework Scaffold," J. Mol. Biol. 340:1073-1093.
Lefranc, M.-P. et al. (2015, e-pub. Nov. 5, 2014). "IMGT®, The International ImMunoGeneTics Information System® 25 Years On," Nucleic Acids Res. 43:D413-D422.
Lefranc, M.P. et al. (Jan. 2003). "IMGT Unique Numbering For Immunoglobulin And T Cell Receptor Variable Domains And Ig Superfamily V-Like Domains," Dev. Comp. Immunol. 27(1):55-77.
Li, D. et al. (Mar. 5, 2018). "Immuno-PET Imaging of 89Zr Labeled Anti-PD-L1 Domain Antibody," Mol. Pharmaceutics 15(4):1674-1681.
Li, J. et al. (Mar. 7, 2006). "Human Antibodies for Immunotherapy Development Generated via a Human B Cell Hybridoma Technology," Proc. Natl. Acad. Sci. USA 103(10):3557-3562.
Lonberg, N. (Sep. 2005). "Human Antibodies From Transgenic Animals," Nat. Biotech. 23(9):1117-1125.
Lonberg, N. et al. (2008, e-pub. Jul. 21, 2008). "Fully Human Antibodies From Transgenic Mouse and Phage Display Platforms," Curr. Opin. Immunol. 20:450-459.
MacCallum, R.M. et al. (1996). "Antibody-Antigen Interactions: Contact Analysis and Binding Site Topography," J. Mol. Biol. 262:732-745.
Maggi, A. et al. (Aug. 21, 2016). "Development of a Novel Antibody-Tetrazine Conjugate for Bioorthogonal Pretargeting," Organic & Biomolecular Chemistry 14(31):7544-7551.
Marks, J.D. et al. (1991). "By-Passing Immunization Human Antibodies from V-gene Libraries Displayed on Phage," J. Mol. Biol. 222:581-597.
Marks, J.D. et al. (2004) "Selection of Human Antibodies from Phage Display Libraries," Chapter 8 in Methods in Molecular Biology, Lo, B.K.C. (ed.), Humana Press Inc., Totowa, NJ, 248:161-176, 29 pages.
Marks, J.D. et al. (Jul. 1992). "By-Passing Immunization: Building High Affinity Human Antibodies by Chain Shuffling," Bio/Technology 10:779-783.
McCafferty, J. et al. (Dec. 6, 1990). "Phage Antibodies: Filamentous Phage Displaying Antibody Variable Domains," Nature 348:552-554.
Meyer, J.-P. et al. (2018). "Bioorthogonal Masking of Circulation Antibody-TCO Groups Using Tetrazine-Functionalized Dextran Polymers," Bioconjugate Chemistry 29(2):538-545, 17 pages.
Mordenti, J. et al. (1989). "The Use of Interspecies Scaling in Toxicokinetics," Chapter 4 in Toxicokinetics and New Drug Development, Yacobi A. ed et al.; Pergamon Press, New York, pp. 42-96.
Morrison, S.C. et al. (Nov. 1984). "Chimeric Human Antibody Molecules: Mouse Antigen-Binding Domains With Human Constant Region Domains," Proc. Natl. Acad. Sci. USA 81:6851-6855.
Munson, P.J. et al. (1980). "LIGAND: A Versatile Computerized Approach for Characterization of Ligand-Binding Systems," Anal. Biochem. 107:220-239.
Ni, J. (2006). "Research Progress and Future Perspectives in Antibodomics and Antibodomic Drugs," Xiandai Mianyixue 26(4):265-268.(Translation of the Abstract 3 pages.).
Nigam, S. et al. (May 1, 2018). "Development of High Affinity Engineered Antibody Fragments Targeting PD-L1 for immunoPET," J. Nucl. Med. 59(1): 1101, 3 pages, Abstract.
Nishimura, H. et al. (Jan. 12, 2001). "Autoimmune Dilated Cardiomyopathy In PD-1 Receptor-Deficient Mice," Science 291(5502):319-322.
Nishimura, H. et al. (Aug. 1999). "Development Of Lupus-Like Autoimmune Diseases By Disruption Of The PD-1 Gene Encoding An ITIM Motif-Carrying Immunoreceptor," Immunity 11(2):141-151.
Nishimura, H. et al. (May 2001). "PD-1: An Inhibitory Immunoreceptor Involved In Peripheral Tolerance," Trends In Immunology 22(5):265-268.
Okazaki, A. et al. (Mar. 5, 2004). "Fucose Depletion From Human IgG1 Oligosaccharide Enhances Binding Enthalpy And Association Rate Between IgG1 and FcγRIIIa," J. Mol. Biol. 336(5):1239-1249.
Okazaki, T, et al. (Dec. 2003, e-pub. Nov. 2, 2003). "Autoantibodies Against Cardiac Troponin I Are Responsible For Dilated Cardiomyopathy In PD-1-Deficient Mice," Nature Medicine 9(12):1477-1483.
Osbourn, J. et al. (2005). "From Rodent Regents to Human Therapeutics Using Antibody Guided Selection," Methods 36:61-68.
Padlan, E.D. (1991). "A Possible Procedure for Reducing the Immunogenicity of Antibody Variable Domains While Preserving Their Ligand-Binding Properties," Mol. Immunol. 28(4/5):489-498.

(56) References Cited

OTHER PUBLICATIONS

Park, J.-J. et al. (Aug. 2010). "B7-HI/CD80 Interaction is Required for the Induction and Maintenance of Peripheral T-2 cell Tolerance," Blood 116(8):1291-1298.

Petkova, S.B. et al. (2006, e-pub. Oct. 31, 2006). "Enhanced Half-Life of Genetically Engineered Human IgG1 Antibodies in a Humanized FcRn Mouse Model: Potential Application in Humorally Mediated Autoimmune Disease," Int'l. Immunol. 18(12):1759-1769.

Petroff, M.G. et ai. (Apr. 2002). "B7 Family Molecules: Novel Immunomodulators At The Maternal-Fetal Interface," Placenta 23(Suppl A):S95-S101.

Plückthun, A. (1992) "Mono- and Bivalent Antibody Fragments Produced in *Escherichia coli*: Engineering, Folding and Antigen Binding," Immunological Reviews No. 130:151-189.

Plückthun, A. (1994) "Antibodies from *Escherichia coli*," Chapter 11 in Handbook of Experimental Pharmacology 113:269-315.

Presta, L.G. (1992). "Antibody Engineering," Current Opinion in Structural Biology 2:593-596.

Presta, L.G. et al. (Sep. 1, 1993). "Humanization of an Antibody Directed Against IgE," J. Immunol. 151(5):2623-2632.

Queen, C. et al. (Dec. 1989). "A Humanized Antibody That Binds to the Interleukin 2 Receptor," Proc. Natl Acad. Sci. USA 86:10029-10033.

Ravetch, J.V. et al. (1991). "Fc Receptors," Annu. Rev. Immunol. 9:457-492.

Remington's Pharmaceutical Sciences. (1980). 16th edition, Osol, A. Ed, pp. 1-2, (Table of Contents Only).

Riechmann, L. et al. (Mar. 24, 1988). "Reshaping Human Antibodies for Therapy," Nature 332:323-327.

Ripka, J. et al. (Sep. 1986). "Two Chinese Hamster Ovary Glycosylation Mutants Affected in the Conversion of GDP-Mannose to GDP-Fucose," Arch Biochem Biophys. 249(2):533-545.

Romano, E. et al. (2015, e-pub. Apr. 21, 2015). "The Therapeutic Promise of Disrupting The PD-1/PD-L1 Immune Checkpoint In Cancer: Unleashing The CD8 T Cell Mediated Anti-Tumor Activity Results In Significant, Unprecedented Clinical Efficacy In Various Solid Tumors," Journal for Immunotherapy of Cancer 3:15, 5 pages.

Rosok, M.J. et al. (Sep. 13, 1996). "A Combinatorial Library Strategy for the Rapid Humanization of Anticarcinoma BR96 Fab," J. Biol. Chem. 271(37):22611-22618.

Running Deer, J. et al. (May-Jun. 2004, e-pub. Mar. 10, 2004). "High-Level Expression Of Proteins In Mammalian Cells Using Transcription Regulatory Sequences From The Chinese Hamster EF-1Alpha Gene," Biotechnol. Prog. 20(3):880-889.

Sambrook, J. et al. (2001). Molecular Cloning: A Laboratory Manual Cold Spring Harbor Laboratory Press, Cold Spring Harbor, N.Y., 3rd ed., 1 page, Table of Contents.

Shields, R.L. et al. (Mar. 2, 2001). "High Resolution Mapping of the Binding Site on Human IgG1 for FcγRI, FcγRII. FcγRIII, and FcRn and Design of IgG1 Variants With Improved Binding to the FcγR," J. Biol.Chem. 276(9):6591-6604.

Sidhu, S.S. et al. (2004). "Phage-Displayed Antibody Libraries of Synthetic Heavy Chain Complementarity Determining Regions," J. Mol. Biol. 338(2):299-310.

Sims, M.J. et al. (Aug. 15, 1993). "A Humanized CD18 Antibody Can Block Function Without Cell Destruction," J. Immunol. 151(4):2296-2308.

Sitaraman, K. et al. (2009). "High-Throughput Protein Expression Using Cell-Free System," Methods Mol. Biol. 498:229-244.

Skerra, A. (1993) "Bacterial Expression of Immunoglobulin Fragments," Current Opinion in Immunology 5:256-262.

Spirin, A.S. (Oct. 2004). "High-Throughput Cell-Free Systems For Synthesis Of Functionally Active Proteins," Trends Biotechnol. 22(10):538-545.

Spranger, S. et al. (Aug. 28, 2013). "Up-Regulation of PD-L1, IDO, and Tregs in the Melanoma Tumor Microenvironment Is Driven by CD8+ T Cells," Science Translational Medicine 5(200):200ra116, 21 pages.

Suarez, E.R. et al. (Apr. 29, 2016). "Chimeric Antigen Receptor T Cells Secreting Anti-PD-L1 Antibodies More Effectively Regress Renal Cell Carcinoma in a Humanized Mouse Model," Oncotarget 7(23):34341-34355.

Taube, J.M. et al. (Mar. 28, 2012). "Colocalization of Inflammatory Response With B7-H1 Expression in Human Melanocytic Lesions Supports an Adaptive Resistance Mechanism of Immune Escape," Science Translational Medicine 4(127):127ra137, 22 pages.

Taube, J.M. et al. (Oct. 1, 2015, e-pub. Apr. 8, 2014). "Association of PD-1, PD-1 Ligands, and Other Features of The Tumor Immune Microenvironment With Response To Anti-PD-1 Therapy," Clinical Cancer Research 20(19):5064-5074, 23 pages.

Thierauf, J. et al. (Dec. 2015). "Identification and Clinical Relevance of PD-L1 Expression In Primary Mucosal Malignant Melanoma of The Head and Neck," Melanoma Research 25(6):503-509.

Trotter, D.E.G. et al. (2017, e-pub. Jun. 6, 2017). "In Vivo Imaging of the Programmed Death Ligand 1 by 18F PET," J. Nucl. Med. 58(11):1852-1858.

Truillet, C. et al. (2018). "Imaging PD-L1 Expression With ImmunoPET." Bioconjugate Chemistry 29(1):96-103.

Tseng, S.-Y. et al. (Apr. 2, 2001). "B7-Dc, A New Dendritic Cell Molecule with Potent Costimulatory Properties for T Cells," J. Exp. Med. 193(7):839-846.

Van Dijk, M.A. et al. (Aug. 2001). "Human Antibodies as Next Generation Therapeutics," Curr. Opin. Che. Biology 5(4):368-374.

Vollmers, H.P. et al. (2005). "Death By Stress: Natural IgM-Induced Apoptosis," Methods and Findings in Experimental and Clinical Pharmacology 27(3):185-191.

Vollmers, H.P. et al. (2005). "The "Early Birds": Natural IgM Antibodies and Immune Surveillance," Histology and Histopathology, 20(3):927-937.

Wang, A. et al. (Apr. 2015, e-pub. Jan. 31, 2015). "The Prognostic Value of PD-L1 Expression For Non-Small Cell Lung Cancer Patients: A Meta-Analysis," European Journal of Surgical Oncology 41(4):450-456.

Waterhouse, P. et al. (1993). "Combinatorial Infection and in Vivo Recombination: a Strategy for Making Large Phage Antibody Repertoires," Nucl. Acids Res. 21(9):2265-2266.

Wei, W. et al. (Apr. 22, 2020). "ImmunoPet: Concept, Design, and Applications," 120(8):3787-3851, 145 pages.

Winter, G. et al. (1994). "Making Antibodies by Phage Display Technology," Ann. Rev. Immunol. 12:433-455.

Wright, A. et al. (Jan. 1997). "Effect of Glycosylation on Antibody Function: Implications for Genetic Engineering," Trends Biotech. 15:26-32.

Xiao, Y. et al. (May 5, 2014). "RGMb Is a Novel Binding Partner For PD-L2 and Its Engagement With PD-L2 Promotes Respiratory Tolerance," The Journal of Experimental Medicine 211(5):943-959.

Yamane-Ohnuki, N. et al. (Sep. 5, 2004, e-pub Aug. 6, 2004). "Establishment Of FUT8 Knockout Chinese Hamster Ovary Cells: An Ideal Host Cell Line For Producing Completely Defucosylated Antibodies With Enhanced Antibody-Dependent Cellular Cytotoxicity," Biotechnology and Bioengineering 87(5):614-622.

Yantha, J. et al. (Oct. 2010, e-pub. Jun. 3, 2010). "Unexpected Acceleration of Type 1 Diabetes by Transgenic Expression of B7-H1 in NOD Mouse Peri-Islet Glia," Diabetes 59(10):2588-2596.

Yao, S. et al. (Aug. 18, 2014, e-pub. Feb. 4, 2013). "Adaptive Resistance: A Tumor Strategy To Evade Immune Attack," European Journal of Immunology 43(3):576-579, 7 pages.

Yao, S. et al. (Jun. 2006, e-pub. May 2, 2006). "Reviving Exhausted T Lymphocytes During Chronic Virus Infection By B7-H1 Blockade," Trends In Molecular Medicine 12(6):244-246.

Zou, W. et al. (Jun. 2008). "Inhibitory B7-Family Molecules In The Tumour Microenvironment," Nature reviews Immunology 8(6):467-477.

Alsaab, H. O. et al. (Aug. 23, 2017). "PD-1 and PD-L1 Checkpoint Signaling Inhibition for Cancer Immunotherapy: Mechanism, Combinations, and Clinical Outcome," Frontiers in Pharmacology 561(8):1-15.

Chen, C. et al. (Jun. 15, 1995). "Enhancement and Destruction of Antibody Function by Somatic Mutation: Unequal Occurrence is Controlled by V Gene Combinatorial Associations," The EMBO Journal 14(12):2784-2794.

(56) References Cited

OTHER PUBLICATIONS

Extended European Search Report, dated Jun. 14, 2022, for European Patent Application No. 19811993.5, 16 pages.
Extended European Search Report, dated Oct. 25, 2022, for European Patent Application No. 20745563.5, 8 pages.
FDA (Jan. 31, 2018). "Compilation Series of Foreign Laws and Regulations on Foods and Drugs," FDA with English Translation, 10 pages.
Granier, C. et al. (Jul. 1, 2017). "Mechanisms of Action and Rationale for the Use of Checkpoint Inhibitors in Cancer," ESMO Open 2(2):e000213, 9 pages.
Kussie, P.H. et al. (1994). "A Single Engineered Amino Acid Substitution Changes Antibody Fine Specificity ," J. Immunol. 152:146-152.
Partial Supplementary European Search Report, dated Mar. 11, 2022, for European Patent Application No. 19811993.5, 19 pages.
Yang, D. et al. (Feb. 1, 2018, e-pub. Nov. 24, 2017). "Liposomal Nanohybrid Cerasomes Targeted to PD-L1 Enable Dual-Modality Imaging and Improve Antitumor Treatments," Cancer Letter 414:230-238.
Zhang, W. et al. (Apr. 2016). "Role of PD-1/PD-L1 Signaling Pathway in Immune Treatment of Malignant Tumors," China Medical Herald 13(12):57-60. English Translation Abstract.

\* cited by examiner

60 mins

120 mins

60 mins

120 mins

60 mins

120 mins

60 mins

120 mins

SEQUENCE LISTING

<160> NUMBER OF SEQ ID NOS: 57

<210> SEQ ID NO 1
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1

Gly Phe Asn Ile Lys Asp Thr Tyr
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Construct

<400> SEQUENCE: 2

Asp Thr Tyr Met Tyr
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic Construct

<400> SEQUENCE: 3

Gly Phe Asn Ile Lys Asp Thr
1               5

<210> SEQ ID NO 4
<211> LENGTH: 10
<212> TYPE: PRT
<213> ORGANISM: Artificial Sequence
<220> FEATURE:
<223> OTHER INFORMATION: Synthetic Construct

<400> SEQUENCE: 4

Gly Phe Asn Ile Lys Asp Thr Tyr Met Tyr
1               5                   10

<210> SEQ ID NO 5
<211> LENGTH: 6
<212> TYPE: PRT
<213> ORGANISM: Artificial Sequence
<220> FEATURE:
<223> OTHER INFORMATION: Synthetic Construct

<400> SEQUENCE: 5

Lys Asp Thr Tyr Met Tyr
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic Construct

<400> SEQUENCE: 6

Ile Asp Pro Ala Asn Asp Asn Thr
1               5

```
<210> SEQ ID NO 7
<211> LENGTH: 17
<212> TYPE: PRT
<213> ORGANISM: Artificial Sequence
<220> FEATURE:
<223> OTHER INFORMATION: Synthetic Construct

<400> SEQUENCE: 7

Arg Ile Asp Pro Ala Asn Asp Asn Thr Lys Tyr Ala Gln Lys Phe Gln
1               5                   10                  15

Gly

<210> SEQ ID NO 8
<211> LENGTH: 6
<212> TYPE: PRT
<213> ORGANISM: Artificial Sequence
<220> FEATURE:
<223> OTHER INFORMATION: Synthetic Construct

<400> SEQUENCE: 8

Asp Pro Ala Asn Asp Asn
1               5

<210> SEQ ID NO 9
<211> LENGTH: 10
<212> TYPE: PRT
<213> ORGANISM: Artificial Sequence
<220> FEATURE:
<223> OTHER INFORMATION: Synthetic Construct

<400> SEQUENCE: 9

Arg Ile Asp Pro Ala Asn Asp Asn Thr Lys
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Synthetic Construct

<400> SEQUENCE: 10

Trp Met Gly Arg Ile Asp Pro Ala Asn Asp Asn Thr Lys
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic Construct

<400> SEQUENCE: 11

Ala Arg Ala Lys Asn Leu Leu Asn Tyr Phe Asp Tyr
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetic Construct

<400> SEQUENCE: 12

Ala Lys Asn Leu Leu Asn Tyr Phe Asp Tyr
```

```
1               5                  10
```

<210> SEQ ID NO 13
<211> LENGTH: 11
<212> TYPE: PRT
<213> ORGANISM: Artificial Sequence
<220> FEATURE:
<223> OTHER INFORMATION: Synthetic Construct

<400> SEQUENCE: 13

```
Ala Arg Ala Lys Asn Leu Leu Asn Tyr Phe Asp
1               5                  10
```

<210> SEQ ID NO 14
<211> LENGTH: 6
<212> TYPE: PRT
<213> ORGANISM: Artificial Sequence
<220> FEATURE:
<223> OTHER INFORMATION: Synthetic Construct

<400> SEQUENCE: 14

```
Gln Glu Ile Ser Gly Tyr
1               5
```

<210> SEQ ID NO 15
<211> LENGTH: 11
<212> TYPE: PRT
<213> ORGANISM: Artificial Sequence
<220> FEATURE:
<223> OTHER INFORMATION: Synthetic Construct

<400> SEQUENCE: 15

```
Arg Ala Ser Gln Glu Ile Ser Gly Tyr Leu Ser
1               5                  10
```

<210> SEQ ID NO 16
<211> LENGTH: 7
<212> TYPE: PRT
<213> ORGANISM: Artificial Sequence
<220> FEATURE:
<223> OTHER INFORMATION: Synthetic Construct

<400> SEQUENCE: 16

```
Ser Gly Tyr Leu Ser Trp Leu
1               5
```

<210> SEQ ID NO 17
<211> LENGTH: 3
<212> TYPE: PRT
<213> ORGANISM: Artificial Sequence
<220> FEATURE:
<223> OTHER INFORMATION: Synthetic Construct

<400> SEQUENCE: 17

```
Ala Thr Ser
1
```

<210> SEQ ID NO 18
<211> LENGTH: 7
<212> TYPE: PRT
<213> ORGANISM: Artificial Sequence
<220> FEATURE:
<223> OTHER INFORMATION: Synthetic Construct

<400> SEQUENCE: 18

```
Ala Thr Ser Thr Leu Gln Ser
1               5
```

<210> SEQ ID NO 19
<211> LENGTH: 10
<212> TYPE: PRT
<213> ORGANISM: Artificial Sequence
<220> FEATURE:
<223> OTHER INFORMATION: Synthetic Construct

<400> SEQUENCE: 19

Arg Leu Ile Tyr Ala Thr Ser Thr Leu Gln
1               5                   10

<210> SEQ ID NO 20
<211> LENGTH: 9
<212> TYPE: PRT
<213> ORGANISM: Artificial Sequence
<220> FEATURE:
<223> OTHER INFORMATION: Synthetic Construct

<400> SEQUENCE: 20

Leu Gln Tyr Ala Ile Tyr Pro Leu Thr
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic Construct

<400> SEQUENCE: 21

Leu Gln Tyr Ala Ile Tyr Pro Leu
1               5

<210> SEQ ID NO 22
<211> LENGTH: 119
<212> TYPE: PRT
<213> ORGANISM: Artificial Sequence
<220> FEATURE:
<223> OTHER INFORMATION: Synthetic Construct

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Met Tyr Trp Val Arg Gln Ala Pro Gly Gln Gly Leu Glu Trp Met
        35                  40                  45

Gly Arg Ile Asp Pro Ala Asn Asp Asn Thr Lys Tyr Ala Gln Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Lys Asn Leu Leu Asn Tyr Phe Asp Tyr Trp Gly Gln Gly
            100                 105                 110

Thr Leu Val Thr Val Ser Ser
        115

<210> SEQ ID NO 23
<211> LENGTH: 119
<212> TYPE: PRT
<213> ORGANISM: Artificial Sequence

```
<220> FEATURE:
<223> OTHER INFORMATION: Synthetic Construct

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Met Tyr Trp Val Arg Gln Ala Pro Gly Gln Cys Leu Glu Trp Met
        35                  40                  45

Gly Arg Ile Asp Pro Ala Asn Asp Asn Thr Lys Tyr Ala Gln Lys Phe
    50                  55                  60

Gln Gly Arg Val Thr Ile Thr Ala Asp Thr Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Lys Asn Leu Leu Asn Tyr Phe Asp Tyr Trp Gly Gln Gly
            100                 105                 110

Thr Leu Val Thr Val Ser Ser
        115

<210> SEQ ID NO 24
<211> LENGTH: 119
<212> TYPE: PRT
<213> ORGANISM: Artificial Sequence
<220> FEATURE:
<223> OTHER INFORMATION: Synthetic Construct

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Met Tyr Trp Val Arg Gln Ala Pro Gly Gln Gly Leu Glu Trp Met
        35                  40                  45

Gly Arg Ile Asp Pro Ala Asn Asp Asn Thr Lys Tyr Ala Gln Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Lys Asn Leu Leu Asn Tyr Phe Asp Tyr Trp Gly Cys Gly
            100                 105                 110

Thr Leu Val Thr Val Ser Ser
        115

<210> SEQ ID NO 25
<211> LENGTH: 108
<212> TYPE: PRT
<213> ORGANISM: Artificial Sequence
<220> FEATURE:
<223> OTHER INFORMATION: Synthetic Construct

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30
```

```
Leu Ser Trp Leu Gln Gln Lys Pro Gly Lys Ala Pro Lys Arg Leu Ile
        35                  40                  45

Tyr Ala Thr Ser Thr Leu Gln Ser Gly Val Pro Ser Arg Phe Ser Gly
 50                  55                  60

Ser Arg Ser Gly Thr Asp Tyr Thr Leu Thr Ile Ser Ser Leu Gln Pro
 65                  70                  75                  80

Glu Asp Phe Ala Thr Tyr Tyr Cys Leu Gln Tyr Ala Ile Tyr Pro Leu
                 85                  90                  95

Thr Phe Gly Gln Gly Thr Lys Leu Glu Ile Lys Arg
            100                 105
```

<210> SEQ ID NO 26
<211> LENGTH: 108
<212> TYPE: PRT
<213> ORGANISM: Artificial Sequence
<220> FEATURE:
<223> OTHER INFORMATION: Synthetic Construct

<400> SEQUENCE: 26

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Glu Ile Ser Gly Tyr
             20                  25                  30

Leu Ser Trp Leu Gln Gln Lys Pro Gly Lys Ala Pro Lys Arg Leu Ile
        35                  40                  45

Tyr Ala Thr Ser Thr Leu Gln Ser Gly Val Pro Ser Arg Phe Ser Gly
 50                  55                  60

Ser Arg Ser Gly Thr Asp Tyr Thr Leu Thr Ile Ser Ser Leu Gln Pro
 65                  70                  75                  80

Glu Asp Phe Ala Thr Tyr Tyr Cys Leu Gln Tyr Ala Ile Tyr Pro Leu
                 85                  90                  95

Thr Phe Gly Cys Gly Thr Lys Leu Glu Ile Lys Arg
            100                 105
```

<210> SEQ ID NO 27
<211> LENGTH: 108
<212> TYPE: PRT
<213> ORGANISM: Artificial Sequence
<220> FEATURE:
<223> OTHER INFORMATION: Synthetic Construct

<400> SEQUENCE: 27

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Glu Ile Ser Gly Tyr
             20                  25                  30

Leu Ser Trp Leu Gln Gln Lys Pro Gly Lys Cys Pro Lys Arg Leu Ile
        35                  40                  45

Tyr Ala Thr Ser Thr Leu Gln Ser Gly Val Pro Ser Arg Phe Ser Gly
 50                  55                  60

Ser Arg Ser Gly Thr Asp Tyr Thr Leu Thr Ile Ser Ser Leu Gln Pro
 65                  70                  75                  80

Glu Asp Phe Ala Thr Tyr Tyr Cys Leu Gln Tyr Ala Ile Tyr Pro Leu
                 85                  90                  95

Thr Phe Gly Gln Gly Thr Lys Leu Glu Ile Lys Arg
            100                 105
```

<210> SEQ ID NO 28

```
<211> LENGTH: 9
<212> TYPE: PRT
<213> ORGANISM: Artificial Sequence
<220> FEATURE:
<223> OTHER INFORMATION: Synthetic Construct

<400> SEQUENCE: 28

Ala Lys Thr Thr Pro Lys Leu Gly Gly
1               5

<210> SEQ ID NO 29
<211> LENGTH: 10
<212> TYPE: PRT
<213> ORGANISM: Artificial Sequence
<220> FEATURE:
<223> OTHER INFORMATION: Synthetic Construct

<400> SEQUENCE: 29

Ser Ala Lys Thr Thr Pro Lys Leu Gly Gly
1               5                   10

<210> SEQ ID NO 30
<211> LENGTH: 6
<212> TYPE: PRT
<213> ORGANISM: Artificial Sequence
<220> FEATURE:
<223> OTHER INFORMATION: Synthetic Construct

<400> SEQUENCE: 30

Ser Ala Lys Thr Thr Pro
1               5

<210> SEQ ID NO 31
<211> LENGTH: 6
<212> TYPE: PRT
<213> ORGANISM: Artificial Sequence
<220> FEATURE:
<223> OTHER INFORMATION: Synthetic Construct

<400> SEQUENCE: 31

Arg Ala Asp Ala Ala Pro
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic Construct

<400> SEQUENCE: 32

Arg Ala Asp Ala Ala Pro Thr Val Ser
1               5

<210> SEQ ID NO 33
<211> LENGTH: 12
<212> TYPE: PRT
<213> ORGANISM: Artificial Sequence
<220> FEATURE:
<223> OTHER INFORMATION: Synthetic Construct

<400> SEQUENCE: 33

Arg Ala Asp Ala Ala Ala Ala Gly Gly Pro Gly Ser
1               5                   10

<210> SEQ ID NO 34
<211> LENGTH: 27
```

```
<212> TYPE: PRT
<213> ORGANISM: Artificial Sequence
<220> FEATURE:
<223> OTHER INFORMATION: Synthetic Construct

<400> SEQUENCE: 34

Arg Ala Asp Ala Ala Ala Gly Gly Gly Ser Gly Gly Gly Gly
1               5                   10                  15

Ser Gly Gly Gly Gly Ser Gly Gly Gly Ser
                20                  25

<210> SEQ ID NO 35
<211> LENGTH: 24
<212> TYPE: PRT
<213> ORGANISM: Artificial Sequence
<220> FEATURE:
<223> OTHER INFORMATION: Synthetic Construct

<400> SEQUENCE: 35

Met Asp Pro Lys Gly Ser Leu Ser Trp Arg Ile Leu Leu Phe Leu Ser
1               5                   10                  15

Leu Ala Phe Glu Leu Ser Tyr Gly
                20

<210> SEQ ID NO 36
<211> LENGTH: 236
<212> TYPE: PRT
<213> ORGANISM: Artificial Sequence
<220> FEATURE:
<223> OTHER INFORMATION: Synthetic Construct

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
                20                  25                  30

Tyr Met Tyr Trp Val Arg Gln Ala Pro Gly Gln Cys Leu Glu Trp Met
            35                  40                  45

Gly Arg Ile Asp Pro Ala Asn Asp Asn Thr Lys Tyr Ala Gln Lys Phe
        50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Lys Asn Leu Leu Asn Tyr Phe Asp Tyr Trp Gly Gln Gly
            100                 105                 110

Thr Leu Val Thr Val Ser Ser Ala Lys Thr Thr Pro Lys Leu Gly Gly
        115                 120                 125

Asp Ile Gln Met Thr Gln Ser Pro Ser Ser Leu Ser Ala Ser Val Gly
    130                 135                 140

Asp Arg Val Thr Ile Thr Cys Arg Ala Ser Gln Glu Ile Ser Gly Tyr
145                 150                 155                 160

Leu Ser Trp Leu Gln Gln Lys Pro Gly Lys Ala Pro Lys Arg Leu Ile
                165                 170                 175

Tyr Ala Thr Ser Thr Leu Gln Ser Gly Val Pro Ser Arg Phe Ser Gly
            180                 185                 190

Ser Arg Ser Gly Thr Asp Tyr Thr Leu Thr Ile Ser Ser Leu Gln Pro
        195                 200                 205

Glu Asp Phe Ala Thr Tyr Tyr Cys Leu Gln Tyr Ala Ile Tyr Pro Leu
```

```
                 210                 215                 220
Thr Phe Gly Cys Gly Thr Lys Leu Glu Ile Lys Arg
225                 230                 235
```

<210> SEQ ID NO 37
<211> LENGTH: 241
<212> TYPE: PRT
<213> ORGANISM: Artificial Sequence
<220> FEATURE:
<223> OTHER INFORMATION: Synthetic Construct

<400> SEQUENCE: 37

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
                20                  25                  30

Tyr Met Tyr Trp Val Arg Gln Ala Pro Gly Gln Cys Leu Glu Trp Met
            35                  40                  45

Gly Arg Ile Asp Pro Ala Asn Asp Asn Thr Lys Tyr Ala Gln Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Lys Asn Leu Leu Asn Tyr Phe Asp Tyr Trp Gly Gln Gly
            100                 105                 110

Thr Leu Val Thr Val Ser Ser Ala Lys Thr Thr Pro Lys Leu Gly Gly
        115                 120                 125

Asp Ile Gln Met Thr Gln Ser Pro Ser Ser Leu Ser Ala Ser Val Gly
    130                 135                 140

Asp Arg Val Thr Ile Thr Cys Arg Ala Ser Gln Glu Ile Ser Gly Tyr
145                 150                 155                 160

Leu Ser Trp Leu Gln Gln Lys Pro Gly Lys Ala Pro Lys Arg Leu Ile
                165                 170                 175

Tyr Ala Thr Ser Thr Leu Gln Ser Gly Val Pro Ser Arg Phe Ser Gly
            180                 185                 190

Ser Arg Ser Gly Thr Asp Tyr Thr Leu Thr Ile Ser Ser Leu Gln Pro
        195                 200                 205

Glu Asp Phe Ala Thr Tyr Tyr Cys Leu Gln Tyr Ala Ile Tyr Pro Leu
    210                 215                 220

Thr Phe Gly Cys Gly Thr Lys Leu Glu Ile Lys Arg Gly Gly Gly Gly
225                 230                 235                 240

Ser
```

<210> SEQ ID NO 38
<211> LENGTH: 236
<212> TYPE: PRT
<213> ORGANISM: Artificial Sequence
<220> FEATURE:
<223> OTHER INFORMATION: Synthetic Construct

<400> SEQUENCE: 38

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
                20                  25                  30

Tyr Met Tyr Trp Val Arg Gln Ala Pro Gly Gln Gly Leu Glu Trp Met
```

```
            35                  40                  45
Gly Arg Ile Asp Pro Ala Asn Asp Asn Thr Lys Tyr Ala Gln Lys Phe
 50                  55                  60

Gln Gly Arg Val Thr Ile Thr Ala Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ala Lys Asn Leu Leu Asn Tyr Phe Asp Tyr Trp Gly Cys Gly
                100                 105                 110

Thr Leu Val Thr Val Ser Ser Ala Lys Thr Thr Pro Lys Leu Gly Gly
                115                 120                 125

Asp Ile Gln Met Thr Gln Ser Pro Ser Ser Leu Ser Ala Ser Val Gly
                130                 135                 140

Asp Arg Val Thr Ile Thr Cys Arg Ala Ser Gln Glu Ile Ser Gly Tyr
145                 150                 155                 160

Leu Ser Trp Leu Gln Gln Lys Pro Gly Lys Cys Pro Lys Arg Leu Ile
                165                 170                 175

Tyr Ala Thr Ser Thr Leu Gln Ser Gly Val Pro Ser Arg Phe Ser Gly
                180                 185                 190

Ser Arg Ser Gly Thr Asp Tyr Thr Leu Thr Ile Ser Ser Leu Gln Pro
                195                 200                 205

Glu Asp Phe Ala Thr Tyr Tyr Cys Leu Gln Tyr Ala Ile Tyr Pro Leu
                210                 215                 220

Thr Phe Gly Gln Gly Thr Lys Leu Glu Ile Lys Arg
225                 230                 235

<210> SEQ ID NO 39
<211> LENGTH: 241
<212> TYPE: PRT
<213> ORGANISM: Artificial Sequence
<220> FEATURE:
<223> OTHER INFORMATION: Synthetic Construct

<400> SEQUENCE: 39

Gln Val Gln Leu Val Gln Ser Gly Ala Glu Val Lys Lys Pro Gly Ala
 1               5                  10                  15

Ser Val Lys Val Ser Cys Lys Ala Ser Gly Phe Asn Ile Lys Asp Thr
                20                  25                  30

Tyr Met Tyr Trp Val Arg Gln Ala Pro Gly Gln Gly Leu Glu Trp Met
                35                  40                  45

Gly Arg Ile Asp Pro Ala Asn Asp Asn Thr Lys Tyr Ala Gln Lys Phe
 50                  55                  60

Gln Gly Arg Val Thr Ile Thr Ala Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ala Lys Asn Leu Leu Asn Tyr Phe Asp Tyr Trp Gly Cys Gly
                100                 105                 110

Thr Leu Val Thr Val Ser Ser Ala Lys Thr Thr Pro Lys Leu Gly Gly
                115                 120                 125

Asp Ile Gln Met Thr Gln Ser Pro Ser Ser Leu Ser Ala Ser Val Gly
                130                 135                 140

Asp Arg Val Thr Ile Thr Cys Arg Ala Ser Gln Glu Ile Ser Gly Tyr
145                 150                 155                 160

Leu Ser Trp Leu Gln Gln Lys Pro Gly Lys Cys Pro Lys Arg Leu Ile
```

```
            165                 170                 175
Tyr Ala Thr Ser Thr Leu Gln Ser Gly Val Pro Ser Arg Phe Ser Gly
            180                 185                 190

Ser Arg Ser Gly Thr Asp Tyr Thr Leu Thr Ile Ser Ser Leu Gln Pro
            195                 200                 205

Glu Asp Phe Ala Thr Tyr Tyr Cys Leu Gln Tyr Ala Ile Tyr Pro Leu
            210                 215                 220

Thr Phe Gly Gln Gly Thr Lys Leu Glu Ile Lys Arg Gly Gly Gly Gly
225                 230                 235                 240

Ser

<210> SEQ ID NO 40
<211> LENGTH: 260
<212> TYPE: PRT
<213> ORGANISM: Artificial Sequence
<220> FEATURE:
<223> OTHER INFORMATION: Synthetic Construct

<400> SEQUENCE: 40

Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Val Gln Ser Gly
            20                  25                  30

Ala Glu Val Lys Lys Pro Gly Ala Ser Val Lys Val Ser Cys Lys Ala
            35                  40                  45

Ser Gly Phe Asn Ile Lys Asp Thr Tyr Met Tyr Trp Val Arg Gln Ala
        50                  55                  60

Pro Gly Gln Cys Leu Glu Trp Met Gly Arg Ile Asp Pro Ala Asn Asp
65                  70                  75                  80

Asn Thr Lys Tyr Ala Gln Lys Phe Gln Gly Arg Val Thr Ile Thr Ala
                85                  90                  95

Asp Thr Ser Thr Ser Thr Ala Tyr Met Glu Leu Ser Ser Leu Arg Ser
            100                 105                 110

Glu Asp Thr Ala Val Tyr Tyr Cys Ala Arg Ala Lys Asn Leu Leu Asn
            115                 120                 125

Tyr Phe Asp Tyr Trp Gly Gln Gly Thr Leu Val Thr Val Ser Ser Ala
    130                 135                 140

Lys Thr Thr Pro Lys Leu Gly Gly Asp Ile Gln Met Thr Gln Ser Pro
145                 150                 155                 160

Ser Ser Leu Ser Ala Ser Val Gly Asp Arg Val Thr Ile Thr Cys Arg
                165                 170                 175

Ala Ser Gln Glu Ile Ser Gly Tyr Leu Ser Trp Leu Gln Gln Lys Pro
            180                 185                 190

Gly Lys Ala Pro Lys Arg Leu Ile Tyr Ala Thr Ser Thr Leu Gln Ser
            195                 200                 205

Gly Val Pro Ser Arg Phe Ser Gly Ser Arg Ser Gly Thr Asp Tyr Thr
        210                 215                 220

Leu Thr Ile Ser Ser Leu Gln Pro Glu Asp Phe Ala Thr Tyr Tyr Cys
225                 230                 235                 240

Leu Gln Tyr Ala Ile Tyr Pro Leu Thr Phe Gly Cys Gly Thr Lys Leu
                245                 250                 255

Glu Ile Lys Arg
            260

<210> SEQ ID NO 41
```

```
<211> LENGTH: 265
<212> TYPE: PRT
<213> ORGANISM: Artificial Sequence
<220> FEATURE:
<223> OTHER INFORMATION: Synthetic Construct

<400> SEQUENCE: 41

Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Val Gln Ser Gly
            20                  25                  30

Ala Glu Val Lys Lys Pro Gly Ala Ser Val Lys Val Ser Cys Lys Ala
        35                  40                  45

Ser Gly Phe Asn Ile Lys Asp Thr Tyr Met Tyr Trp Val Arg Gln Ala
    50                  55                  60

Pro Gly Gln Cys Leu Glu Trp Met Gly Arg Ile Asp Pro Ala Asn Asp
65                  70                  75                  80

Asn Thr Lys Tyr Ala Gln Lys Phe Gln Gly Arg Val Thr Ile Thr Ala
                85                  90                  95

Asp Thr Ser Thr Ser Thr Ala Tyr Met Glu Leu Ser Ser Leu Arg Ser
            100                 105                 110

Glu Asp Thr Ala Val Tyr Tyr Cys Ala Arg Ala Lys Asn Leu Leu Asn
        115                 120                 125

Tyr Phe Asp Tyr Trp Gly Gln Gly Thr Leu Val Thr Val Ser Ser Ala
    130                 135                 140

Lys Thr Thr Pro Lys Leu Gly Gly Asp Ile Gln Met Thr Gln Ser Pro
145                 150                 155                 160

Ser Ser Leu Ser Ala Ser Val Gly Asp Arg Val Thr Ile Thr Cys Arg
                165                 170                 175

Ala Ser Gln Glu Ile Ser Gly Tyr Leu Ser Trp Leu Gln Lys Pro
            180                 185                 190

Gly Lys Ala Pro Lys Arg Leu Ile Tyr Ala Thr Ser Thr Leu Gln Ser
        195                 200                 205

Gly Val Pro Ser Arg Phe Ser Gly Ser Arg Ser Gly Thr Asp Tyr Thr
    210                 215                 220

Leu Thr Ile Ser Ser Leu Gln Pro Glu Asp Phe Ala Thr Tyr Tyr Cys
225                 230                 235                 240

Leu Gln Tyr Ala Ile Tyr Pro Leu Thr Phe Gly Cys Gly Thr Lys Leu
                245                 250                 255

Glu Ile Lys Arg Gly Gly Gly Gly Ser
            260                 265

<210> SEQ ID NO 42
<211> LENGTH: 260
<212> TYPE: PRT
<213> ORGANISM: Artificial Sequence
<220> FEATURE:
<223> OTHER INFORMATION: Synthetic Construct

<400> SEQUENCE: 42

Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Val Gln Ser Gly
            20                  25                  30

Ala Glu Val Lys Lys Pro Gly Ala Ser Val Lys Val Ser Cys Lys Ala
        35                  40                  45

Ser Gly Phe Asn Ile Lys Asp Thr Tyr Met Tyr Trp Val Arg Gln Ala
```

```
                    50                  55                  60
Pro Gly Gln Gly Leu Glu Trp Met Gly Arg Ile Asp Pro Ala Asn Asp
 65                  70                  75                  80

Asn Thr Lys Tyr Ala Gln Lys Phe Gln Gly Arg Val Thr Ile Thr Ala
                     85                  90                  95

Asp Thr Ser Thr Ser Thr Ala Tyr Met Glu Leu Ser Ser Leu Arg Ser
                    100                 105                 110

Glu Asp Thr Ala Val Tyr Tyr Cys Ala Arg Ala Lys Asn Leu Leu Asn
                115                 120                 125

Tyr Phe Asp Tyr Trp Gly Cys Gly Thr Leu Val Thr Val Ser Ser Ala
            130                 135                 140

Lys Thr Thr Pro Lys Leu Gly Gly Asp Ile Gln Met Thr Gln Ser Pro
145                 150                 155                 160

Ser Ser Leu Ser Ala Ser Val Gly Asp Arg Val Thr Ile Thr Cys Arg
                165                 170                 175

Ala Ser Gln Glu Ile Ser Gly Tyr Leu Ser Trp Leu Gln Gln Lys Pro
            180                 185                 190

Gly Lys Cys Pro Lys Arg Leu Ile Tyr Ala Thr Ser Thr Leu Gln Ser
        195                 200                 205

Gly Val Pro Ser Arg Phe Ser Gly Ser Arg Ser Gly Thr Asp Tyr Thr
        210                 215                 220

Leu Thr Ile Ser Ser Leu Gln Pro Glu Asp Phe Ala Thr Tyr Tyr Cys
225                 230                 235                 240

Leu Gln Tyr Ala Ile Tyr Pro Leu Thr Phe Gly Gln Gly Thr Lys Leu
                245                 250                 255

Glu Ile Lys Arg
            260

<210> SEQ ID NO 43
<211> LENGTH: 265
<212> TYPE: PRT
<213> ORGANISM: Artificial Sequence
<220> FEATURE:
<223> OTHER INFORMATION: Synthetic Construct

<400> SEQUENCE: 43

Met Asp Pro Lys Gly Ser Leu Ser Trp Arg Ile Leu Leu Phe Leu Ser
 1               5                  10                  15

Leu Ala Phe Glu Leu Ser Tyr Gly Gln Val Gln Leu Val Gln Ser Gly
                 20                  25                  30

Ala Glu Val Lys Lys Pro Gly Ala Ser Val Lys Val Ser Cys Lys Ala
             35                  40                  45

Ser Gly Phe Asn Ile Lys Asp Thr Tyr Met Tyr Trp Val Arg Gln Ala
         50                  55                  60

Pro Gly Gln Gly Leu Glu Trp Met Gly Arg Ile Asp Pro Ala Asn Asp
 65                  70                  75                  80

Asn Thr Lys Tyr Ala Gln Lys Phe Gln Gly Arg Val Thr Ile Thr Ala
                     85                  90                  95

Asp Thr Ser Thr Ser Thr Ala Tyr Met Glu Leu Ser Ser Leu Arg Ser
                100                 105                 110

Glu Asp Thr Ala Val Tyr Tyr Cys Ala Arg Ala Lys Asn Leu Leu Asn
            115                 120                 125

Tyr Phe Asp Tyr Trp Gly Cys Gly Thr Leu Val Thr Val Ser Ser Ala
        130                 135                 140

Lys Thr Thr Pro Lys Leu Gly Gly Asp Ile Gln Met Thr Gln Ser Pro
```

```
                145                 150                 155                 160
            Ser Ser Leu Ser Ala Ser Val Gly Asp Arg Val Thr Ile Thr Cys Arg
                            165                 170                 175

Ala Ser Gln Glu Ile Ser Gly Tyr Leu Ser Trp Leu Gln Gln Lys Pro
                            180                 185                 190

Gly Lys Cys Pro Lys Arg Leu Ile Tyr Ala Thr Ser Thr Leu Gln Ser
                            195                 200                 205

Gly Val Pro Ser Arg Phe Ser Gly Ser Arg Ser Gly Thr Asp Tyr Thr
                            210                 215                 220

Leu Thr Ile Ser Ser Leu Gln Pro Glu Asp Phe Ala Thr Tyr Tyr Cys
            225                 230                 235                 240

Leu Gln Tyr Ala Ile Tyr Pro Leu Thr Phe Gly Gln Gly Thr Lys Leu
                            245                 250                 255

Glu Ile Lys Arg Gly Gly Gly Ser
                            260                 265

<210> SEQ ID NO 44
<211> LENGTH: 357
<212> TYPE: DNA
<213> ORGANISM: Artificial Sequence
<220> FEATURE:
<223> OTHER INFORMATION: Synthetic Construct

<400> SEQUENCE: 44
caggttcagc tggtgcagtc tggggcagag gttaagaagc caggggcctc agtcaaggtg      60
tcctgcaagg cttctggctt caacattaaa gacacctata tgtactgggt gaggcaggca     120
cctggacagt gcctggagtg gatgggaagg attgatcctg ccaatgataa tactaaatat     180
gcccagaagt tccagggcag ggtcactata acagcagaca catccaccag cacagcctac     240
atggagctct ccagtctgag atctgaggac actgccgtct attactgtgc tagagccaag     300
aatttgttaa attactttga ctactggggc caaggcaccc ttgtcacagt ctcctca       357

<210> SEQ ID NO 45
<211> LENGTH: 324
<212> TYPE: DNA
<213> ORGANISM: Artificial Sequence
<220> FEATURE:
<223> OTHER INFORMATION: Synthetic Construct

<400> SEQUENCE: 45
gacatccaga tgacccagtc tccatcctcc ttatctgcct ctgtgggaga tagagtcact      60
atcacttgtc gggcaagtca ggaaattagt ggttacttaa gctggcttca gcagaaacca     120
ggtaaggctc ctaaacgcct gatctacgcc acatccactt tacagtctgg tgtcccaagt     180
aggttcagtg gcagtaggtc tgggacagat tatactctca ccatcagcag ccttcagcct     240
gaagattttg caacctatta ctgtctacaa tatgctattt atcctctcac cttcggttgt     300
gggaccaagc tggagatcaa acgg                                            324

<210> SEQ ID NO 46
<211> LENGTH: 27
<212> TYPE: DNA
<213> ORGANISM: Artificial Sequence
<220> FEATURE:
<223> OTHER INFORMATION: Synthetic Construct

<400> SEQUENCE: 46
gcgaaaacca ccccgaaact gggcggc                                          27
```

<210> SEQ ID NO 47
<211> LENGTH: 72
<212> TYPE: DNA
<213> ORGANISM: Artificial Sequence
<220> FEATURE:
<223> OTHER INFORMATION: Synthetic Construct

<400> SEQUENCE: 47

```
atggacccca agggcagcct gagctggaga atcctgctgt tcctgagcct ggccttcgag    60
ctgagctacg gc                                                         72
```

<210> SEQ ID NO 48
<211> LENGTH: 708
<212> TYPE: DNA
<213> ORGANISM: Artificial Sequence
<220> FEATURE:
<223> OTHER INFORMATION: Synthetic Construct

<400> SEQUENCE: 48

```
caggttcagc tggtgcagtc tggggcagag gttaagaagc caggggcctc agtcaaggtg    60
tcctgcaagg cttctggctt caacattaaa gacacctata tgtactgggt gaggcaggca   120
cctggacagt gcctggagtg gatgggaagg attgatcctg ccaatgataa tactaaatat   180
gcccagaagt tccagggcag ggtcactata acagcagaca catccaccag cacagcctac   240
atggagctct ccagtctgag atctgaggac actgccgtct attactgtgc tagagccaag   300
aatttgttaa attactttga ctactggggc caaggcaccc ttgtcacagt ctcctcagcg   360
aaaaccaccc cgaaactggg cggcgacatc cagatgaccc agtctccatc ctccttatct   420
gcctctgtgg gagatagagt cactatcact tgtcgggcaa gtcaggaaat tagtggttac   480
ttaagctggc ttcagcagaa accaggtaag gctcctaaac gcctgatcta cgccacatcc   540
actttacagt ctggtgtccc aagtaggttc agtggcagta ggtctgggac agattatact   600
ctcaccatca gcagccttca gcctgaagat tttgcaacct attactgtct acaatatgct   660
atttatcctc tcaccttcgg ttgtgggacc aagctggaga tcaaacgg              708
```

<210> SEQ ID NO 49
<211> LENGTH: 723
<212> TYPE: DNA
<213> ORGANISM: Artificial Sequence
<220> FEATURE:
<223> OTHER INFORMATION: Synthetic Construct

<400> SEQUENCE: 49

```
caggttcagc tggtgcagtc tggggcagag gttaagaagc caggggcctc agtcaaggtg    60
tcctgcaagg cttctggctt caacattaaa gacacctata tgtactgggt gaggcaggca   120
cctggacagt gcctggagtg gatgggaagg attgatcctg ccaatgataa tactaaatat   180
gcccagaagt tccagggcag ggtcactata acagcagaca catccaccag cacagcctac   240
atggagctct ccagtctgag atctgaggac actgccgtct attactgtgc tagagccaag   300
aatttgttaa attactttga ctactggggc caaggcaccc ttgtcacagt ctcctcagcg   360
aaaaccaccc cgaaactggg cggcgacatc cagatgaccc agtctccatc ctccttatct   420
gcctctgtgg gagatagagt cactatcact tgtcgggcaa gtcaggaaat tagtggttac   480
ttaagctggc ttcagcagaa accaggtaag gctcctaaac gcctgatcta cgccacatcc   540
actttacagt ctggtgtccc aagtaggttc agtggcagta ggtctgggac agattatact   600
ctcaccatca gcagccttca gcctgaagat tttgcaacct attactgtct acaatatgct   660
```
atttatcctc tcaccttcgg ttgtgggacc aagctggaga tcaaacgggg aggtggtggg    720
tct                                                                  723

<210> SEQ ID NO 50
<211> LENGTH: 780
<212> TYPE: DNA
<213> ORGANISM: Artificial Sequence
<220> FEATURE:
<223> OTHER INFORMATION: Synthetic Construct

<400> SEQUENCE: 50
atggacccca agggcagcct gagctggaga tcctgctgt tcctgagcct ggccttcgag     60
ctgagctacg gccaggttca gctggtgcag tctggggcag aggttaagaa gccaggggcc   120
tcagtcaagg tgtcctgcaa ggcttctggc ttcaacatta agacaccta tatgtactgg   180 gtgaggcagg cacctggaca gtgcctggag tggatgggaa ggattgatcc tgccaatgat   240
aatactaaat atgcccagaa gttccagggc agggtcacta taacagcaga cacatccacc   300
agcacagcct acatggagct ctccagtctg agatctgagg acactgccgt ctattactgt   360
gctagagcca agaatttgtt aaattacttt gactactggg gccaaggcac ccttgtcaca   420
gtctcctcag cgaaaaccac cccgaaactg gcggcgaca tccagatgac ccagtctcca   480
tcctccttat ctgcctctgt gggagataga gtcactatca cttgtcgggc aagtcaggaa   540
attagtggtt acttaagctg gcttcagcag aaaccaggta aggctcctaa acgcctgatc   600
tacgccacat ccactttaca gtctggtgtc ccaagtaggt tcagtggcag taggtctggg   660
acagattata ctctcaccat cagcagcctt cagcctgaag attttgcaac ctattactgt   720
ctacaatatg ctatttatcc tctcaccttc ggttgtggga ccaagctgga gatcaaacgg   780

<210> SEQ ID NO 51
<211> LENGTH: 795
<212> TYPE: DNA
<213> ORGANISM: Artificial Sequence
<220> FEATURE:
<223> OTHER INFORMATION: Synthetic Construct

<400> SEQUENCE: 51
atggacccca agggcagcct gagctggaga tcctgctgt tcctgagcct ggccttcgag     60
ctgagctacg gccaggttca gctggtgcag tctggggcag aggttaagaa gccaggggcc   120
tcagtcaagg tgtcctgcaa ggcttctggc ttcaacatta agacaccta tatgtactgg   180 gtgaggcagg cacctggaca gtgcctggag tggatgggaa ggattgatcc tgccaatgat   240
aatactaaat atgcccagaa gttccagggc agggtcacta taacagcaga cacatccacc   300
agcacagcct acatggagct ctccagtctg agatctgagg acactgccgt ctattactgt   360
gctagagcca agaatttgtt aaattacttt gactactggg gccaaggcac ccttgtcaca   420
gtctcctcag cgaaaaccac cccgaaactg gcggcgaca tccagatgac ccagtctcca   480
tcctccttat ctgcctctgt gggagataga gtcactatca cttgtcgggc aagtcaggaa   540
attagtggtt acttaagctg gcttcagcag aaaccaggta aggctcctaa acgcctgatc   600
tacgccacat ccactttaca gtctggtgtc ccaagtaggt tcagtggcag taggtctggg   660
acagattata ctctcaccat cagcagcctt cagcctgaag attttgcaac ctattactgt   720
ctacaatatg ctatttatcc tctcaccttc ggttgtggga ccaagctgga gatcaaacgg   780
ggaggtggtg ggtct                                                    795

```
<210> SEQ ID NO 52
<211> LENGTH: 33
<212> TYPE: DNA
<213> ORGANISM: Artificial Sequence
<220> FEATURE:
<223> OTHER INFORMATION: Synthetic Construct

<400> SEQUENCE: 52
aagcttgcca ccatggaccc caagggcagc ctg                                    33

<210> SEQ ID NO 53
<211> LENGTH: 37
<212> TYPE: DNA
<213> ORGANISM: Artificial Sequence
<220> FEATURE:
<223> OTHER INFORMATION: Synthetic Construct

<400> SEQUENCE: 53
gtttcggggt ggttttcgct gaggagactg tgacaag                                37

<210> SEQ ID NO 54
<211> LENGTH: 38
<212> TYPE: DNA
<213> ORGANISM: Artificial Sequence
<220> FEATURE:
<223> OTHER INFORMATION: Synthetic Construct

<400> SEQUENCE: 54
ccaccccgaa actgggcggc gacatccaga tgacccag                               38

<210> SEQ ID NO 55
<211> LENGTH: 24
<212> TYPE: DNA
<213> ORGANISM: Artificial Sequence
<220> FEATURE:
<223> OTHER INFORMATION: Synthetic Construct

<400> SEQUENCE: 55
gaattcttat caatggtgat ggtg                                              24

<210> SEQ ID NO 56
<211> LENGTH: 5
<212> TYPE: PRT
<213> ORGANISM: Artificial Sequence
<220> FEATURE:
<223> OTHER INFORMATION: Synthetic Construct

<400> SEQUENCE: 56

Gly Gly Gly Gly Ser
1               5

<210> SEQ ID NO 57
<211> LENGTH: 11
<212> TYPE: PRT
<213> ORGANISM: Artificial Sequence
<220> FEATURE:
<223> OTHER INFORMATION: Synthetic Construct

<400> SEQUENCE: 57

Gly Gly Gly Gly Ser His His His His His His
1               5                   10
```

ANTI-PD-L1 DIABODIES AND THE USE THEREOF

CROSS REFERENCE TO RELATED APPLICATIONS

This application is a national stage application under 35 U.S.C. § 371 of International Application No. PCT/CN2020/072572, filed internationally on Jan. 17, 2020, which claims the benefit of priority to PCT International Application No. PCT/2019/072810, filed internationally Jan. 23, 2019.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 792572000500SUBSEQLIST.txt, date recorded: Jul. 31, 2024, size: 36,204 bytes).

FIELD OF THE INVENTION

The present invention relates to diabodies, imaging agents, and methods of imaging PD-L1 and methods of treating a disease or condition.

BACKGROUND OF THE INVENTION

The Programmed Death (PD) network involves at least five interacting molecules: PD-1 (Programmed Cell Death 1), two PD-1 ligands (PD-L1 and PD-L2), and two inhibitory receptors (PD-1 and CD80) of PD-L1. The crucial function of the PD pathway in modulating the activity of T cells in the peripheral tissues in an inflammatory response to infection and in limiting autoimmunity appears to be hijacked by tumor cells and by viruses during chronic viral infections. PD-L1 is overexpressed on many freshly isolated human tumors from multiple tissue origins (Dong et al. *Nature Medicine* 2002; 8:793-800; Romano et al. *Journal for Immunotherapy of Cancer* 2015; 3:15; Hirano et al. *Cancer Research* 2005; 65:1089-1096). The expression of PD-L1 has been correlated with the progression and poor prognosis of certain types of human cancers (Wang et al. *European journal of surgical oncology: the journal of the European Society of Surgical Oncology and the British Association of Surgical Oncology* 2015; 41:450-456; Cierna et al. *Annals of oncology: official journal of the European Society for Medical Oncology/ESMO* 2016; 27:300-305; Gandini et al. *Critical reviews in oncology hematology* 2016; 100:88-98; Thierauf et al. *Melanoma research* 2015; 25:503-509; Taube et al. *Clinical cancer research: an official journal of the American Association for Cancer Research* 2014; 20:5064-5074). During chronic viral infections, PD-L1 is persistently expressed on many tissues, while PD-1 is up-regulated on virus-specific CTLs (Yao et al. *Trends in molecular medicine* 2006; 12:244-246). Tumor- or virus-induced PD-L1 may utilize multiple mechanisms to facilitate the evasion of host immune surveillance, including T cell anergy, apoptosis, exhaustion, IL-10 production, DC suppression, as well as Treg induction and expansion (Zou et al. *Nature reviews Immunology* 2008; 8:467-477).

The PD-L1 expression level determined using immunohistochemistry (IHC) has been assessed as a predictive biomarker in clinical trials of PD-1/PD-L1-directed therapy on multiple cancer types, including melanoma, renal cell carcinoma (RCC), non-small cell lung cancer (NSCLC), metastatic colorectal cancer (mCRC), and metastatic castration-resistant prostate cancer (mCRPC). Patients with higher levels of PD-L1 determined by IHC appeared to have superior responses to PD-1/PD-L1-directed therapy. However, PD-L1-negative patients with melanoma can still obtain durable response to anti-PD-1/PD-L1 therapy, while response rates in PD-L1-negative NSCLC patients are rare.

The accuracy of PD-L1 detection by IHC in human tumor specimens is confounded by multiple factors. A multitude of PD-L1 antibodies for IHC detection have been utilized, including 28-8, 22C3, 5H1, MIH1, and 405.9A11. In addition, a number of proprietary companion diagnostics are being developed in this area, such as Ventana SP142 and Ventana SP263 assay. Comparative performance characteristics of these assays are not well known. In addition to the existing issue of heterogeneous PD-L1 expression within the tumor microenvironment, there's also a lack of a clear definition of "positive" PD-L1 staining by IHC in tumor samples. Cut-off points for a positive result could range from >1% to >50%, based on percent tumor cells stained. Furthermore, PD-L1 has limited binding sites for IHC detection antibodies, as it contains only two small hydrophilic regions, which makes immunohistochemical approaches classically used in formalin-fixed, paraffin-embedded (FFPE) specimens less effective. Due to the lack of binding sites on PD-L1, IHC antibodies typically bind PD-L1 at structurally unique sites compared with therapeutic PD-L1 antibodies.

Additionally, PD-L1 is biologically active only when expressed on the cell membrane, either through dynamic IFNγ expression or through constitutive oncogene activation. Oncogene-driven PD-L1 expression represents a histopathologically and biologically distinct entity compared to inflammation driven PD-L1 expression. While the latter occurs focally at sites of IFNγ-mediated immunologic attack, oncogene-driven PD-L1 expression is constitutive and diffuse. IFNγ induced PD-L1 expression represents a dynamic biomarker and is present at sites of active inflammation, and biopsy samples represent a snapshot of the tumor immune microenvironment in space and time. Other factors in the tumor metabolic microenvironment, including hypoxia, can result in PD-L1 upregulation and are dependent on signaling via HIF1a. Smaller tumor biopsies may miss the pertinent tumor-immune interface, or the biopsy may be performed after the biologically relevant PD-L1 overexpression has already taken place. PD-L1 itself is expressed at two potentially clinically relevant immunologic synapses—the tumor/T-cell interface, as well as the APC/T-cell interface. For the tumor/T-cell interface, biopsy capture of the tumor/immune interface is a key determinant in PD-L1 detection by IHC in melanoma. In a study assessing PD-L1 expression in patients with metastatic melanoma, 96% of PD-L1-overexpressing melanomas had lymphocytic infiltrate (TIL), while the remaining 4% of PD-L1-overexpressing lacked TILs, possibly representing oncogene-driven PD-L1 expression. In addition, 22% of PD-L1 negative samples were associated with TIL, indicating alternative mechanisms of tumor immune interference.

The majority of PD-L1 expression occurs at the tumor interface, with immune cells secreting IFNγ, leading to the counterintuitive hypothesis that PD-L1 overexpression may be an initially protective response to successful tumor killing by TILs, which over time becomes co-opted into an immunosuppressive tumor environment. In addition, selection of the appropriate site for biopsy for PD-L1 detection remains enigmatic. While pretreatment FFPE primary tumor samples may be most readily available, these samples may not reflect the overall immunologic state that currently exists in a given patient, particularly if interim treatment has been administered. The absence of PD-L1 expression in a biopsied lesion may not reflect the systemic immunologic landscape, and may not capture the beneficial effect of the therapy at other sites of the disease that are dependent on PD-L1 signaling. In summary, there is an unmet need for accurate and alternative PD-L1 detection agents and methods.

The disclosures of all publications, patents, patent applications and published patent applications referred to herein are hereby incorporated herein by reference in their entirety.

BRIEF SUMMARY OF THE INVENTION

The present application provides anti-PD-L1 diabodies, imaging agents comprising a labeled anti-PD-L1 diabodies, methods of preparing the imaging agents (including anti-PD-L1 diabody agents), and methods of imaging and diagnosis using the imaging agents. The present application also provides methods for treating diseases or disorders by administering the anti-PD-L1 diabodies into individuals.

One aspect of this application provides an isolated anti-PD-L1 diabody comprising a first polypeptide and a second polypeptide, wherein the first polypeptide and the second polypeptide each comprises a heavy chain variable region ($V_H$) and a light chain variable region ($V_L$), wherein: a) the $V_H$ comprises an HC-CDR1 comprising the amino acid sequence of SEQ ID NO: 1, an HC-CDR2 comprising the amino acid sequence of SEQ ID NO: 6, and an HC-CDR3 comprising the amino acid sequence of any one of SEQ ID NO: 11, or a variant thereof comprising up to a total of about 5 amino acid substitutions in the HC-CDRs; and b) the $V_L$ comprises an LC-CDR1 comprising the amino acid sequence of SEQ ID NO: 14, an LC-CDR2 comprising the amino acid sequence of SEQ ID NO: 17, and an LC-CDR3 comprising the amino acid sequence of any one of SEQ ID NO: 20, or a variant thereof comprising up to a total of about 5 amino acid substitutions in the LC-CDRs. In some embodiments, the $V_H$ comprises an HC-CDR1 comprising the amino acid sequence of SEQ ID NO: 1, an HC-CDR2 comprising the amino acid sequence of SEQ ID NO: 6, and an HC-CDR3 comprising the amino acid sequence of SEQ ID NO: 11; and the $V_L$ comprises an LC-CDR1 comprising the amino acid sequence of SEQ ID NO: 14, an LC-CDR2 comprising the amino acid sequence of SEQ ID NO: 17, and an LC-CDR3 comprising the amino acid sequence of SEQ ID NO: 20. In some embodiments, a) the $V_H$ and the $V_L$ of the first polypeptide, b) the $V_H$ and the $V_L$ of the second polypeptide, c) the $V_H$ of the first polypeptide and the $V_L$ of the second polypeptide, or d) the $V_H$ of the second polypeptide and the $V_L$ of the first polypeptide form a binding domain that specifically binds to PD-L1. In some embodiments, the $V_H$ of the first polypeptide and the $V_L$ of the second polypeptide and the $V_H$ of the second polypeptide and the $V_L$ of the first polypeptide each form a binding domain that specifically binds to PD-L1.

Another aspect of this application provides an isolated anti-PD-L1 diabody comprising a first polypeptide and a second polypeptide, wherein the first polypeptide and the second polypeptide each comprises a heavy chain variable region ($V_H$) and a light chain variable region ($V_L$), and wherein a) the $V_H$ and the $V_L$ of the first polypeptide, b) the $V_H$ and the $V_L$ of the second polypeptide, c) the $V_H$ of the first polypeptide and the $V_L$ of the second polypeptide, or d) the $V_H$ of the second polypeptide and the $V_L$ of the first polypeptide form a binding domain that specifically binds to PD-L1 competitively with an anti-PD-L1 antibody comprising a second heavy chain variable region ($V_{H-2}$) and a second light chain variable region ($V_{L-2}$), wherein: a) the $V_{H-2}$ comprises an HC-CDR1 comprising the amino acid sequence of SEQ ID NO: 1, an HC-CDR2 comprising the amino acid sequence of SEQ ID NO: 6, and an HC-CDR3 comprising the amino acid sequence of SEQ ID NO: 11; and b) the $V_{L-2}$ comprises an LC-CDR1 comprising the amino acid sequence of SEQ ID NO: 14, an LC-CDR2 comprising the amino acid sequence of SEQ ID NO: 17, and an LC-CDR3 comprising the amino acid sequence of SEQ ID NO: 20.

Another aspect of this application provides an isolated anti-PD-L1 diabody comprising a first polypeptide and a second polypeptide, wherein the first polypeptide and the second polypeptide each comprises a heavy chain variable region ($V_H$) and a light chain variable region ($V_L$), wherein: a) the $V_H$ comprises a HC-CDR1, a HC-CDR2, and a HC-CDR3, respectively comprising the amino acid sequences of a CDR1, a CDR2, and a CDR3 within a second heavy chain variable region ($V_{H-2}$) having the sequence set forth in any of SEQ ID NOs: 22-24; and b) the $V_L$ comprises a LC-CDR1, a LC-CDR2, and a LC-CDR3, respectively comprising the amino acid sequences of a CDR1, a CDR2, and a CDR3 within a second light chain variable region ($V_{L-2}$) having the sequence set forth in any of SEQ ID NOs: 25-27.

In some embodiments according to any of the diabodies described above, the first polypeptide and the second polypeptide are linked via a covalent bond. In some embodiments, the covalent bond comprises a covalent bond between the $V_H$ of the first polypeptide and the $V_L$ of the second polypeptide, and/or a covalent bond is between the $V_L$ of the first polypeptide and the $V_H$ of the second polypeptide. In some embodiments, the covalent bond comprises a disulfide bond. In some embodiments, the disulfide bond or one of the at least two disulfide bonds is formed by a) a cysteine residue in a HC-FR2 of the first polypeptide and a cysteine residue in a LC-FR4 of the second polypeptide, and/or b) a cysteine residue in a LC-FR4 of the first polypeptide and a cysteine residue in a HC-FR2 of the second polypeptide.

In some embodiments according to any of the diabodies described above, the first polypeptide and the second polypeptide are linked via two or more covalent bonds. In some embodiments, the two or more covalent bonds comprise a) a first covalent bond between the $V_H$ of the first polypeptide and the $V_L$ of the second polypeptide; and b) a second covalent bond between the $V_H$ of the first polypeptide and the $V_L$ of the second polypeptide. In some embodiments, the covalent bond comprises a disulfide bond. In some embodiments, the two or more covalent bonds comprise at least two disulfide bonds. In some embodiments, the at least two disulfide bonds comprise a) a first disulfide bond between the $V_H$ of the first polypeptide and the $V_L$ of the second polypeptide; and b) a second disulfide bond between the $V_H$ of the first polypeptide and the $V_L$ of the second polypeptide. In some embodiments, the disulfide bond or one of the at least two disulfide bonds is formed by a) a cysteine residue in a HC-FR2 of the first polypeptide and a cysteine residue in a LC-FR4 of the second polypeptide, and/or b) a cysteine residue in a LC-FR4 of the first polypeptide and a cysteine residue in a HC-FR2 of the second polypeptide.

In some embodiments according to any of the diabodies described above, the $V_H$ in the first polypeptide and/or the second polypeptide comprises a G44C mutation and/or a Q105C mutation according to the Kabat numbering system.

In some embodiments according to any of the diabodies described above, the $V_L$ in the first polypeptide and/or the second polypeptide comprises a Q100C mutation and/or an A43C mutation according to the Kabat numbering system.

In some embodiments according to any of the diabodies described above, the $V_H$ in the first polypeptide and the second polypeptide each comprises a G44C mutation, and the $V_L$ in the first polypeptide and the second polypeptide each comprises a Q100C mutation, wherein the G44C in the $V_H$ of the first polypeptide and the Q100C in the $V_L$ of the second polypeptide form a first disulfide bond, and wherein the Q100C in the $V_L$ of the first polypeptide and the G44C in the $V_H$ of the second polypeptide form a second disulfide bond.

In some embodiments according to any of the diabodies described above, the $V_H$ in the first polypeptide and the second polypeptide each comprises a Q105C mutation, and wherein the $V_L$ in the first polypeptide and the second polypeptide each comprises an A43C mutation.

In some embodiments according to any of the diabodies described above, the $V_H$ and the $V_L$ of the first polypeptide are fused to each other via a peptide linker. In some embodiments according to any of the diabodies described above, the $V_H$ and the $V_L$ of the second polypeptide are fused to each other via a peptide linker. In some embodiments, the peptide linker has a length of about one to thirty amino acids. In some embodiments, the peptide linker comprises the amino acid sequence of any one of SEQ ID NOs: 28-34.

In some embodiments according to any of the diabodies described above, the first polypeptide or the second polypeptide further comprises a signal peptide fused to the N-terminal of the polypeptide. In some embodiments, the signal peptide comprises the amino acid sequence of SEQ ID NO: 35.

In some embodiments according to any of the diabodies described above, the $V_H$ of the first and/or second polypeptide comprises the amino acid sequence of any one of SEQ ID NOs: 22-24.

In some embodiments according to any of the diabodies described above, the $V_L$ of the first and/or second polypeptide comprises the amino acid sequence of any one of SEQ ID NOs: 25-27.

In some embodiments according to any of the diabodies described above, the first polypeptide and/or the second polypeptide further comprises a tag. In some embodiments, the tag is fused to the C-terminal of the first polypeptide and/or the second polypeptide. In some embodiments, the tag comprises a His-tag. In some embodiments, the tag is fused to the polypeptide via a second linker. In some embodiments, the second linker has a length of about four to fifteen amino acids. In some embodiments, the second linker comprises an amino acid sequence of GGGGS (SEQ ID NO: 56).

In some embodiments according to any of the diabodies described above, the first polypeptide and/or the second polypeptide comprises the amino acid sequence of any one of SEQ ID NOs: 36-43.

Another aspect of this application provides a pharmaceutical composition comprising any of the diabodies described above, and a pharmaceutical acceptable carrier.

Another aspect of this application provides a polynucleotide (e.g., a single polynucleotide or multiple polypeptides) encoding any of the diabodies described above.

Another aspect of this application provides a nucleic acid construct, comprising any of the polynucleotides described above, optionally further comprising a promoter in operative connection with the polynucleotide.

Another aspect of this application provides a vector comprising any of the nucleic acid constructs described above.

Another aspect of this application provides an isolated host cell comprising any of the polynucleotides described above, any of the nucleic acid constructs described above, or any of the vectors described above.

Another aspect of this application provides a culture medium comprising any of the diabodies described above, any of the polynucleotides described above, any of the nucleic acid constructs described above, any of the vectors described above, or any of the host cells described above.

Another aspect of this application provides a method of producing an anti-PD-L1 diabody, comprising: a) culturing any of the isolated host cells described above under conditions effective to express the diabody; and b) obtaining the expressed diabody from the host cell.

Another aspect of this application provides a method of determining the distribution of PD-L1 in an individual, comprising: a) administering to the individual an imaging agent comprising any of the diabodies described above labeled with a labeling agent (such as radionuclide); and b) imaging the imaging agent in the individual with a non-invasive imaging technique.

Another aspect of this application provides a method of diagnosing an individual having a disease or condition, comprising: a) determining the distribution of PD-L1 in the individual using any of the methods of determining the distribution of PD-L1 in an individual described above; and b) diagnosing the individual as positive for PD-L1 if signal of the imaging agent is detected at a tissue of interest, or diagnosing the individual as negative for PD-L1 if signal of the imaging agent is not detected at a tissue of interest.

Another aspect of this application provides a method of treating an individual having a disease or condition, comprising: a) diagnosing the individual using any of the methods of diagnosing an individual described above; and b) administering to the individual an effective amount of a therapeutic agent targeting PD-L1, if the individual is diagnosed as positive for PD-L1.

Another aspect of this application provides a method of treating an individual having a disease or condition, comprising administering to the individual an effective amount of any of the diabodies described above or any of the pharmaceutical compositions described above.

Another aspect of this application provides an imaging agent comprising any of the diabodies described above labeled with a radionuclide.

Another aspect of this application provides a method of preparing an imaging agent targeting PD-L1, comprising: a) conjugating a label with any of the anti-PD-L1 diabodies described above, thereby providing the imaging agent. In some embodiments, there is provided a method of preparing an imaging agent targeting PD-L1, comprising: a) conjugating a chelating compound to any of the diabodies described above to provide an anti-PD-L1 diabody conjugate; b) contacting a radionuclide with the anti-PD-L1 diabody conjugate, thereby providing the imaging agent.

Another aspect of this application provides a kit comprising: a) any of the diabodies described above; and b) a chelating agent. In some embodiments, the kit further comprises a radionuclide.

Another aspect of this application provides a method of determining the distribution of PD-L1 in an individual, comprising: administering to the individual an effective amount of an imaging agent comprising any of the diabodies described above and a labeling agent; and imaging the imaging agent in the individual with a non-invasive imaging technique. In some embodiments, there is provided a method of determining the distribution of PD-L1 in an individual, comprising: administering to the individual an effective amount of an diabody agent comprising any of the diabodies described above and a first conjugation moiety; subsequently administering to the individual an effective amount of a radionuclide compound comprising a radionuclide and a second conjugation moiety, wherein the first conjugation moiety and the second conjugation moiety is conjugated to each other in vivo to provide an imaging agent; and imaging the imaging agent in the individual with a non-invasive imaging technique. In some embodiments, the first conjugation moiety and the second conjugation moiety each comprises a member of a click chemistry pair, and are conjugated to each other via click chemistry.

DETAILED DESCRIPTION OF THE INVENTION

Figure 1:
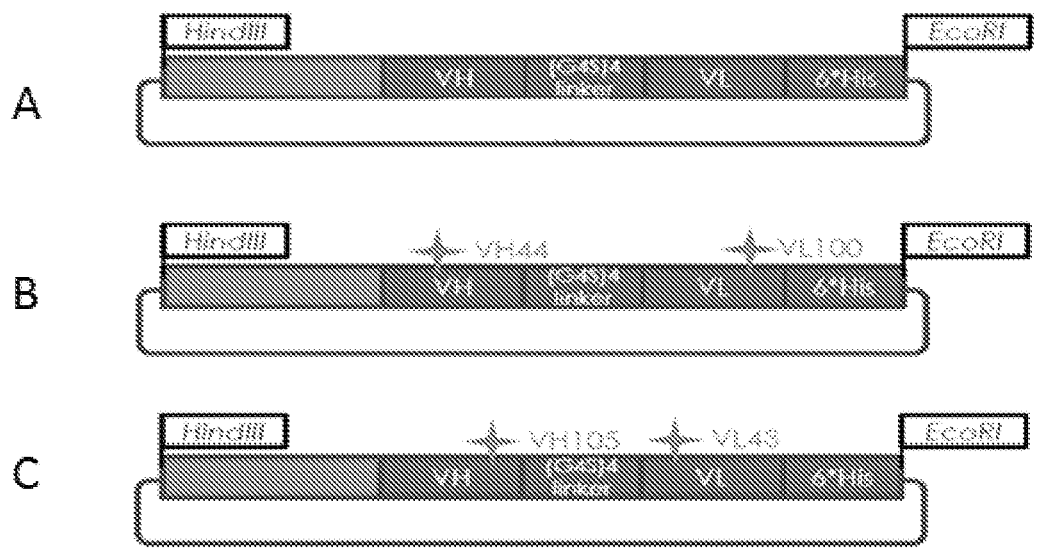
FIG. 1 shows a schematic diagram of the construct designs of exemplary anti-PD-L1 scFvs.

The present application provides anti-PD-L1 diabodies, anti-PD-L1 diabody agents, imaging agents, methods for detection of PD-L1 in an individual and methods for treating a disease or disorder. The diabodies described herein provide high binding affinity to target PD-L1 and, when incorporated into an imaging agent, provide a high sensitivity for detection and effective targeting and penetration into target tissues. Distribution and expression levels of PD-L1 can be determined by in vivo live imaging of an individual administered with the imaging agent.

One aspect of the present application provides anti-PD-L1 diabodies. In some embodiments, the diabodies comprises a first polypeptide and a second polypeptide, wherein the first polypeptide and the second polypeptide each comprises a heavy chain variable region ($V_H$) and a light chain variable region ($V_L$), wherein: a) the $V_H$ comprises an HC-CDR1 comprising the amino acid sequence of SEQ ID NO: 1, an HC-CDR2 comprising the amino acid sequence of SEQ ID NO: 6, and an HC-CDR3 comprising the amino acid sequence of SEQ ID NO: 11; and b) the $V_L$ comprises an LC-CDR1 comprising the amino acid sequence of SEQ ID NO: 14, an LC-CDR2 comprising the amino acid sequence of SEQ ID NO: 17, and an LC-CDR3 comprising the amino acid sequence of SEQ ID NO: 20. In some embodiments, the first polypeptide and the second polypeptide are linked via at least two disulfide bonds. In some embodiments, the $V_H$ in the first polypeptide and the second polypeptide each comprises a G44C mutation, and the $V_L$ in the first polypeptide and the second polypeptide each comprises a Q100C mutation, wherein the G44C in the $V_H$ of the first polypeptide and the Q100C in the $V_L$ of the second polypeptide form a first disulfide bond, and wherein the Q100C in the $V_L$ of the first polypeptide and the G44C in the $V_H$ of the second polypeptide form a second disulfide bond.

Another aspect of the present application provides an imaging agent comprising an anti-PD-L1 diabody labeled with a radionuclide.

Another aspect of the present application provides methods of determining the distribution of PD-L1 in an individual, comprising: a) administering to the individual an imaging agent comprising an anti-PD-L1 diabody labeled with a radionuclide; and b) imaging the imaging agent in the individual with a non-invasive imaging technique. Another aspect of the present application provides methods of diagnosing an individual having a disease or condition, comprising: a) determining the distribution of PD-L1 in the individual using the method described above; and b) diagnosing the individual as positive for PD-L1 if signal of the imaging agent is detected at a tissue of interest, or diagnosing the individual as negative for PD-L1 if signal of the imaging agent is not detected at a tissue of interest.

Also provided are compositions, kits and articles of manufacture comprising the imaging agents and anti-PD-L1 diabody or diabody agents described herein, methods of making thereof, and methods of treating an individual having a disease or condition (such as cancer, infectious disease, autoimmune disease or metabolic disease).

I. Definitions

The term "antibody" is used in its broadest sense and encompasses various antibody structures, including but not limited to monoclonal antibodies, polyclonal antibodies, multispecific antibodies (e.g., bispecific antibodies), full-length antibodies and antigen-binding fragments thereof, so long as they exhibit the desired antigen-binding activity.

"Fv" is the minimum antibody fragment which contains a complete antigen-recognition and -binding site. This fragment consists of a dimer of one heavy- and one light-chain variable region domain in tight, non-covalent association.

From the folding of these two domains emanate six hypervariable loops (3 loops each from the heavy and light chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv," also abbreviated as "sFv" or "scFv," are antibody fragments that comprise the $V_H$ and $V_L$ antibody domains connected into a single polypeptide chain. In some embodiments, the scFv polypeptide further comprises a polypeptide linker between the $V_H$ and $V_L$ domains which enables the scFv to form the desired structure for antigen binding. For a review of scFv, see Plückthun in The Pharmacology of Monoclonal Antibodies, vol. 113, Rosenburg and Moore eds., Springer-Verlag, New York, pp. 269-315 (1994).

"Diabody" or "diabodies" described herein refer to a complex comprising two scFv polypeptides. In some embodiments, inter-chain but not intra-chain pairing of the $V_H$ and $V_L$ domains is achieved, resulting in a bivalent fragment, i.e., fragment having two antigen-binding sites.

As used herein, the term "CDR" or "complementarity determining region" is intended to mean the non-contiguous antigen combining sites found within the variable region of both heavy and light chain polypeptides. These particular regions have been described by Kabat et al., J. Biol. Chem. 252:6609-6616 (1977); Kabat et al., U.S. Dept. of Health and Human Services, "Sequences of proteins of immunological interest" (1991); Chothia et al., J. Mol. Biol. 196: 901-917 (1987); Al-Lazikani B. et al., J. Mol. Biol., 273: 927-948 (1997); MacCallum et al., J. Mol. Biol. 262:732-745 (1996); Abhinandan and Martin, Mol. Immunol., 45:3832-3839 (2008); Lefranc M. P. et al., Dev. Comp. Immunol., 27:55-77 (2003); and Honegger and Plückthun, J. Mol. Biol., 309:657-670 (2001), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison. CDR prediction algorithms and interfaces are known in the art, including, for example, Abhinandan and Martin, Mol. Immunol., 45:3832-3839 (2008); Ehrenmann F. et al., Nucleic Acids Res., 38: D301-D307 (2010); and Adolf-Bryfogle J. et al., Nucleic Acids Res., 43: D432-D438 (2015). The contents of the references cited in this paragraph are incorporated herein by reference in their entireties for use in the present invention and for possible inclusion in one or more claims herein.

TABLE 1

CDR DEFINITIONS

| | Kabat[1] | Chothia[2] | MacCallum[3] | IMGT[4] | AHo[5] |
|---|---|---|---|---|---|
| $V_H$ CDR1 | 31-35 | 26-32 | 30-35 | 27-38 | 25-40 |
| $V_H$ CDR2 | 50-65 | 53-55 | 47-58 | 56-65 | 58-77 |
| $V_H$ CDR3 | 95-102 | 96-101 | 93-101 | 105-117 | 109-137 |
| $V_L$ CDR1 | 24-34 | 26-32 | 30-36 | 27-38 | 25-40 |
| $V_L$ CDR2 | 50-56 | 50-52 | 46-55 | 56-65 | 58-77 |
| $V_L$ CDR3 | 89-97 | 91-96 | 89-96 | 105-117 | 109-137 |

[1]Residue numbering follows the nomenclature of Kabat et al., supra
[2]Residue numbering follows the nomenclature of Chothia et al., supra
[3]Residue numbering follows the nomenclature of MacCallum et al., supra
[4]Residue numbering follows the nomenclature of Lefranc et al., supra
[5]Residue numbering follows the nomenclature of Honegger and Plückthun, supra The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

Unless indicated otherwise herein, the numbering of the residues in an immunoglobulin heavy chain is that of the EU index as in Kabat et al., supra. The "EU index as in Kabat" refers to the residue numbering of the human IgGI EU antibody.

"Framework" or "FR" residues are those variable-domain residues other than the CDR residues as herein defined. FR sequences FR1, FR2, FR3, and FR4 in heavy chain or light chain are defined by general formula: FR1-CDR1-FR2-CDR2-FR3-CDR3-FR4.

The term "semi-synthetic" in reference to an antibody or diabody means that the antibody or diabody has one or more naturally occurring sequences and one or more non-naturally occurring (i.e., synthetic) sequences.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region (HVR) of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

"Percent (%) amino acid sequence identity" or "homology" with respect to the polypeptide and antibody sequences identified herein is defined as the percentage of amino acid residues in a candidate sequence that are identical with the amino acid residues in the polypeptide being compared, after aligning the sequences considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, Megalign (DNASTAR), or MUSCLE software. Those skilled in the art can determine appropriate parameters for measuring alignment, including any algorithms needed to achieve maximal alignment over the full-length of the sequences being compared. For purposes herein, however, % amino acid sequence identity values are generated using the sequence comparison computer program MUSCLE (Edgar, R. C., Nucleic Acids Research 32 (5): 1792-1797, 2004; Edgar, R. C., BMC Bioinformatics 5 (1): 113, 2004).

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared times 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The "light chains" of antibodies (immunoglobulins) from any mammalian species can be assigned to one of two clearly distinct types, called kappa ("κ") and lambda ("λ"), based on the amino acid sequences of their constant domains.

The term "epitope" as used herein refers to the specific group of atoms or amino acids on an antigen to which an antibody or diabody binds. Two antibodies or antibody moieties may bind the same epitope within an antigen if they exhibit competitive binding for the antigen.

As used herein, a first antibody (such as diabody) "competes" for binding to a target antigen with a second antibody (such as diabody) when the first antibody inhibits the target antigen binding of the second antibody by at least about 50% (such as at least about any one of 55%, 60%, 65%, 70%, 75%, 80%, 85%, 90%, 95%, 98% or 99%) in the presence of an equimolar concentration of the first antibody, or vice versa. A high throughput process for "binning" antibodies based upon their cross-competition is described in PCT Publication No. WO 03/48731.

As use herein, the terms "specifically binds," "specifically recognizing," and "is specific for" refer to measurable and reproducible interactions, such as binding between a target and an antibody (such as a diabody), which is determinative of the presence of the target in the presence of a heterogeneous population of molecules, including biological molecules. For example, an antibody that specifically recognizes a target (which can be an epitope) is an antibody (such as a diabody) that binds this target with greater affinity, avidity, more readily, and/or with greater duration than its bindings to other targets. In some embodiments, the extent of binding of an antibody to an unrelated target is less than about 10% of the binding of the antibody to the target as measured, e.g., by a radioimmunoassay (RIA). In some embodiments, an antibody that specifically binds a target has a dissociation constant (KD) of ≤10-5 M, ≤10-6 M, ≤10-7 M, ≤10-8 M, ≤10-9 M, ≤10-10 M, ≤10-11 M, or ≤10-12 M. In some embodiments, an antibody specifically binds an epitope on a protein that is conserved among the protein from different species. In some embodiments, specific binding can include, but does not require exclusive binding. Binding specificity of the antibody or antigen-binding domain can be determined experimentally by methods known in the art. Such methods comprise, but are not limited to Western blots, ELISA-, RIA-, ECL-, IRMA-, EIA-, BIACORE™-tests and peptide scans.

An "isolated" antibody (or construct) is one that has been identified, separated and/or recovered from a component of its production environment (e.g., natural or recombinant). Preferably, the isolated polypeptide is free of association with all other components from its production environment.

An "isolated" nucleic acid molecule encoding a construct or antibody (such as diabody) described herein is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies described herein is in a form other than in the form or setting in which it is found in nature. Isolated nucleic acid molecules therefore are distinguished from nucleic acid encoding the polypeptides and antibodies described herein existing naturally in cells. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As used herein, "treatment" or "treating" is an approach for obtaining beneficial or desired results, including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing or improving the quality of life, increasing weight gain, and/or prolonging survival. Also encompassed by "treatment" is a reduction of pathological consequence of cancer (such as, for example, tumor volume). The methods of the invention contemplate any one or more of these aspects of treatment.

The term "effective amount" refers to the amount of an agent that is sufficient to effect beneficial or desired results. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

The terms "subject," "individual," and "patient" are used interchangeably herein to refer to a mammal, including, but not limited to, human, bovine, horse, feline, canine, rodent, or primate. In some embodiments, the individual is a human.

It is understood that embodiments of the invention described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancer of types other than X.

The term "about X-Y" used herein has the same meaning as "about X to about Y."

The term "about X, Y or Z" used herein has the same meaning as "about X, about Y, or about Z."

As used herein and in the appended claims, the singular forms "a," "or," and "the" include plural referents unless the context clearly dictates otherwise.

"Conjugated" used herein refers to specific association of two conjugation moieties, which can be covalent or non-covalent.

II. Anti-PD-L1-Diabodies

One aspect of the present application provides an isolated anti-PD-L1 diabody and an anti-PD-L1 diabody agent. In some embodiments, the diabody comprises a first polypeptide and a second polypeptide, wherein the first polypeptide and the second polypeptide each comprises a heavy chain variable region ($V_H$) and a light chain variable region ($V_L$), wherein: a) the $V_H$ comprises an HC-CDR1 comprising the amino acid sequence of any one of SEQ ID NOs: 1-5, an HC-CDR2 comprising the amino acid sequence of any one of SEQ ID NOs: 6-10, and an HC-CDR3 comprising the amino acid sequence of any one of SEQ ID NOs: 11-13, or a variant thereof comprising up to a total of about 3 amino acid substitutions in the HC-CDRs; and b) the $V_L$ comprises an LC-CDR1 comprising the amino acid sequence of any one of SEQ IDs NO: 14-16, an LC-CDR2 comprising the amino acid sequence of any one of SEQ ID NOs: 17-19, and an LC-CDR3 comprising the amino acid sequence of any one of SEQ ID NOs: 20-21, or a variant thereof comprising up to a total of about 3 amino acid substitutions in the LC-CDRs. In some embodiments, the first polypeptide and the second polypeptide are linked via at least two disulfide bonds. In some embodiments, the $V_H$ in the first polypeptide and the second polypeptide each comprises a G44C mutation, and the $V_L$ in the first polypeptide and the second polypeptide each comprises a Q100C mutation, wherein the G44C in the $V_H$ of the first polypeptide and the Q100C in the $V_L$ of the second polypeptide form a first disulfide bond, and wherein the Q100C in the $V_L$ of the first polypeptide and the G44C in the $V_H$ of the second polypeptide form a second disulfide bond. In some embodiments, a) the $V_H$ and the $V_L$ of the first polypeptide, b) the $V_H$ and the $V_L$ of the second polypeptide, c) the $V_H$ of the first polypeptide and the $V_L$ of the second polypeptide, or d) the $V_H$ of the second polypeptide and the $V_L$ of the first polypeptide form a binding domain that specifically binds to PD-L1. In some embodiments, the $V_H$ of the first polypeptide and the $V_L$ of the second polypeptide and the $V_H$ of the second polypeptide and the $V_L$ of the first polypeptide each form a binding domain that specifically binds to PD-L1.

In some embodiments, there is provided an isolated anti-PD-L1 diabody comprising a first polypeptide and a second polypeptide, wherein the first polypeptide and the second polypeptide each comprises a heavy chain variable region ($V_H$) and a light chain variable region ($V_L$), wherein: a) the $V_H$ comprises an HC-CDR1 comprising the amino acid sequence of any one of SEQ ID NOs: 1-5, an HC-CDR2 comprising the amino acid sequence of any one of SEQ ID NOs: 6-10, and an HC-CDR3 comprising the amino acid sequence of any one of SEQ ID NOs: 11-13, or a variant thereof comprising up to a total of about 5, 4, 3, 2, or 1 amino acid substitutions in the HC-CDRs; and b) the $V_L$ comprises an LC-CDR1 comprising the amino acid sequence of any one of SEQ IDs NO: 14-16, an LC-CDR2 comprising the amino acid sequence of any one of SEQ ID NOs: 17-19, and an LC-CDR3 comprising the amino acid sequence of any one of SEQ ID NOs: 20-21, or a variant thereof comprising up to a total of about 5, 4, 3, 2, or 1 amino acid substitutions in the LC-CDRs. In some embodiments, the substitutions consist of conservative substitutes (such as those disclosed in Table 2.) In some embodiments, the first polypeptide and the second polypeptide are linked via at least two disulfide bonds. In some embodiments, the at least two disulfide bonds are formed by a) a cysteine residue in a HC-FR2 of the first polypeptide and a cysteine residue in a LC-FR4 of the second polypeptide, and/or b) a cysteine residue in a LC-FR4 of the first polypeptide and a cysteine residue in a HC-FR2 of the second polypeptide. In some embodiments, the $V_H$ in the first polypeptide and the second polypeptide each comprises a G44C mutation, and the $V_L$ in the first polypeptide and the second polypeptide each comprises a Q100C mutation, wherein the G44C in the $V_H$ of the first polypeptide and the Q100C in the $V_L$ of the second polypeptide form a first disulfide bond, and wherein the Q100C in the $V_L$ of the first polypeptide and the G44C in the $V_H$ of the second polypeptide form a second disulfide bond. In some embodiments, the $V_H$ and the $V_L$ of the first polypeptide are fused to each other via a peptide linker. In some embodiments, the peptide linker between the $V_H$ and the $V_L$ of the first polypeptide or the second polypeptide has a length of about one to thirty amino acids (such as about 1-15 amino acids, or about 15-30 amino acids). In some embodiments, the peptide linker comprises the amino acid sequence of any one of SEQ ID NOs: 28-34. In some embodiments, the first polypeptide or the second polypeptide further comprises a signal peptide (such as the signal peptide comprising the amino acid sequence of SEQ ID NO: 35) fused to the N-terminal of the polypeptide. In some embodiments, the $V_H$ comprises the amino acid sequence of any one of SEQ ID NOs: 22-24, or a variant thereof having at least about 80% (such as at least about any one of 80%, 85%, 90%, 95%, 96%, 97%, 98%, or 99%) sequence identity to the amino acid sequence of any one of SEQ ID NO: 22-24. In some embodiments, the $V_L$ comprises the amino acid sequence of any one of SEQ ID NOs: 25-27, or a variant thereof having at least about 80% (such as at least about any one of 80%, 85%, 90%, 95%, 96%, 97%, 98%, or 99%) sequence identity to the amino acid sequence of any one of SEQ ID NO: 25-27. In some embodiments, a) the $V_H$ and the $V_L$ of the first polypeptide, b) the $V_H$ and the $V_L$ of the second polypeptide, c) the $V_H$ of the first polypeptide and the $V_L$ of the second polypeptide, or d) the $V_H$ of the second polypeptide and the $V_L$ of the first polypeptide form a binding domain that specifically binds to PD-L1. In some embodiments, the $V_H$ of the first polypeptide and the $V_L$ of the second polypeptide and the $V_H$ of the second polypeptide and the $V_L$ of the first polypeptide each form a binding domain that specifically binds to PD-L1.

In some embodiments, there is provided an isolated anti-PD-L1 diabody comprising a first polypeptide and a second polypeptide, wherein the first polypeptide and the second polypeptide each comprises a heavy chain variable region ($V_H$) and a light chain variable region ($V_L$), wherein: a) the $V_H$ comprises an HC-CDR1 comprising the amino acid sequence of SEQ ID NO: 1, an HC-CDR2 comprising the amino acid sequence of SEQ ID NO: 6, and an HC-CDR3 comprising the amino acid sequence of any one of SEQ ID NO: 11, or a variant thereof comprising up to a total of about 5, 4, 3, 2, or 1 amino acid substitutions in the HC-CDRs; and b) the $V_L$ comprises an LC-CDR1 comprising the amino acid sequence of SEQ ID NO: 14, an LC-CDR2 comprising the amino acid sequence of SEQ ID NO: 17, and an LC-CDR3 comprising the amino acid sequence of any one of SEQ ID NO: 20, or a variant thereof comprising up to a total of about 5, 4, 3, 2, or 1 amino acid substitutions in the LC-CDRs. In some embodiments, the substitutions consist of conservative substitutes (such as disclosed in Table 2.) In some embodiments, the $V_H$ comprises an HC-CDR1 comprising the amino acid sequence of SEQ ID NO: 1, an HC-CDR2 comprising the amino acid sequence of SEQ ID NO: 6, and an HC-CDR3 comprising the amino acid sequence of SEQ ID NO: 11; and the $V_L$ comprises an LC-CDR1 comprising the amino acid sequence of SEQ ID NO: 14, an LC-CDR2 comprising the amino acid sequence of SEQ ID NO: 17, and an LC-CDR3 comprising the amino acid sequence of SEQ ID NO: 20. In some embodiments, the first polypeptide and the second polypeptide are linked via at least two disulfide bonds. In some embodiments, the at least two disulfide bonds are formed by a) a cysteine residue in a HC-FR2 of the first polypeptide and a cysteine residue in a LC-FR4 of the second polypeptide, and/or b) a cysteine residue in a LC-FR4 of the first polypeptide and a cysteine residue in a HC-FR2 of the second polypeptide. In some embodiments, the $V_H$ in the first polypeptide and the second polypeptide each comprises a G44C mutation, and the $V_L$ in the first polypeptide and the second polypeptide each comprises a Q100C mutation, wherein the G44C in the $V_H$ of the first polypeptide and the Q100C in the $V_L$ of the second polypeptide form a first disulfide bond, and wherein the Q100C in the $V_L$ of the first polypeptide and the G44C in the $V_H$ of the second polypeptide form a second disulfide bond. In some embodiments, the $V_H$ and the $V_L$ of the first polypeptide are fused to each other via a peptide linker. In some embodiments, the peptide linker between the $V_H$ and the $V_L$ of the first polypeptide or the second polypeptide has a length of about one to thirty amino acids (such as about 1-15 amino acids, or about 15-30 amino acids). In some embodiments, the peptide linker comprises the amino acid sequence of any one of SEQ ID NOs: 28-34. In some embodiments, the first polypeptide or the second polypeptide further comprises a signal peptide (such as the signal peptide comprising the amino acid sequence of SEQ ID NO: 35) fused to the N-terminal of the polypeptide. In some embodiments, the $V_H$ comprises the amino acid sequence of any one of SEQ ID NOs: 22-24, or a variant thereof having at least about 80% (such as at least about any one of 80%, 85%, 90%, 95%, 96%, 97%, 98%, or 99%) sequence identity to the amino acid sequence of any one of SEQ ID NO: 22-24. In some embodiments, the $V_L$ comprises the amino acid sequence of any one of SEQ ID NOs: 25-27, or a variant thereof having at least about 80% (such as at least about any one of 80%, 85%, 90%, 95%, 96%, 97%, 98%, or 99%) sequence identity to the amino acid sequence of any one of SEQ ID NO: 25-27. In some embodiments, a) the $V_H$ and the $V_L$ of the first polypeptide, b) the $V_H$ and the $V_L$ of the second polypeptide, c) the $V_H$ of the first polypeptide and the $V_L$ of the second polypeptide, or d) the $V_H$ of the second polypeptide and the $V_L$ of the first polypeptide form a binding domain that specifically binds to PD-L1. In some embodiments, the $V_H$ of the first polypeptide and the $V_L$ of the second polypeptide and the $V_H$ of the second polypeptide and the $V_L$ of the first polypeptide each form a binding domain that specifically binds to PD-L1.

In some embodiments, there is provided an isolated anti-PD-L1 diabody comprising a first polypeptide and a second polypeptide, wherein the first polypeptide and the second polypeptide each comprises a heavy chain variable region ($V_H$) and a light chain variable region ($V_L$), and wherein a) the $V_H$ and the $V_L$ of the first polypeptide, b) the $V_H$ and the $V_L$ of the second polypeptide, c) the $V_H$ of the first polypeptide and the $V_L$ of the second polypeptide, or d) the $V_H$ of the second polypeptide and the $V_L$ of the first polypeptide form a binding domain that specifically binds to PD-L1 competitively with an anti-PD-L1 antibody comprising a second heavy chain variable region ($V_{H\text{-}2}$) and a second light chain variable region ($V_{L\text{-}2}$), wherein: a) the $V_{H_2}$ comprises an HC-CDR1 comprising the amino acid sequence of SEQ ID NO: 1, an HC-CDR2 comprising the amino acid sequence of SEQ ID NO: 6, and an HC-CDR3 comprising the amino acid sequence of SEQ ID NO: 11; and b) the $V_{L_2}$ comprises an LC-CDR1 comprising the amino acid sequence of SEQ ID NO: 14, an LC-CDR2 comprising the amino acid sequence of SEQ ID NO: 17, and an LC-CDR3 comprising the amino acid sequence of SEQ ID NO: 20. In some embodiments, the binding domain is formed by the $V_H$ and the $V_L$ of the first polypeptide or the $V_H$ and the $V_L$ of the second polypeptide. In some embodiments, the binding domain is formed by the $V_H$ of the first polypeptide and the $V_L$ of the second polypeptide, or the $V_H$ of the second polypeptide and the $V_L$ of the first polypeptide. In some embodiments, the first polypeptide and the second polypeptide are linked via at least two disulfide bonds. In some embodiments, the at least two disulfide bonds are formed by a) a cysteine residue in a HC-FR2 of the first polypeptide and a cysteine residue in a LC-FR4 of the second polypeptide, and/or b) a cysteine residue in a LC-FR4 of the first polypeptide and a cysteine residue in a HC-FR2 of the second polypeptide. In some embodiments, the $V_H$ in the first polypeptide and the second polypeptide each comprises a G44C mutation, and the $V_L$ in the first polypeptide and the second polypeptide each comprises a Q100C mutation, wherein the G44C in the $V_H$ of the first polypeptide and the Q100C in the $V_L$ of the second polypeptide form a first disulfide bond, and wherein the Q100C in the $V_L$ of the first polypeptide and the G44C in the $V_H$ of the second polypeptide form a second disulfide bond. In some embodiments, the $V_H$ and the $V_L$ of the first polypeptide are fused to each other via a peptide linker. In some embodiments, the peptide linker between the $V_H$ and the $V_L$ of the first polypeptide or the second polypeptide has a length of about one to thirty amino acids (such as about 1-15 amino acids, or about 15-30 amino acids). In some embodiments, the peptide linker comprises the amino acid sequence of any one of SEQ ID NOs: 28-34. In some embodiments, the first polypeptide or the second polypeptide further comprises a signal peptide (such as the signal peptide comprising the amino acid sequence of SEQ ID NO: 35) fused to the N-terminal of the polypeptide. In some embodiments, the $V_H$ comprises the amino acid sequence of any one of SEQ ID NOs: 22-24, or a variant thereof having at least about 80% (such as at least about any one of 80%, 85%, 90%, 95%, 96%, 97%, 98%, or 99%) sequence identity to the amino acid sequence of any one of SEQ ID NO: 22-24. In some embodiments, the $V_L$ comprises the amino acid sequence of any one of SEQ ID NOs: 25-27, or a variant thereof having at least about 80% (such as at least about any one of 80%, 85%, 90%, 95%, 96%, 97%, 98%, or 99%) sequence identity to the amino acid sequence of any one of SEQ ID NO: 25-27.

In some embodiments, there is provided an isolated anti-PD-L1 diabody comprising a first polypeptide and a second polypeptide, wherein the first polypeptide and the second polypeptide each comprises a heavy chain variable region ($V_H$) and a light chain variable region ($V_L$), wherein: a) the $V_H$ comprises a HC-CDR1, a HC-CDR2, and a HC-CDR3, respectively comprising the amino acid sequences of a CDR1, a CDR2, and a CDR3 within a second heavy chain variable region ($V_{H\text{-}2}$) having the sequence set forth in any of SEQ ID NOs: 22-24; and b) the $V_L$ comprises a LC-CDR1, a LC-CDR2, and a LC-CDR3, respectively comprising the amino acid sequences of a CDR1, a CDR2, and a CDR3 within a second light chain variable region ($V_{L\text{-}2}$) having the sequence set forth in any of SEQ ID NOs: 25-27. In some embodiments, the first polypeptide and the second polypeptide are linked via at least two disulfide bonds. In some embodiments, the at least two disulfide bonds are formed by a) a cysteine residue in a HC-FR2 of the first polypeptide and a cysteine residue in a LC-FR4 of the second polypeptide, and/or b) a cysteine residue in a LC-FR4 of the first polypeptide and a cysteine residue in a HC-FR2 of the second polypeptide. In some embodiments, the $V_H$ in the first polypeptide and the second polypeptide each comprises a G44C mutation, and the $V_L$ in the first polypeptide and the second polypeptide each comprises a Q100C mutation, wherein the G44C in the $V_H$ of the first polypeptide and the Q100C in the $V_L$ of the second polypeptide form a first disulfide bond, and wherein the Q100C in the $V_L$ of the first polypeptide and the G44C in the $V_H$ of the second polypeptide form a second disulfide bond. In some embodiments, the $V_H$ and the $V_L$ of the first polypeptide are fused to each other via a peptide linker. In some embodiments, the peptide linker between the $V_H$ and the $V_L$ of the first polypeptide or the second polypeptide has a length of about one to thirty amino acids (such as about 1-15 amino acids, or about 15-30 amino acids). In some embodiments, the peptide linker comprises the amino acid sequence of any one of SEQ ID NOs: 28-34. In some embodiments, the first polypeptide or the second polypeptide further comprises a signal peptide (such as the signal peptide comprising the amino acid sequence of SEQ ID NO: 35) fused to the N-terminal of the polypeptide. In some embodiments, the $V_H$ comprises the amino acid sequence of any one of SEQ ID NOs: 22-24, or a variant thereof having at least about 80% (such as at least about any one of 80%, 85%, 90%, 95%, 96%, 97%, 98%, or 99%) sequence identity to the amino acid sequence of any one of SEQ ID NO: 22-24. In some embodiments, the $V_L$ comprises the amino acid sequence of any one of SEQ ID NOs: 25-27, or a variant thereof having at least about 80% (such as at least about any one of 80%, 85%, 90%, 95%, 96%, 97%, 98%, or 99%) sequence identity to the amino acid sequence of any one of SEQ ID NO: 25-27. In some embodiments, a) the $V_H$ and the $V_L$ of the first polypeptide, b) the $V_H$ and the $V_L$ of the second polypeptide, c) the $V_H$ of the first polypeptide and the $V_L$ of the second polypeptide, or d) the $V_H$ of the second polypeptide and the $V_L$ of the first polypeptide form a binding domain that specifically binds to PD-L1. In some embodiments, the $V_H$ of the first polypeptide and the $V_L$ of the second polypeptide and the $V_H$ of the second polypeptide and the $V_L$ of the first polypeptide each form a binding domain that specifically binds to PD-L1.

In some embodiments, the first polypeptide and the second polypeptide of the diabodies described herein are linked via a covalent bond. In some embodiments, the covalent bond comprises a covalent bond between the $V_H$ of the first polypeptide and the $V_L$ of the second polypeptide, and/or a covalent bond is between the $V_L$ of the first polypeptide and the $V_H$ of the second polypeptide. In some embodiments, the first polypeptide and the second polypeptide are linked via two or more covalent bonds. In some embodiments the two or more covalent bonds comprise a) a first covalent bond between the $V_H$ of the first polypeptide and the $V_L$ of the second polypeptide; and b) a second covalent bond between the $V_H$ of the first polypeptide and the $V_L$ of the second polypeptide. In some embodiments, the covalent bond comprises a disulfide bond. In some embodiments, the first polypeptide and the second polypeptide are linked via at least two disulfide bonds. In some embodiments, the at least two disulfide bonds comprise a) a first disulfide bond between the $V_H$ of the first polypeptide and the $V_L$ of the second polypeptide; and b) a second disulfide bond between the $V_H$ of the first polypeptide and the $V_L$ of the second polypeptide. In some embodiments, the disulfide bond or one of the at least two disulfide bonds is formed by a) a cysteine residue in a HC-FR2 of the first polypeptide and a cysteine residue in a LC-FR4 of the second polypeptide, and/or b) a cysteine residue in a LC-FR4 of the first polypeptide and a cysteine residue in a HC-FR2 of the second polypeptide.

In some embodiments, the $V_H$ in the first polypeptide and/or the second polypeptide comprises a G44C mutation or a Q105C mutation according to the Kabat numbering system. In some embodiments, the $V_L$ in the first polypeptide and/or the second polypeptide comprises a Q100C mutation or an A43C mutation according to the Kabat numbering system. In some embodiments, the $V_H$ in the first polypeptide and the second polypeptide each comprises a G44C mutation, and the $V_L$ in the first polypeptide and the second polypeptide each comprises a Q100C mutation, wherein the G44C in the $V_H$ of the first polypeptide and the Q100C in the $V_L$ of the second polypeptide form a first disulfide bond, and wherein the Q100C in the $V_L$ of the first polypeptide and the G44C in the $V_H$ of the second polypeptide form a second disulfide bond. In some embodiments, the $V_H$ in the first polypeptide and the second polypeptide each comprises a Q105C mutation, and wherein the $V_L$ in the first polypeptide and the second polypeptide each comprises an A43C mutation.

In some embodiments, the $V_H$ and the $V_L$ of the first polypeptide are fused to each other via a peptide linker. In some embodiments, the $V_H$ and the $V_L$ of the second polypeptide are fused to each other via a peptide linker. In some embodiments, the peptide linker between the $V_H$ and the $V_L$ of the first polypeptide or the second polypeptide has a length of about one to thirty amino acids. In some embodiments, the peptide linker has a length of no more than about 15 amino acids (such as no more than 15, 14, 13, 12, 11, 10 or 9 amino acids). In some embodiments, the peptide linker has a length of at least about 15 amino acids (such as at least about 15, 18, 20, 22, 25, or 27 amino acids). In some embodiments, the peptide linker has a length of about 1-5, 5-10, 10-15, 15-20, 20-25, 25-30 amino acids. In some embodiments, the peptide linker has a length of about 1-15, 2-12, 4-10 amino acids. In some embodiments, the peptide linker comprises the amino acid sequence of any one of SEQ ID NOs: 28-34.

In some embodiments, the first polypeptide or the second polypeptide further comprises a signal peptide fused to the N-terminal of the polypeptide. In some embodiments, the signal peptide comprises the amino acid sequence of SEQ ID NO: 35.

In some embodiments, the $V_H$ of the first and/or second polypeptides comprises the amino acid sequence of any one of SEQ ID NOs: 22-24, or a variant thereof having at least about 80% (such as at least about any one of 80%, 85%, 90%, 95%, 96%, 97%, 98%, or 99%) sequence identity to the amino acid sequence of any one of SEQ ID NO: 22-24.

In some embodiments, the $V_L$ of the first and/or second polypeptides comprises the amino acid sequence of any one of SEQ ID NOs: 25-27, or a variant thereof having at least about 80% (such as at least about any one of 80%, 85%, 90%, 95%, 96%, 97%, 98%, or 99%) sequence identity to the amino acid sequence of any one of SEQ ID NO: 25-27.

In some embodiments, the first polypeptide and/or the second polypeptide further comprise a tag. In some embodiments, the tag is fused to the C-terminal of the first polypeptide and/or the second polypeptide. In some embodiments, the tag is fused to the N-terminal of the first polypeptide and/or the second polypeptide. In some embodiments, the tag comprises a His-tag. In some embodiments, the tag is fused to the polypeptide via a second linker. In some embodiments, the second linker has a length of about one to thirty amino acids, such as about four to fifteen amino acids, about four to ten amino acids. In some embodiments, the second linker comprises an amino acid sequence of GGGGS (SEQ ID NO: 56).

In some embodiments, the first polypeptide and/or the second polypeptide comprises the amino acid sequence of any one of SEQ ID NOs: 36-43, or a variant thereof having at least about 80% (such as at least about any one of 80%, 85%, 90%, 95%, 96%, 97%, 98%, or 99%) sequence identity to the amino acid sequence of any one of SEQ ID NO: 36-43.

In some embodiments, the diabody is stable at acidic pH (e.g., at a pH lower than about 6.5, 6.0, 5.5, or 5.0). In some embodiments, the diabody has a melting temperature (Tm) of about 55-70° C. (such as about any one of 55-60, 60-65, or 65-70° C.).

In some embodiments, the diabody is humanized.

a) Substitution, Insertion, Deletion and Variants

In some embodiments, there is provided anti-PD-L1 diabody variant having one or more amino acid substitutions are provided. Sites of interest for substitutional mutagenesis include the HVRs (or CDRs) and FRs. Exemplary conservative substitutions are shown in Table 2 under the heading of "Preferred substitutions." More substantial changes are provided in Table 2 under the heading of "exemplary substitutions," and as further described below in reference to amino acid side chain classes. Amino acid substitutions may be introduced into a diabody of interest and the products screened for a desired activity, e.g., retained/improved antigen binding, decreased immunogenicity, or improved ADCC or CDC.

TABLE 2

Amino acid substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; and (6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized diabody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve diabody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant $V_H$ or $V_L$ being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001)). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any diabody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In some embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or CDRs.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. The method is applicable to diabodies as described herein. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

b) Glycosylation Variants

In some embodiments, the diabody is altered to increase or decrease the extent to which the construct is glycosylated. Addition or deletion of glycosylation sites to a diabody may be conveniently accomplished by altering the amino acid sequence such that one or more glycosylation sites is created or removed.

Native antibodies produced by mammalian cells typically comprise a branched, biantennary oligosaccharide that is generally attached by an N-linkage to Asn297 of the $C_H2$ domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in the diabody may be made in order to create antibody variants with certain improved properties.

In some embodiments, the diabody has a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87:614 (2004). Examples of cell lines capable of producing defucosylated antibodies include Lec13 CHO cells deficient in protein fucosylation (Ripka et al. *Arch. Biochem. Biophys.* 249:533-545 (1986); US Patent Application No. US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87:614 (2004); Kanda, Y. et al., *Biotechnol. Bioeng.*, 94 (4): 680-688 (2006); and WO2003/085107).

c) Diabody Derivatives

In some embodiments, the diabody described herein may be further modified to comprise additional nonproteinaceous moieties that are known in the art and readily available. The moieties suitable for derivatization of the diabodies include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the diabody may vary, and if more than one polymers are attached, they can be the same or different molecules. In general, the number and/or type of polymers used for derivatization can be determined based on considerations including, but not limited to, the particular properties or functions of the diabody to be improved, whether the diabody derivative will be used in diagnosis under defined conditions, etc.

In some embodiments, the diabodies may be further modified to comprise one or more biologically active protein, polypeptides or fragments thereof. "Bioactive" or "biologically active", as used herein interchangeably, means showing biological activity in the body to carry out a specific function. For example, it may mean the combination with a particular biomolecule such as protein, DNA, etc., and then promotion or inhibition of the activity of such biomolecule. In some embodiments, the bioactive protein or fragments thereof include proteins and polypeptides that are administered to patients as the active drug substance for prevention of or treatment of a disease or condition, as well as proteins and polypeptides that are used for diagnostic purposes, such as enzymes used in diagnostic tests or in vitro assays, as well as proteins and polypeptides that are administered to a patient to prevent a disease such as a vaccine.

III. Imaging Agents and Anti-PD-L1 Diabody Agents

One aspect of the present application provides an imaging agent comprising and an anti-PD-L1 diabody labeled with a labeling agent (e.g., a radionuclide). Any one of the imaging agents described in this section may be used in the methods of determining the distribution and/or expression level of PD-L1, or methods of diagnosis or treatment described herein.

In some embodiments, there is provided an imaging agent comprising an anti-PD-L1 diabody (such as any of the diabodies described herein) labeled with a radionuclide. In some embodiments, there is provided an imaging agent comprising an anti-PD-L1 diabody labeled with a radionuclide, wherein the diabody comprises a first polypeptide and a second polypeptide, wherein the first polypeptide and the second polypeptide each comprises a heavy chain variable region ($V_H$) and a light chain variable region ($V_L$), wherein: a) the $V_H$ comprises an HC-CDR1 comprising the amino acid sequence of SEQ ID NO: 1, an HC-CDR2 comprising the amino acid sequence of SEQ ID NO: 6, and an HC-CDR3 comprising the amino acid sequence of any one of SEQ ID NO: 11, or a variant thereof comprising up to a total of about 5 amino acid substitutions in the HC-CDRs; and b) the $V_L$ comprises an LC-CDR1 comprising the amino acid sequence of SEQ ID NO: 14, an LC-CDR2 comprising the amino acid sequence of SEQ ID NO: 17, and an LC-CDR3 comprising the amino acid sequence of any one of SEQ ID NO: 20, or a variant thereof comprising up to a total of about 5 amino acid substitutions in the LC-CDRs. In some embodiments, there is provided an imaging agent comprising an anti-PD-L1 diabody labeled with a radionuclide, wherein the diabody comprises a first polypeptide and a second polypeptide, wherein the first polypeptide and the second polypeptide each comprises a heavy chain variable region ($V_H$) and a light chain variable region ($V_L$), and wherein a) the $V_H$ and the $V_L$ of the first polypeptide, b) the $V_H$ and the $V_L$ of the second polypeptide, c) the $V_H$ of the first polypeptide and the $V_L$ of the second polypeptide, or d) the $V_H$ of the second polypeptide and the $V_L$ of the first polypeptide form a binding domain that specifically binds to PD-L1 competitively with an anti-PD-L1 antibody comprising a second heavy chain variable region ($V_{H-2}$) and a second light chain variable region ($V_{L-2}$), wherein: a) the $V_{H-2}$ comprises an HC-CDR1 comprising the amino acid sequence of SEQ ID NO: 1, an HC-CDR2 comprising the amino acid sequence of SEQ ID NO: 6, and an HC-CDR3 comprising the amino acid sequence of SEQ ID NO: 11; and b) the $V_{L-2}$ comprises an LC-CDR1 comprising the amino acid sequence of SEQ ID NO: 14, an LC-CDR2 comprising the amino acid sequence of SEQ ID NO: 17, and an LC-CDR3 comprising the amino acid sequence of SEQ ID NO: 20. In some embodiments, there is provided an imaging agent comprising an anti-PD-L1 diabody labeled with a radionuclide, wherein the diabody comprises a first polypeptide and a second polypeptide, wherein the first polypeptide and the second polypeptide each comprises a heavy chain variable region ($V_H$) and a light chain variable region ($V_L$), wherein: a) the $V_H$ comprises a HC-CDR1, a HC-CDR2, and a HC-CDR3, respectively comprising the amino acid sequences of a CDR1, a CDR2, and a CDR3 within a second heavy chain variable region ($V_{H-2}$) having the sequence set forth in any of SEQ ID NOs: 22-24; and b) the $V_L$ comprises a LC-CDR1, a LC-CDR2, and a LC-CDR3, respectively comprising the amino acid sequences of a CDR1, a CDR2, and a CDR3 within a second light chain variable region ($V_{L-2}$) having the sequence set forth in any of SEQ ID NOs: 25-27. In some embodiments, the $V_H$ in the first polypeptide and the second polypeptide each comprises a G44C mutation, and the $V_L$ in the first polypeptide and the second polypeptide each comprises a Q100C mutation, wherein the G44C in the $V_H$ of the first polypeptide and the Q100C in the $V_L$ of the second polypeptide form a first disulfide bond, and wherein the Q100C in the $V_L$ of the first polypeptide and the G44C in the $V_H$ of the second polypeptide form a second disulfide bond. In some embodiments, the radionuclide is selected from the group consisting of $^{64}Cu$, $^{18}F$, $^{67}Ga$, $^{68}Ga$, $^{111}In$, $^{177}Lu$, $^{90}Y$, $^{89}Zr$, $^{61}Cu$, $^{62}Cu$, $^{67}Cu$, $^{19}F$, $^{66}Ga$, $^{72}Ga$, $^{44}Sc$, $^{47}Sc$, $^{86}Y$, $^{88}Y$ and $^{45}Ti$. In some embodiments, the radionuclide is $^{68}Ga$. In some embodiments, the diabody is conjugated to a chelating compound that chelates the radionuclide. In some embodiments, the chelating compound is 1,4,7-triazacyclononane-1,4,7-trisacetic acid (NOTA), 1, 4, 7, 10-tetraazacyclododecane-1,4,7,10-tetraacetic acid (DOTA) or derivatives thereof. In some embodiments, the diabody cross-reacts with the PD-L1 from a non-human mammal (e.g., mouse, rat or monkey). In some embodiments, the diabody is humanized.

In some embodiments, there is provided an imaging agent comprising an anti-PD-L1 diabody (such as any of the diabodies described herein) conjugated to a chelating compound that chelates a radionuclide. In some embodiments, there is provided an imaging agent comprising an anti-PD-L1 diabody conjugated to a chelating compound that chelates a radionuclide, wherein the diabody comprises a first polypeptide and a second polypeptide, wherein the first polypeptide and the second polypeptide each comprises a heavy chain variable region ($V_H$) and a light chain variable region ($V_L$), wherein: a) the $V_H$ comprises an HC-CDR1 comprising the amino acid sequence of SEQ ID NO: 1, an HC-CDR2 comprising the amino acid sequence of SEQ ID NO: 6, and an HC-CDR3 comprising the amino acid sequence of any one of SEQ ID NO: 11, or a variant thereof comprising up to a total of about 5 amino acid substitutions in the HC-CDRs; and b) the $V_L$ comprises an LC-CDR1 comprising the amino acid sequence of SEQ ID NO: 14, an LC-CDR2 comprising the amino acid sequence of SEQ ID NO: 17, and an LC-CDR3 comprising the amino acid sequence of any one of SEQ ID NO: 20, or a variant thereof comprising up to a total of about 5 amino acid substitutions in the LC-CDRs. In some embodiments, there is provided an imaging agent comprising an anti-PD-L1 diabody conjugated to a chelating compound that chelates a radionuclide, wherein the diabody comprises a first polypeptide and a second polypeptide, wherein the first polypeptide and the second polypeptide each comprises a heavy chain variable region ($V_H$) and a light chain variable region ($V_L$), and wherein a) the $V_H$ and the $V_L$ of the first polypeptide, b) the $V_H$ and the $V_L$ of the second polypeptide, c) the $V_H$ of the first polypeptide and the $V_L$ of the second polypeptide, or d) the $V_H$ of the second polypeptide and the $V_L$ of the first polypeptide form a binding domain that specifically binds to PD-L1 competitively with an anti-PD-L1 antibody comprising a second heavy chain variable region ($V_{H-2}$) and a second light chain variable region ($V_{L-2}$), wherein: a) the $V_{H-2}$ comprises an HC-CDR1 comprising the amino acid sequence of SEQ ID NO: 1, an HC-CDR2 comprising the amino acid sequence of SEQ ID NO: 6, and an HC-CDR3 comprising the amino acid sequence of SEQ ID NO: 11; and b) the $V_{L-2}$ comprises an LC-CDR1 comprising the amino acid sequence of SEQ ID NO: 14, an LC-CDR2 comprising the amino acid sequence of SEQ ID NO: 17, and an LC-CDR3 comprising the amino acid sequence of SEQ ID NO: 20. In some embodiments, there is provided an imaging agent comprising an anti-PD-L1 diabody conjugated to a chelating compound that chelates a radionuclide, wherein the diabody comprises a first polypeptide and a second polypeptide, wherein the first polypeptide and the second polypeptide each comprises a heavy chain variable region ($V_H$) and a light chain variable region ($V_L$), wherein: a) the $V_H$ comprises a HC-CDR1, a HC-CDR2, and a HC-CDR3, respectively comprising the amino acid sequences of a CDR1, a CDR2, and a CDR3 within a second heavy chain variable region ($V_{H-2}$) having the sequence set forth in any of SEQ ID NOs: 22-24; and b) the $V_L$ comprises a LC-CDR1, a LC-CDR2, and a LC-CDR3, respectively comprising the amino acid sequences of a CDR1, a CDR2, and a CDR3 within a second light chain variable region ($V_{L-2}$) having the sequence set forth in any of SEQ ID NOs: 25-27. In some embodiments, the $V_H$ in the first polypeptide and the second polypeptide each comprises a G44C mutation, and the $V_L$ in the first polypeptide and the second polypeptide each comprises a Q100C mutation, wherein the G44C in the $V_H$ of the first polypeptide and the Q100C in the $V_L$ of the second polypeptide form a first disulfide bond, and wherein the Q100C in the $V_L$ of the first polypeptide and the G44C in the $V_H$ of the second polypeptide form a second disulfide bond. In some embodiments, the radionuclide is selected from the group consisting of $^{64}Cu$, $^{18}F$, $^{67}Ga$, $^{68}Ga$, $^{111}In$, $^{177}Lu$, $^{90}Y$, $^{89}Zr$, $^{61}Cu$, $^{62}Cu$, $^{67}Cu$, $^{19}F$, $^{66}Ga$, $^{72}Ga$, $^{44}Sc$, $^{47}Sc$, $^{86}Y$, $^{88}Y$ and $^{45}Ti$. In some embodiments, the radionuclide is $^{68}Ga$. In some embodiments, the chelating compound is NOTA, DOTA or derivatives thereof. In some embodiments, the diabody cross-reacts with the PD-L1 from a non-human mammal (e.g., mouse, rat or monkey). In some embodiments, the diabody is humanized.

Contemplated diabodies include, but are not limited to, humanized diabodies, partially humanized diabodies, fully humanized diabodies, semi-synthetic diabodies, and diabodies comprising the heavy chain and/or light chain CDRs discussed herein, e.g., in the "anti-PD-L1 diabodies" section.

In some embodiments, the diabody specifically recognizes the PD-L1 from human. In some embodiments, the diabody cross-reacts with the PD-L1 from two or more species. Cross-reactivity of the diabody with model animals and human facilities clinical studies of the imaging agent. In some embodiments, the diabody cross-reacts with the PD-L1 from a non-human animal, such as mammal. In some embodiments, the diabody cross-reacts with the PD-L1 from a rodent, such as mouse or rat. In some embodiments, the diabody cross-reacts with the PD-L1 from a non-human primate, such as a cynomolgus monkey.

Radionuclide

The imaging agents described herein comprise a labeling agent. For diagnostic purposes, the labeling agent may be a radionuclide, a radiological contrast agent, a paramagnetic ion, a metal, a fluorescent label, a chemiluminescent label, an ultrasound contrast agent and a photoactive agent. Such diagnostic labels are well known and any such known labels may be used.

In some embodiments, the imaging agent comprises a radionuclide. "Radionuclides" are often referred to as "radioactive isotopes" or "radioisotopes." Exemplary radionuclides or stable isotopes that may be attached to the antibody moieties described herein include, but are not limited to, $^{110}In$, $^{111}In$, $^{177}Lu$, $^{18}F$, $^{52}Fe$, $^{62}Cu$, $^{64}Cu$, $^{67}Cu$, $^{67}Ga$, $^{68}Ga$, $^{86}Y$, $^{90}Y$, $^{89}Zr$, $^{94m}Tc$, $^{94}Tc$, $^{99m}Tc$, $^{120}I$, $^{123}I$, $^{124}I$, $^{125}I$, $^{131}I$, $^{154-158}Gd$, $^{32}P$, $^{11}C$, $^{13}N$, $^{15}O$, $^{186}Re$, $^{188}Re$, $^{51}Mn$, $^{52m}Mn$, $^{55}Co$, $^{72}As$, $^{75}Br$, $^{76}Br$, $^{82m}Rb$, $^{83}Sr$, or other gamma-, beta-, or positron-emitters. In some embodiments, the radionuclide is selected from the group consisting of $^{64}Cu$, $^{18}F$, $^{67}Ga$, $^{68}Ga$, $^{111}In$, $^{177}Lu$, $^{90}Y$, $^{89}Zr$, $^{61}Cu$, $^{62}Cu$, $^{67}Cu$, $^{19}F$, $^{66}Ga$, $^{72}Ga$, $^{44}Sc$, $^{47}Sc$, $^{86}Y$, $^{88}Y$ and $^{45}Ti$. In some embodiments, the radionuclide is $^{68}Ga$.

Paramagnetic ions of use may include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). Metal contrast agents may include lanthanum (III), gold (III), lead (II) or bismuth (III). Radiopaque diagnostic agents may be selected from compounds, barium compounds, gallium compounds, and thallium compounds. A wide variety of fluorescent labels are known in the art, including but not limited to fluorescein isothiocyanate, rhodamine, phycoelytherin, phycocyanin, allophycocyanin, ophthaldehyde and fluorescamine. Chemiluminescent labels of use may include luminol, isoluminol, an aromatic acridinium ester, an imidazole, an acridinium salt or an oxalate ester.

Radioimmunodetection (RAID) has emerged as a clinically useful field over the last 35 years. Almost 1000 clinical trials using RAID have been conducted during this time, with some clear and important findings. The greater facility of this technique to detect lesions deemed "occult" by conventional imaging was recognized even in early studies and has repeatedly been confirmed by studies, regardless of antibody, tumor or radionuclide type.

Many radionuclides, such as $^{68}$Ga, $^{99}$Tc, $^{64}$Cu and $^{18}$F are good imaging agent of choice. They usually have a gamma or beta energy that is ideal for safe imaging, and are inexpensive and are readily available, being generator-produced and carrier-free. Their short half-life (less than 6 hours) readily lends themselves to coupling with antibody fragments for early imaging studies.

In some embodiments, the imaging agent comprises a chelating compound that chelates the radionuclide. In some embodiments, the chelating compound chelates a radioactive metal. In some embodiments, the chelating compound chelates a metal $^{18}$F. In some embodiments, the chelating compound is a hydrophilic chelating compound, which can bind metal ions and help to ensure rapid in vivo clearance. Suitable chelating compounds may be selected for their particular metal-binding properties, and substitution by known chemical cross-linking techniques or by use of chelators with side-chain reactive groups (such as bifunctional chelating compounds) may be performed with only routine experimentation.

Particularly useful metal-chelating compound combinations include 2-benzyl-DTPA (diethylenetriamine pentaacetic acid) and its monomethyl and cyclohexyl analogs, used with diagnostic isotopes in the general energy range of 60 to 4,000 keV, such as $^{125}$I, $^{131}$I, $^{123}$I, $^{124}$I, $^{62}$Cu, $^{64}$Cu, $^{18}$F, $^{111}$In, $^{67}$Ga, $^{68}$Ga, $^{99}$Tc, $^{94}$Tc, $^{11}$C, $^{13}$N, $^{15}$O, $^{76}$Br, for radio-imaging. The same chelating compounds, when complexed with nonradioactive metals, such as manganese, iron and gadolinium are useful for MRI. Macrocyclic chelating compounds such as NOTA (1,4,7-triazacyclononane-1,4,7-triacetic acid), DOTA (1,4,7,10-Tetraazacyclododecane-N,N',N'',N'''-tetraacetic acid), TETA (bromoacetamido-benzyl-tetraethylaminetetraacetic acid) and NETA ({4-[2-(bis-carboxymethyl-amino)-ethyl]-7-carboxymethyl-[1,4,7]triazonan-1-yl}-acetic acid) are of use with a variety of diagnostic radiometals, such as gallium, yttrium and copper. Such metal-chelating complexes can be made very stable by tailoring the ring size to the metal of interest. The person of ordinary skill will understand that, by varying the groups attached to a macrocyclic ring structure such as NOTA, the binding characteristics and affinity for different metals and/or radionuclides may change and such derivatives or analogs of, e.g. NOTA, may therefore be designed to bind any of the metals or radionuclides discussed herein.

DTPA and DOTA-type chelators, where the ligand includes hard base chelating functions such as carboxylate or amine groups, are most effective for chelating hard acid cations, especially Group IIa and Group IIIa metal cations. Such metal-chelate complexes can be made very stable by tailoring the ring size to the metal of interest. Other ring-type chelators such as macrocyclic polyethers are of interest for stably binding nuclides. Porphyrin chelators may be used with numerous metal complexes. More than one type of chelator may be conjugated to a peptide to bind multiple metal ions. Chelators such as those disclosed in U.S. Pat. No. 5,753,206, especially thiosemicarbazonylglyoxylcysteine (Tscg-Cys) and thiosemicarbazinyl-acetylcysteine (Tsca-Cys) chelators are advantageously used to bind soft acid cations of Tc, Re, Bi and other transition metals, lanthanides and actinides that are tightly bound to soft base ligands. Other hard acid chelators such as DOTA, TETA and the like can be substituted for the DTPA and/or TscgCys groups.

In some embodiments, the chelating compound comprises a functional group that can be conjugated to the anti-PD-L1 diabody. In some embodiments, the chelating compound comprises a functional group that is reactive with a primary amine (—NH$_2$) group in the anti-PD-L1 diabody. Primary amines exist at the N-terminus of each polypeptide chain and in the side-chain of lysine (Lys) amino acid residues. Exemplary functional groups that can be conjugated to a primary amine, e.g., a lysine side chain, of the anti-PD-L1 diabody, include, but are not limited to, isothiocyanates, isocyanates, acyl azides, N-hydroxysuccinimide (NHS) esters, sulfonyl chlorides, aldehydes, glyoxals, epoxides, oxiranes, carbonates, aryl halides, imidoesters, carbodiimides, anhydrides, and fluorophenyl esters. Most of these functional groups conjugate to amines by either acylation or alkylation.

In some embodiments, the chelating compound comprises a functional group that is reactive with a cysteine side chain (i.e., sulfhydryl group) in the anti-PD-L1 diabody. Exemplary sulfhydryl reactive groups include, but are not limited to, haloacetyls, maleimides, aziridines, acryloyls, arylating agents, vinylsulfones, pyridyl disulfides, TNB-thiols and disulfide reducing agents. Most of these groups conjugate to sulfhydryls by either alkylation (usually the formation of a thioether bond) or disulfide exchange (formation of a disulfide bond).

In some embodiments, the chelating compound is NOTA, including NOTA derivatives. Exemplary NOTA compounds with functional groups suitable for conjugation to antibody moieties, e.g., via amino acid side chains such as lysines and cysteines, are shown in FIG. 10. In some embodiments, the imaging agent comprises NOTA conjugated to the anti-PD-L1 diabody. In some embodiments, the NOTA compound comprises an isothiocyanate (—SCN) group. In some embodiments, the NOTA compound is p-SCN-Bn-NOTA. In some embodiments, the chelating compound comprises a NOTA conjugated to a lysine residue in the anti-PD-L1 diabody, and the NOTA chelates $^{68}$Ga. In some embodiments, the NOTA compound is first labeled with a radioactive metal, such as $^{68}$Ga, or $^{18}$F-metal, and then conjugated to the anti-PD-L1 diabody.

Anti-PD-L1 Diabody Agent

In some embodiments, there is provided an anti-PD-L1 diabody agent comprising an anti-PD-L1 diabody as described in Section II. In some embodiment, the anti-PD-L1 diabody further comprises a first conjugation moiety as described below.

Conjugation Moiety

One aspect of the present application provides conjugation moieties that can be incorporated in the diabody and/or the labeling agent (e.g., the radionuclide). In some embodiments, the conjugation moiety incorporated in the diabody agent (e.g., a first conjugation moiety) is capable of being conjugated to the conjugation moiety (e.g., a second conjugation moiety) incorporated in the labeling agent (e.g., radionuclide compound) in vivo.

In some embodiments the conjugation of the first conjugation moiety and second conjugation moiety is non-covalent. In some embodiments, the conjugation of the first conjugation moiety and second conjugation moiety is covalent.

In some embodiments, the first conjugation moiety and/or the second conjugation moiety each comprises a nucleic acid which are complementary to each other. In some embodiments, the nucleic acid is a DNA. In some embodiments, the first conjugation moiety and the second conjugation moiety are conjugated to each other via DNA-DNA hybridization.

In some embodiments, the first conjugation moiety and the second conjugation moiety are conjugated via a covalent bond between the two conjugation moieties. In some embodiments, the first conjugation moiety or the second conjugation moiety comprises a cysteine residue, a lysine residue, or a tyrosine residue. In some embodiments, the first conjugation moiety and the second conjugation moiety are conjugated based upon a coupling of cysteine residues (e.g., via a disulfide bond).

In some embodiments, the first conjugation moiety and the second conjugation moiety are conjugated based upon an antibody-drug conjugate.

Click Chemistry

In some embodiments, the first conjugation moiety and the second conjugation moiety each comprises a member of a click chemistry pair, and are conjugated to each other via click chemistry. The click chemistry pair described herein is two chemical moieties that are capable of exclusively reacting with each other via click chemistry.

In some embodiments, the click chemistry pair is selected from the group consisting of an azide-alkyne pair, an alkyne-nitrone pair, an alkene and tetrazole pair, and an isonitrile (e.g., isocyanide) and tetrazine pair.

In some embodiments, the click chemistry is based upon an azide-alkyne Huisgen cycloaddition. In some embodiments, the azide-alkyne Huisgen cycloaddition is copper catalyzed. In some embodiments, the azide-alkyne Huisgen cycloaddition is copper-free. In some embodiments, the conjugation moiety comprises a cyclic derivative of the alkynyl group. In some embodiments, the cyclic derivative of the alkynyl group is selected from cyclooctyne, difluorinated cyclooctyne, and dibenzocyclooctyne. In some embodiments, the click chemistry is based upon strain promoted Huisgen cycloaddition of azides. In some embodiments, the click chemistry is based upon reaction of strained alkenes.

In some embodiments, the click chemistry is based upon Staudinger-Bertozzi ligation, wherein the click chemistry involved a coupling reaction between an azide and a phosphine.

In some embodiments, the click chemistry is based upon an inverse-electron-demand Diels-Alder cycloaddition, wherein the click chemistry involves a coupling reaction between a strained alkene and a tetrazine. In some embodiments, a conjugation moiety comprises or is a trans-cyclooctene (TCO) or a tetrazine (Tz). In some embodiments, the first conjugation moiety comprises or is a trans-cyclooctene (TCO) and the second conjugation moiety comprises or is a tetrazine (Tz). In some embodiments, the first conjugation moiety comprises or is a Tz and the second conjugation moiety comprises or is a TCO. In some embodiments, the Tz is 6-Methyl-substituted tetrazine (6-Me tetrazine). In some embodiments, the Tz is 6-hydrogen-substituted tetrazine (6-H tetrazine).

In some embodiments, the conjugation moiety (e.g., tetrazine) further comprises with a spacer. In some embodiments, the spacer is between the conjugation moiety and the anti-PD-L1 diabody. In some embodiments, the spacer is between the conjugation moiety and the labeling agent. In some embodiments, the spacer is an alkyl spacer. In some embodiments, the spacer is a PEG spacer. In some embodiments, the PEG spacer comprises at least about 1, 2, 3, 4, 5, 6, 7, 8, 9, or 10 ethylene glycol unites. In some embodiments, the PEG spacer comprises about 1-20, 5-15, 8-12, or about 10 ethylene glycol units.

IV. Methods of Imaging and Treatment

One aspect of the present application provides a method of determining the distribution and/or expression level of PD-L1 in an individual using an imaging agent comprising an ant-PD-L1 diabody labeled with a radionuclide.

In some embodiments, there is provided a method of determining the distribution of PD-L1 in an individual, comprising: (a) administering to the individual an imaging agent comprising an anti-PD-L1 diabody (such as any one of the diabodies described here) labeled with a radionuclide; and (b) imaging the imaging agent in the individual with a non-invasive imaging technique. In some embodiments, the method further comprises determining the expression level of PD-L1 in a tissue of interest in the individual based on signals emitted by the imaging agent from the tissue. In some embodiments, the method further comprises preparing the imaging agent by labeling the anti-PD-L1 diabody with the radionuclide. In some embodiments, the non-invasive imaging technique comprises single photon emission computed tomography (SPECT) imaging or positron emission tomography (PET) imaging. In some embodiments, the non-invasive imaging technique further comprises computed tomography imaging, magnetic resonance imaging, chemical luminescence imaging, or electrochemical luminescence imaging. In some embodiments, the imaging agent is administered intravenously, intraperitoneally, intramuscularly, subcutaneously, or orally. In some embodiments, the imaging is carried out between about 10 minutes to about 24 hours after the administration of the imaging agent. In some embodiments, the method comprises imaging the individual over a period of time. In some embodiments, the radionuclide is selected from the group consisting of $^{64}$Cu, $^{18}$F, $^{67}$Ga, $^{68}$Ga, $^{111}$In, $^{177}$Lu, $^{90}$Y, $^{89}$Zr, $^{61}$Cu, $^{62}$Cu, $^{67}$Cu, $^{19}$F, $^{66}$Ga, $^{72}$Ga, $^{44}$Sc, $^{47}$Sc, $^{86}$Y, $^{88}$Y and $^{45}$Ti. In some embodiments, the radionuclide is $^{68}$Ga. In some embodiments, the anti-PD-L1 diabody is conjugated to a chelating compound that chelates the radionuclide. In some embodiments, the chelating compound is 1,4,7-triazacyclononane-1,4,7-trisacetic acid (NOTA), 1,4,7,10-tetraazacyclododecane-1,4,7,10-tetraacetic acid (DOTA) or derivatives thereof. In some embodiments, the anti-PD-L1 diabody cross-reacts with PD-L1 from a non-human mammal (e.g., mouse, rat or monkey).

In some embodiments, there is provided a method of determining the distribution of PD-L1 in an individual, comprising: (a) administering to the individual an imaging agent comprising an anti-PD-L1 diabody labeled with a radionuclide; and (b) imaging the imaging agent in the individual with a non-invasive imaging technique, wherein the anti-PD-L1 diabody comprises a first polypeptide and a second polypeptide, wherein the first polypeptide and the second polypeptide each comprises a heavy chain variable region ($V_H$) and a light chain variable region ($V_L$), wherein: a) the $V_H$ comprises an HC-CDR1 comprising the amino acid sequence of SEQ ID NO: 1, an HC-CDR2 comprising the amino acid sequence of SEQ ID NO: 6, and an HC-CDR3 comprising the amino acid sequence of any one of SEQ ID NO: 11, or a variant thereof comprising up to a total of about 5 amino acid substitutions in the HC-CDRs; and b) the $V_L$ comprises an LC-CDR1 comprising the amino acid sequence of SEQ ID NO: 14, an LC-CDR2 comprising the amino acid sequence of SEQ ID NO: 17, and an LC-CDR3 comprising the amino acid sequence of any one of SEQ ID NO: 20, or a variant thereof comprising up to a total of about 5 amino acid substitutions in the LC-CDRs. In some embodiments, there is provided a method of determining the distribution of PD-L1 in an individual, comprising: (a) administering to the individual an imaging agent comprising an anti-PD-L1 diabody labeled with a radionuclide; and (b) imaging the imaging agent in the individual with a non-invasive imaging technique, wherein the anti-PD-L1 diabody comprises a first polypeptide and a second polypeptide, wherein the first polypeptide and the second polypeptide each comprises a heavy chain variable region ($V_H$) and a light chain variable region ($V_L$), and wherein a) the $V_H$ and the $V_L$ of the first polypeptide, b) the $V_H$ and the $V_L$ of the second polypeptide, c) the $V_H$ of the first polypeptide and the $V_L$ of the second polypeptide, or d) the $V_H$ of the second polypeptide and the $V_L$ of the first polypeptide form a binding domain that specifically binds to PD-L1 competitively with an anti-PD-L1 antibody comprising a second heavy chain variable region ($V_{H-2}$) and a second light chain variable region ($V_{L-2}$), wherein: a) the $V_{H-2}$ comprises an HC-CDR1 comprising the amino acid sequence of SEQ ID NO: 1, an HC-CDR2 comprising the amino acid sequence of SEQ ID NO: 6, and an HC-CDR3 comprising the amino acid sequence of SEQ ID NO: 11; and b) the $V_{L-2}$ comprises an LC-CDR1 comprising the amino acid sequence of SEQ ID NO: 14, an LC-CDR2 comprising the amino acid sequence of SEQ ID NO: 17, and an LC-CDR3 comprising the amino acid sequence of SEQ ID NO: 20. In some embodiments, there is provided a method of determining the distribution of PD-L1 in an individual, comprising: (a) administering to the individual an imaging agent comprising an anti-PD-L1 diabody labeled with a radionuclide; and (b) imaging the imaging agent in the individual with a non-invasive imaging technique, wherein the anti-PD-L1 diabody comprises a first polypeptide and a second polypeptide, wherein the first polypeptide and the second polypeptide each comprises a heavy chain variable region ($V_H$) and a light chain variable region ($V_L$), wherein: a) the $V_H$ comprises a HC-CDR1, a HC-CDR2, and a HC-CDR3, respectively comprising the amino acid sequences of a CDR1, a CDR2, and a CDR3 within a second heavy chain variable region ($V_{H-2}$) having the sequence set forth in any of SEQ ID NOs: 22-24; and b) the $V_L$ comprises a LC-CDR1, a LC-CDR2, and a LC-CDR3, respectively comprising the amino acid sequences of a CDR1, a CDR2, and a CDR3 within a second light chain variable region ($V_{L-2}$) having the sequence set forth in any of SEQ ID NOs: 25-27.

In some embodiments, the method further comprises determining the expression level of PD-L1 in a tissue of interest in the individual based on signals emitted by the imaging agent from the tissue. In some embodiments, the method further comprises preparing the imaging agent by labeling the anti-PD-L1 diabody with the radionuclide. In some embodiments, the non-invasive imaging technique comprises single photon emission computed tomography (SPECT) imaging or positron emission tomography (PET) imaging. In some embodiments, the non-invasive imaging technique further comprises computed tomography imaging, magnetic resonance imaging, chemical luminescence imaging, or electrochemical luminescence imaging. In some embodiments, the imaging agent is administered intravenously, intraperitoneally, intramuscularly, subcutaneously, or orally. In some embodiments, the imaging is carried out between about 10 minutes to about 24 hours after the administration of the imaging agent. In some embodiments, the method comprises imaging the individual over a period of time. In some embodiments, the radionuclide is selected from the group consisting of $^{64}$Cu, $^{18}$F, $^{67}$Ga, $^{68}$Ga, $^{111}$In, $^{177}$Lu, $^{90}$Y, $^{89}$Zr, $^{61}$Cu, $^{62}$Cu, $^{67}$Cu, $^{19}$F, $^{66}$Ga, $^{72}$Ga, $^{44}$Sc, $^{47}$Sc, $^{86}$Y, $^{88}$Y and $^{45}$Ti. In some embodiments, the radionuclide is $^{68}$Ga. In some embodiments, the anti-PD-L1 diabody is conjugated to a chelating compound that chelates the radionuclide. In some embodiments, the chelating compound is NOTA, DOTA or derivatives thereof. In some embodiments, the anti-PD-L1 diabody cross-reacts with the PD-L1 from a non-human mammal (e.g., mouse, rat or monkey). In some embodiments, the anti-PD-L1 diabody is humanized.

The methods described herein can be used to determine the distribution of PD-L1 in an individual or a tissue of interest in an individual. The method may also provide qualitative or quantitative information on the expression level of PD-L1 in one or more tissues or organ of an individual. Additionally, the methods described herein can allow imaging of an individual over a period of time, for example, by providing a plurality of sets of imaging results at different time points after the administration of the imaging agent to the individual. In some embodiments, the imaging is carried out for at least 2, 3, 4, 5, 6, 7, 8, 9, 10 or more times over a period between about 10 minutes to about 24 hours (such as about any one of 10 minutes to 1 hour, 1 hour to 2 hours, 2 hours to 4 hours, 4 hours to 8 hours, 8 hours to 12 hours, 12 hours to 24 hours, 1 hour to 4 hours or 1 hour to 8 hours). In some embodiments, the imaging is carried out between about 10 minutes to about 24 hours after the administration of the imaging agent, for example, between about any one of 10 minutes to 1 hour, 1 hour to 2 hours, 2 hours to 4 hours, 4 hours to 8 hours, 8 hours to 12 hours, 12 hours to 24 hours, 1 hour to 4 hours or 1 hour to 8 hours.

Methods of imaging using labeled polypeptides are well known in the art, and any such known methods may be used with the imaging agents disclosed herein. See, for example, Srivastava (ed.), Radiolabeled Monoclonal Antibodies for Imaging and Therapy (Plenum Press 1988), Chase, "Medical Applications of Radioisotopes," in Remington's Pharmaceutical Sciences, 18th Edition, Gennaro et al. (eds.), pp. 624-652 (Mack Publishing Co., 1990), and Brown, "Clinical Use of Monoclonal Antibodies," in Biotechnology and Pharmacy 227-49, Pezzuto et al. (eds.) (Chapman & Hall 1993). In some embodiments, the non-invasive imaging technique uses positron-emitting radionuclides (PET isotopes), such as with an energy of about 511 keV, such as $^{18}$F, $^{68}$Ga, $^{64}$Cu, and $^{124}$I. Such radionuclides may be imaged by well-known PET scanning techniques. See, also, U.S. Pat. Nos. 6,953, 567; 9,884,131 and international patent application publication No. WO2016149188A1, and Kim H Y. et al., (2018) PLoS ONE 13 (3): e0192821, which are incorporated herein by reference.

In some embodiments, the non-invasive imaging technique comprises single photon emission computed tomography (SPECT) imaging. In some embodiments, the non-invasive imaging technique comprises positron emission tomography (PET) imaging. In some embodiments, SPEC or PET imaging is combined with one or more other non-invasive imaging method, which may or may not be based on the signals from the imaging agent. For example, PET may be combined with computed tomography (CT) imaging, magnetic resonance imaging (MRI), chemical luminescence imaging, or electrochemical luminescence imaging.

The imaging methods described herein are suitable for detecting PD-L1 at low, moderate, or high expression levels. In some embodiments, the imaging method provides dynamic information on the expression level and distribution of PD-L1. In some embodiments, the imaging method is capable of detecting PD-L1 in situations that might be challenging for other methods of detection, such as immunohistochemistry (IHC). For example, in some embodiments, the tissue of interest is negative for PD-L1 based on an immunohistochemistry (IHC) assay or another assay.

Molecular assays that may be used for detecting the presence or absence of PD-L1 include, but are not limited to, polymerase chain reaction (PCR)-based assays, next-generation sequencing (NGS) assays, hybridization assays, and ELISA. In some embodiments, the tissue of interest has a low expression level of PD-L1. In some embodiments, the tissue of interest only expresses PD-L1 upon infiltration of immune cells.

The imaging agent may be administered to the individual using any suitable dosage and routes of administration. The route of administration is in accordance with known and accepted methods, such as by single or multiple bolus or infusion over a period of time in a suitable manner, e.g., injection or infusion by subcutaneous, intravenous, intraperitoneal, intramuscular, intra-arterial, intralesional, intraarticular, intratumoral, or oral routes. The determination of the appropriate dosage or route of administration is well within the skill of an ordinary artisan. Animal experiments provide reliable guidance for the determination of effective doses for human diagnostic applications. Interspecies scaling of effective doses can be performed following the principles laid down by Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46.

Diagnosis and Treatment

The methods described herein are useful for diagnosis and as a companion diagnostic method for treatment of a variety of diseases and conditions that are associated with abnormal immune response. In some embodiments, the disease or condition is associated with immune deficiency. In some embodiments, the disease or condition is a cancer, an infectious disease, an autoimmune disease, or a metabolic disease.

In some embodiments, there is provided a method of diagnosing an individual having a disease or condition, comprising: (a) determining the distribution of PD-L1 in the individual using any one of the methods for determining distribution of PD-L1 described herein; and (b) diagnosing the individual as positive for PD-L1 if signal of the imaging agent is detected at a tissue of interest, or diagnosing the individual as negative for PD-L1 if signal of the imaging agent is not detected at a tissue of interest. In some embodiments, the disease or condition is a cancer, an infectious disease, an autoimmune disease, or a metabolic disease.

In some embodiments, there is provided a method of diagnosing an individual having a disease or condition, comprising: (a) administering to the individual an imaging agent comprising an anti-PD-L1 diabody labeled with a radionuclide; (b) imaging the imaging agent in the individual with a non-invasive imaging technique; and (c) diagnosing the individual as positive for PD-L1 if signal of the imaging agent is detected at a tissue of interest, or diagnosing the individual as negative for PD-L1 if signal of the imaging agent is not detected at a tissue of interest. In some embodiments, the method further comprises determining the expression level of PD-L1 in a tissue of interest in the individual based on signals emitted by the imaging agent from the tissue. In some embodiments, the method further comprises preparing the imaging agent by labeling the anti-PD-L1 diabody with the radionuclide. In some embodiments, the non-invasive imaging technique comprises single photon emission computed tomography (SPECT) imaging or positron emission tomography (PET) imaging. In some embodiments, the non-invasive imaging technique further comprises computed tomography imaging, magnetic resonance imaging, chemical luminescence imaging, or electrochemical luminescence imaging. In some embodiments, the imaging agent is administered intravenously, intraperitoneally, intramuscularly, subcutaneously, or orally. In some embodiments, the imaging is carried out between about 10 minutes to about 24 hours after the administration of the imaging agent. In some embodiments, the method comprises imaging the individual over a period of time. In some embodiments, the radionuclide is selected from the group consisting of $^{64}$Cu, $^{18}$F, $^{67}$Ga, $^{68}$Ga, $^{111}$In, $^{177}$Lu, $^{90}$Y, $^{89}$Zr, $^{61}$Cu, $^{62}$Cu, $^{67}$Cu, $^{19}$F, $^{66}$Ga, $^{72}$Ga, $^{44}$Sc, $^{47}$Sc, $^{86}$Y, $^{88}$Y and $^{45}$Ti. In some embodiments, the radionuclide is $^{68}$Ga. In some embodiments, the anti-PD-L1 diabody is conjugated to a chelating compound that chelates the radionuclide. In some embodiments, the chelating compound is NOTA, DOTA or derivatives thereof. In some embodiments, the anti-PD-L1 diabody cross-reacts with the PD-L1 from a non-human mammal (e.g., mouse, rat or monkey). In some embodiments, the diabody is humanized. In some embodiments, the disease or condition is a cancer, an infectious disease, an autoimmune disease, or a metabolic disease.

In some embodiments, there is provided a method of diagnosing an individual having a disease or condition, comprising: (a) administering to the individual an imaging agent comprising an anti-PD-L1 diabody labeled with a radionuclide; (b) imaging the imaging agent in the individual with a non-invasive imaging technique; and (c) diagnosing the individual as positive for PD-L1 if signal of the imaging agent is detected at a tissue of interest, or diagnosing the individual as negative for the PD-L1 if signal of the imaging agent is not detected at a tissue of interest; wherein the anti-PD-L1 diabody comprises a first polypeptide and a second polypeptide, wherein the first polypeptide and the second polypeptide each comprises a heavy chain variable region ($V_H$) and a light chain variable region ($V_L$), wherein: a) the $V_H$ comprises an HC-CDR1 comprising the amino acid sequence of SEQ ID NO: 1, an HC-CDR2 comprising the amino acid sequence of SEQ ID NO: 6, and an HC-CDR3 comprising the amino acid sequence of any one of SEQ ID NO: 11, or a variant thereof comprising up to a total of about 5 amino acid substitutions in the HC-CDRs; and b) the $V_L$ comprises an LC-CDR1 comprising the amino acid sequence of SEQ ID NO: 14, an LC-CDR2 comprising the amino acid sequence of SEQ ID NO: 17, and an LC-CDR3 comprising the amino acid sequence of any one of SEQ ID NO: 20, or a variant thereof comprising up to a total of about 5 amino acid substitutions in the LC-CDRs. In some embodiments, there is provided a method of diagnosing an individual having a disease or condition, comprising: (a) administering to the individual an imaging agent comprising an anti-PD-L1 diabody labeled with a radionuclide; (b) imaging the imaging agent in the individual with a non-invasive imaging technique; and (c) diagnosing the individual as positive for PD-L1 if signal of the imaging agent is detected at a tissue of interest, or diagnosing the individual as negative for the PD-L1 if signal of the imaging agent is not detected at a tissue of interest; wherein the anti-PD-L1 diabody comprises a first polypeptide and a second polypeptide, wherein the first polypeptide and the second polypeptide each comprises a heavy chain variable region ($V_H$) and a light chain variable region ($V_L$), and wherein a) the $V_H$ and the $V_L$ of the first polypeptide, b) the $V_H$ and the $V_L$ of the second polypeptide, c) the $V_H$ of the first polypeptide and the $V_L$ of the second polypeptide, or d) the $V_H$ of the second polypeptide and the $V_L$ of the first polypeptide form a binding domain that specifically binds to PD-L1 competitively with an anti-PD-L1 antibody comprising a second heavy chain variable region ($V_{H\text{-}2}$) and a second light chain variable region ($V_{L-2}$), wherein: a) the $V_{H-2}$ comprises an HC-CDR1 comprising the amino acid sequence of SEQ ID NO: 1, an HC-CDR2 comprising the amino acid sequence of SEQ ID NO: 6, and an HC-CDR3 comprising the amino acid sequence of SEQ ID NO: 11; and b) the $V_{L-2}$ comprises an LC-CDR1 comprising the amino acid sequence of SEQ ID NO: 14, an LC-CDR2 comprising the amino acid sequence of SEQ ID NO: 17, and an LC-CDR3 comprising the amino acid sequence of SEQ ID NO: 20. In some embodiments, there is provided a method of diagnosing an individual having a disease or condition, comprising: (a) administering to the individual an imaging agent comprising an anti-PD-L1 diabody labeled with a radionuclide; (b) imaging the imaging agent in the individual with a non-invasive imaging technique; and (c) diagnosing the individual as positive for PD-L1 if signal of the imaging agent is detected at a tissue of interest, or diagnosing the individual as negative for the PD-L1 if signal of the imaging agent is not detected at a tissue of interest; wherein the anti-PD-L1 diabody comprises a first polypeptide and a second polypeptide, wherein the first polypeptide and the second polypeptide each comprises a heavy chain variable region ($V_H$) and a light chain variable region ($V_L$), wherein: a) the $V_H$ comprises a HC-CDR1, a HC-CDR2, and a HC-CDR3, respectively comprising the amino acid sequences of a CDR1, a CDR2, and a CDR3 within a second heavy chain variable region ($V_{H-2}$) having the sequence set forth in any of SEQ ID NOs: 22-24; and b) the $V_L$ comprises a LC-CDR1, a LC-CDR2, and a LC-CDR3, respectively comprising the amino acid sequences of a CDR1, a CDR2, and a CDR3 within a second light chain variable region ($V_{L-2}$) having the sequence set forth in any of SEQ ID NOs: 25-27. In some embodiments, the $V_H$ in the first polypeptide and the second polypeptide each comprises a G44C mutation, and the $V_L$ in the first polypeptide and the second polypeptide each comprises a Q100C mutation, wherein the G44C in the $V_H$ of the first polypeptide and the Q100C in the $V_L$ of the second polypeptide form a first disulfide bond, and wherein the Q100C in the $V_L$ of the first polypeptide and the G44C in the $V_H$ of the second polypeptide form a second disulfide bond.

In some embodiments, the method further comprises determining the expression level of PD-L1 in a tissue of interest in the individual based on signals emitted by the imaging agent from the tissue. In some embodiments, the method further comprises preparing the imaging agent by labeling the diabody with the radionuclide. In some embodiments, the non-invasive imaging technique comprises single photon emission computed tomography (SPECT) imaging or positron emission tomography (PET) imaging. In some embodiments, the non-invasive imaging technique further comprises computed tomography imaging, magnetic resonance imaging, chemical luminescence imaging, or electrochemical luminescence imaging. In some embodiments, the imaging agent is administered intravenously, intraperitoneally, intramuscularly, subcutaneously, or orally. In some embodiments, the imaging is carried out between about 10 minutes to about 24 hours after the administration of the imaging agent. In some embodiments, the method comprises imaging the individual over a period of time. In some embodiments, the anti-PD-L1 diabody is humanized. In some embodiments, the radionuclide is selected from the group consisting of $^{64}Cu$, $^{18}F$, $^{67}Ga$, $^{68}Ga$, $^{111}In$, $^{177}Lu$, $^{90}Y$, $^{89}Zr$, $^{61}Cu$, $^{62}Cu$, $^{67}Cu$, $^{19}F$, $^{66}Ga$, $^{72}Ga$, $^{44}Sc$, $^{47}Sc$, $^{86}Y$, $^{88}Y$ and $^{45}Ti$. In some embodiments, the radionuclide is $^{68}Ga$. In some embodiments, the anti-PD-L1 diabody is conjugated to a chelating compound that chelates the radionuclide. In some embodiments, the chelating compound is NOTA, DOTA or derivatives thereof. In some embodiments, the disease or condition is a cancer, an infectious disease, an autoimmune disease, or a metabolic disease.

One aspect of the present application provides a method of determining the distribution and/or expression level of PD-L1 in an individual using a) an effective amount of an anti-PD-L1 diabody agent comprising an anti-PD-L1 diabody (such as any of the diabodies described herein) and a first conjugation moiety, and b) an effective amount of a labeling agent (e.g., radionuclide compound) comprising a label (e.g., radionuclide) and a second conjugation moiety, wherein the first conjugation moiety and the second conjugation moiety are conjugated to each other in vivo to provide an imaging agent. In some embodiments, the method further comprises imaging the imaging agent in the individual with a non-invasive imaging technique.

In some embodiments, there is provided a method of determining the distribution of an PD-L1 in an individual, comprising: a) administering to the individual an effective amount of an anti-PD-L1 diabody agent comprising an anti-PD-L1 diabody (such as any of the anti-PD-L1 diabodies described herein) and a first conjugation moiety; b) subsequently administering to the individual an effective amount of a radionuclide compound comprising a radionuclide and a second conjugation moiety, wherein the first conjugation moiety and the second conjugation moiety are conjugated to each other in vivo to provide an imaging agent; and c) imaging the imaging agent in the individual with a non-invasive imaging technique. In some embodiments, there is provided a method of determining the distribution of PD-L1 in an individual, comprising administering to the individual an effective amount of an anti-PD-L1 diabody agent comprising an anti-PD-L1 diabody and a first conjugation moiety, wherein the individual is to be administered with an effective amount of a radionuclide compound comprising a radionuclide and a second conjugation moiety, wherein the first conjugation moiety and the second conjugation moiety are conjugated to each other in vivo to provide an imaging agent. In some embodiments, there is provided a method of determining the distribution of PD-L1 in an individual who has been administered with an effective amount of an anti-PD-L1 diabody agent comprising an anti-PD-L1 diabody and a first conjugation moiety, comprising administering to the individual an effective amount of a radionuclide compound comprising a radionuclide and a second conjugation moiety, wherein the first conjugation moiety and the second conjugation moiety are conjugated to each other in vivo to provide an imaging agent.

In some embodiments, there is provided a method of determining the distribution of an PD-L1 in an individual, comprising: a) administering to the individual an effective amount of an anti-PD-L1 diabody agent comprising an anti-PD-L1 diabody and a first conjugation moiety; b) subsequently administering to the individual an effective amount of a radionuclide compound comprising a radionuclide and a second conjugation moiety, wherein the first conjugation moiety and the second conjugation moiety are conjugated to each other in vivo to provide an imaging agent; and c) imaging the imaging agent in the individual with a non-invasive imaging technique. In some embodiments, the anti-PD-L1 diabody comprises a first polypeptide and a second polypeptide, wherein the first polypeptide and the second polypeptide each comprises a heavy chain variable region ($V_H$) and a light chain variable region ($V_L$), wherein: a) the $V_H$ comprises an HC-CDR1 comprising the amino acid sequence of SEQ ID NO: 1, an HC-CDR2 comprising the amino acid sequence of SEQ ID NO: 6, and an HC-CDR3 comprising the amino acid sequence of any one of SEQ ID NO: 11, or a variant thereof comprising up to a total of about 5 amino acid substitutions in the HC-CDRs; and b) the $V_L$ comprises an LC-CDR1 comprising the amino acid sequence of SEQ ID NO: 14, an LC-CDR2 comprising the amino acid sequence of SEQ ID NO: 17, and an LC-CDR3 comprising the amino acid sequence of any one of SEQ ID NO: 20, or a variant thereof comprising up to a total of about 5 amino acid substitutions in the LC-CDRs. In some embodiments, the anti-PD-L1 diabody comprises a first polypeptide and a second polypeptide, wherein the first polypeptide and the second polypeptide each comprises a heavy chain variable region ($V_H$) and a light chain variable region ($V_L$), and wherein a) the $V_H$ and the $V_L$ of the first polypeptide, b) the $V_H$ and the $V_L$ of the second polypeptide, c) the $V_H$ of the first polypeptide and the $V_L$ of the second polypeptide, or d) the $V_H$ of the second polypeptide and the $V_L$ of the first polypeptide form a binding domain that specifically binds to PD-L1 competitively with an anti-PD-L1 antibody comprising a second heavy chain variable region ($V_{H-2}$) and a second light chain variable region ($V_{L-2}$), wherein: a) the $V_{H-2}$ comprises an HC-CDR1 comprising the amino acid sequence of SEQ ID NO: 1, an HC-CDR2 comprising the amino acid sequence of SEQ ID NO: 6, and an HC-CDR3 comprising the amino acid sequence of SEQ ID NO: 11; and b) the $V_{L-2}$ comprises an LC-CDR1 comprising the amino acid sequence of SEQ ID NO: 14, an LC-CDR2 comprising the amino acid sequence of SEQ ID NO: 17, and an LC-CDR3 comprising the amino acid sequence of SEQ ID NO: 20. In some embodiments, the anti-PD-L1 diabody comprises a first polypeptide and a second polypeptide, wherein the first polypeptide and the second polypeptide each comprises a heavy chain variable region ($V_H$) and a light chain variable region ($V_L$), wherein: a) the $V_H$ comprises a HC-CDR1, a HC-CDR2, and a HC-CDR3, respectively comprising the amino acid sequences of a CDR1, a CDR2, and a CDR3 within a second heavy chain variable region ($V_{H-2}$) having the sequence set forth in any of SEQ ID NOs: 22-24; and b) the $V_L$ comprises a LC-CDR1, a LC-CDR2, and a LC-CDR3, respectively comprising the amino acid sequences of a CDR1, a CDR2, and a CDR3 within a second light chain variable region ($V_{L-2}$) having the sequence set forth in any of SEQ ID NOs: 25-27. In some embodiments, the radionuclide is selected from the group consisting of $^{64}Cu$, $^{18}F$, $^{67}Ga$, $^{68}Ga$, $^{111}In$, $^{177}Lu$, $^{90}Y$, $^{89}Zr$, $^{61}Cu$, $^{62}Cu$, $^{67}Cu$, $^{19}F$, $^{66}Ga$, $^{72}Ga$, $^{44}Sc$, $^{47}Sc$, $^{86}Y$, $^{88}Y$ and $^{45}Ti$. In some embodiments, the radionuclide is $^{68}Ga$. In some embodiments, the first conjugation moiety and the second conjugation moiety each comprises a member of a click chemistry pair, and are conjugated to each other via click chemistry. In some embodiments, the first conjugation moiety is a trans-cyclooctene (TCO) and the second conjugation moiety is a tetrazine (Tz), or the first conjugation moiety is a Tz and the second conjugation moiety is a TCO. In some embodiments, the radionuclide compound is administered immediately after the administration of the diabody agent. In some embodiments, the radionuclide compound is administered between about 1 hour and about 100 hours after the administration of the diabody agent. In some embodiments, the radionuclide compound and/or the diabody agent comprises a chelating compound that chelates the radionuclide. In some embodiments, the chelating compound is 1,4,7-triazacyclononane-1,4,7-trisacetic acid (NOTA), 1,4,7,10-tetraazacyclododecane-1,4,7,10-tetraacetic acid (DOTA) or a derivative thereof. In some embodiments, the individual has a solid tumor, a hematological malignancy, an infectious disease, autoimmune disease, or metabolic disease.

Treatment

In some embodiments, there is provided a method of treating an individual having a disease or condition, comprising: (a) diagnosing the individual using any method of diagnosis described herein; and (b) administering to the individual an effective amount of a therapeutic agent targeting PD-L1 or PD-1, if the individual is diagnosed as positive for PD-L1. In some embodiments, the therapeutic agent is an inhibitor of PD-L1 or PD-1. In some embodiments, the therapeutic agent is a radiolabeled molecule specifically binding PD-L1 or PD-1. In some embodiments, the disease or condition is a cancer, an infectious disease, an autoimmune disease, or a metabolic disease. In some embodiments, the disease or condition is a bladder, ovary, or prostate disease.

In some embodiments, there is provided a method of treating an individual having a disease or condition, comprising: (a) administering to the individual an imaging agent comprising an anti-PD-L1 diabody labeled with a radionuclide; (b) imaging the imaging agent in the individual with a non-invasive imaging technique; (c) diagnosing the individual as positive for PD-L1 if signal of the imaging agent is detected at a tissue of interest, or diagnosing the individual as negative for PD-L1 if signal of the imaging agent is not detected at a tissue of interest; and (d) administering to the individual an effective amount of a therapeutic agent targeting PD-L1 or PD-L1 receptor (e.g., an inhibitor of PD-L1 or PD-1, or a radiolabeled molecule specifically binding PD-L1 or PD-1), if the individual is diagnosed as positive for PD-L1. In some embodiments, the method further comprises determining the expression level of PD-L1 in a tissue of interest in the individual based on signals emitted by the imaging agent from the tissue. In some embodiments, the method further comprises preparing the imaging agent by labeling PD-L1 with the radionuclide. In some embodiments, the non-invasive imaging technique comprises single photon emission computed tomography (SPECT) imaging or positron emission tomography (PET) imaging. In some embodiments, the non-invasive imaging technique further comprises computed tomography imaging, magnetic resonance imaging, chemical luminescence imaging, or electrochemical luminescence imaging. In some embodiments, the imaging agent is administered intravenously, intraperitoneally, intramuscularly, subcutaneously, or orally. In some embodiments, the imaging is carried out between about 10 minutes to about 24 hours after the administration of the imaging agent. In some embodiments, the method comprises imaging the individual over a period of time. In some embodiments, the radionuclide is selected from the group consisting of $^{64}Cu$, $^{18}F$, $^{67}Ga$, $^{68}Ga$, $^{111}In$, $^{177}Lu$, $^{90}Y$, $^{89}Zr$, $^{61}Cu$, $^{62}Cu$, $^{67}Cu$, $^{19}F$, $^{66}Ga$, $^{72}Ga$, $^{44}Sc$, $^{47}Sc$, $^{86}Y$, $^{88}Y$ and $^{45}Ti$. In some embodiments, the radionuclide is $^{68}Ga$. In some embodiments, the diabody is conjugated to a chelating compound that chelates the radionuclide. In some embodiments, the chelating compound is NOTA, DOTA or derivatives thereof. In some embodiments, the anti-PD-L1 diabody cross-reacts with the PD-L1 from a non-human mammal (e.g., mouse, rat or monkey). In some embodiments, the diabody is humanized. In some embodiments, the disease or condition is a cancer, an infectious disease, an autoimmune disease, or a metabolic disease.

In some embodiments, the individual has a cancer. The cancer may comprise non-solid tumors (such as hematological tumors, for example, leukemias and lymphomas) or may comprise solid tumors. Exemplary cancers that may be diagnosed using the methods described herein, include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included. Solid or hematologic cancers discussed herein include, but is not limited to, Hodgkin lymphoma, non-Hodgkin lymphoma, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, Kaposi's sarcoma, soft tissue sarcoma, uterine sacronomasynovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, and melanoma.

The methods described herein are applicable to solid or hematologic cancers of all stages, including stages, I, II, III, and IV, according to the American Joint Committee on Cancer (AJCC) staging groups. In some embodiments, the solid or hematologic cancer is an/a: early stage cancer, non-metastatic cancer, primary cancer, advanced cancer, locally advanced cancer, metastatic cancer, or cancer in remission.

In some embodiments, the individual has a hematologic cancer. Exemplary hematologic cancers that can be diagnosed using the methods described herein include, but are not limited to, leukemia, lymphoma, acute lymphoblastic leukemia (ALL), acute non-lymphoblastic leukemia (ANLL), chronic lymphocytic leukemia (CLL), chronic myeloid leukemia (CML), non-Hodgkin lymphoma, and Hodgkin lymphoma.

In some embodiments, the individual has a solid tumor. Exemplary solid tumors that can be diagnosed using the methods described herein include, but are not limited to, colon tumor, melanoma, kidney tumor, ovarian tumor, lung tumor, breast tumor, and pancreatic tumor.

Cancer treatments can be evaluated, for example, by tumor regression, tumor weight or size shrinkage, time to progression, duration of survival, progression free survival, overall response rate, duration of response, quality of life, protein expression and/or activity. Approaches to determining efficacy of the therapy can be employed, including for example, measurement of response through radiological imaging.

In some embodiments, the individual has an infectious disease. The infection may be caused by a virus, bacteria, protozoa, or parasite. Exemplary pathogens include, but are not limited to, *Acinetobacter baumannii, Anaplasma genus, Anaplasma phagocytophilum, Ancylostoma braziliense, Ancylostoma duodenale, Arcanobacterium haemolyticum, Ascaris lumbricoides, Aspergillus* genus, Astroviridae, *Babesia* genus, *Bacillus anthracis, Bacillus cereus, Bartonella henselae,* BK virus, *Blastocystis hominis, Blastomyces dermatitidis, Bordetella pertussis, Borrelia burgdorferi, Borrelia* genus, *Borrelia* spp, *Brucella* genus, *Brugia malayi, Bunyaviridae* family, *Burkholderia cepacia* and other *Burkholderia* species, *Burkholderia mallei, Burkholderia pseudomallei, Caliciviridae* family, *Campylobacter* genus, *Candida albicans, Candida* spp, *Chlamydia trachomatis, Chlamydophila pneumoniae, Chlamydophila psittaci,* CJD prion, *Clonorchis sinensis, Clostridium botulinum, Clostridium difficile, Clostridium perfringens, Clostridium perfringens, Clostridium* spp, *Clostridium tetani, Coccidioides* spp, coronaviruses, *Corynebacterium diphtheriae, Coxiella burnetii,* Crimean-Congo hemorrhagic fever virus, *Cryptococcus neoformans, Cryptosporidium* genus, Cytomegalovirus (CMV), Dengue viruses (DEN-1, DEN-2, DEN-3 and DEN-4), *Dientamoeba fragilis,* Ebolavirus (EBOV), *Echinococcus* genus, *Ehrlichia chaffeensis, Ehrlichia ewingii, Ehrlichia* genus, *Entamoeba histolytica, Enterococcus* genus, Enterovirus genus, Enteroviruses, mainly Coxsackie A virus and Enterovirus 71 (EV71), *Epidermophyton* spp, Epstein-Barr Virus (EBV), *Escherichia coli* O157: H7, O111 and O104: H4, *Fasciola hepatica* and *Fasciola gigantica,* FFI prion, Filarioidea superfamily, Flaviviruses, *Francisella tularensis, Fusobacterium genus, Geotrichum candidum, Giardia intestinalis, Gnathostoma* spp, GSS prion, Guanarito virus, *Haemophilus ducreyi, Haemophilus influenzae, Helicobacter pylori,* Henipavirus (Hendra virus Nipah virus), Hepatitis A Virus, Hepatitis B Virus (HBV), Hepatitis C Virus (HCV), Hepatitis D Virus, Hepatitis E Virus, Herpes simplex virus 1 and 2 (HSV-1 and HSV-2), *Histoplasma capsulatum,* HIV (Human immunodeficiency virus), *Hortaea werneckii,* Human bocavirus (HBoV), Human herpesvirus 6 (HHV-6) and Human herpesvirus 7 (HHV-7), Human metapneumovirus (hMPV), Human papillomavirus (HPV), Human parainfluenza viruses (HPIV), Human T cell leukemia virus 1 (HTLV-1), Japanese encephalitis virus, JC virus, Junin virus, Kaposi's Sarcoma associated herpesvirus (KSHV), *Kingella kingae, Klebsiella granulomatis,* Kuru prion, Lassa virus, *Legionella pneumophila, Leishmania* genus, *Leptospira* genus, *Listeria monocytogenes,* Lymphocytic choriomeningitis virus (LCMV), Machupo virus, *Malassezia* spp, Marburg virus, Measles virus, *Metagonimus yokagawai,* Microsporidia phylum, *Molluscum contagiosum* virus (MCV), Mumps virus, *Mycobacterium leprae* and *Mycobacterium* lepromatosis, *Mycobacterium tuberculosis, Mycobacterium ulcerans, Mycoplasma pneumoniae, Naegleria fowleri, Necator americanus, Neisseria gonorrhoeae, Neisseria meningitidis, Nocardia asteroides, Nocardia* spp, *Onchocerca volvulus, Orientia tsutsugamushi,* Orthomyxoviridae family (Influenza), *Paracoccidioides brasiliensis, Paragonimus* spp, *Paragonimus westermani,* Parvovirus B19, *Pasteurella* genus, *Plasmodium* genus, *Pneumocystis jirovecii,* Poliovirus, Rabies virus, Respiratory syncytial virus (RSV), Rhinovirus, rhinoviruses, *Rickettsia akari, Rickettsia* genus, *Rickettsia prowazekii, Rickettsia rickettsii, Rickettsia typhi,* Rift Valley fever virus, Rotavirus, *Rubella* virus, *Sabia* virus, *Salmonella* genus, *Sarcoptes scabiei,* SARS coronavirus, *Schistosoma* genus, *Shigella* genus, Sin Nombre virus, Hantavirus, *Sporothrix schenckii, Staphylococcus* genus, *Staphylococcus* genus, *Streptococcus agalactiae, Streptococcus pneumoniae, Streptococcus pyogenes, Strongyloides stercoralis, Taenia* genus, *Taenia solium,* Tick-borne encephalitis virus (TBEV), *Toxocara canis* or *Toxocara cati, Toxoplasma gondii, Treponema pallidum, Trichinella spiralis, Trichomonas vaginalis, Trichophyton* spp, *Trichuris trichiura, Trypanosoma brucei, Trypanosoma cruzi, Ureaplasma urealyticum,* Varicella zoster virus (VZV), Varicella *zoster* virus (VZV), *Variola major* or *Variola minor,* vCJD prion, Venezuelan equine encephalitis virus, *Vibrio cholerae,* West Nile virus, Western equine encephalitis virus, *Wuchereria bancrofti*, Yellow fever virus, *Yersinia enterocolitica, Yersinia pestis*, and *Yersinia pseudotuberculosis*.

In some embodiments, the individual has an autoimmune disease. Exemplary autoimmune disease include, but are not limited to, Behcet disease, systemic lupus erythematosus, multiple sclerosis (systemic scleroderma and progressive systemic scleroderma), scleroderma, polymyositis, dermatomyositis, periarteritis nodosa (polyarteritis nodosa and microscopic polyangiitis), aortitis syndrome (Takayasu arteritis), malignant rheumatoid arthritis, rheumatoid arthritis, Wegner's granulomatosis, mixed connective tissue disease, Sjogren syndrome, adult-onset Still's disease, allergic granulomatous angiitis, hypersensitivity angiitis, Cogan's syndrome, RS3PE, temporal arteritis, polymyalgia rheumatica, fibromyalgia syndrome, antiphospholipid antibody syndrome, eosinophilic fasciitis, IgG4-related diseases (e.g., primary sclerosing cholangitis and autoimmune pancreatitis), Guillain-Barre syndrome, myasthenia gravis, chronic atrophic gastritis, autoimmune hepatitis, primary biliary cirrhosis, aortitis syndrome, Goodpasture's syndrome, rapidly progressive glomerulonephritis, megaloblastic anemia, autoimmune hemolytic anemia, autoimmune neutropenia, idiopathic thrombocytopenia purpura, Graves' disease (hyperthyroidism), Hashimoto's thyroiditis, autoimmune adrenal insufficiency, primary hypothyroidism, idiopathic Addison's disease (chronic adrenal insufficiency), type I diabetes mellitus, chronic discoid lupus erythematosus, localized scleroderma, psoriasis, psoriatic arthritis, pemphigus, pemphigoid, herpes gestationis, linear IgA bullous skin disease, epidermolysis bullosa acquisita, alopecia areata, vitiligo, Harada disease, autoimmune optic neuropathy, idiopathic azoospermia, recurrent fetal loss, and inflammatory bowel diseases (ulcerative colitis and Crohn's disease).

In some embodiments, the individual has a metabolic disease associated with abnormal immune response. Exemplary metabolic diseases include, but are not limited to, inflammatory bowel disease, multiple sclerosis, psoriasis, rheumatoid arthritis, and systemic lupus erythematosus.

V. Methods of Preparation

Methods of Preparing an Imaging Agent

In some embodiments, there is provided a method of preparing an imaging agent targeting PD-L1. The imaging agents described herein may be prepared by a number of processes as generally described below and more specifically in the Examples.

In some embodiments, there is provided a method of preparing an imaging agent targeting PD-L1, comprising: a) conjugating a chelating compound to the diabody as described herein to provide an anti-PD-L1 diabody conjugate; b) contacting a radionuclide with the anti-PD-L1 diabody conjugate, thereby providing the imaging agent. In some embodiments, the chelating compound is NOTA, DOTA or derivatives thereof. In some embodiments, the radionuclide is selected from the group consisting of $^{64}$Cu, $^{18}$F, $^{67}$Ga, $^{68}$Ga, $^{111}$In, $^{177}$Lu, $^{90}$Y, $^{89}$Zr, $^{61}$Cu, $^{62}$Cu, $^{67}$Cu, $^{19}$F, $^{66}$Ga, $^{72}$Ga, $^{44}$Sc, $^{47}$Sc, $^{86}$Y, $^{88}$Y and $^{45}$Ti. In some embodiments, the radionuclide is $^{68}$Ga. In some embodiments, the chelating compound is conjugated to a lysine of the diabody moiety. In some embodiments, the method further comprises isolating the imaging agent from the chelating compound and/or the radionuclide.

In some embodiments, there is provided a method of preparing an imaging agent targeting PD-L1, comprising: (a) conjugating a chelating compound to an anti-PD-L1 diabody (such as any of the diabodies described herein) to provide a diabody conjugate; and (b) contacting a radionuclide with the diabody conjugate, thereby providing the imaging agent. In some embodiments, the chelating compound is NOTA, DOTA or derivatives thereof. In some embodiments, the method comprises incubating the diabody with the chelating compound at 37° C. In some embodiments, the incubation lasts at least about 20 minutes, 40 minutes, or 60 minutes. In some embodiments, the radionuclide is selected from the group consisting of $^{64}$Cu, $^{18}$F, $^{67}$Ga, $^{68}$Ga, $^{111}$In, $^{177}$Lu, $^{90}$Y, $^{89}$Zr, $^{61}$Cu, $^{62}$Cu, $^{67}$Cu, $^{19}$F, $^{66}$Ga, $^{72}$Ga, $^{44}$Sc, $^{47}$Sc, $^{86}$Y, $^{88}$Y and $^{45}$Ti. In some embodiments, the radionuclide is $^{68}$Ga. In some embodiments, the chelating compound is conjugated to a lysine of the diabody. In some embodiments, the method further comprises isolating the imaging agent from the chelating compound and/or the radionuclide.

In some embodiments, there is provided a method of preparing an imaging agent targeting PD-L1, comprising: (a) contacting a chelating compound with a radionuclide; (b) conjugating the chelating compound that chelates the radionuclide to any one of the anti-PD-L1 diabodies described herein, thereby providing the imaging agent. In some embodiments, the chelating compound is NOTA, DOTA or derivatives thereof. In some embodiments, the radionuclide is selected from the group consisting of $^{64}$Cu, $^{18}$F, $^{67}$Ga, $^{68}$Ga, $^{111}$In, $^{177}$Lu, $^{90}$Y, $^{89}$Zr, $^{61}$Cu, $^{62}$Cu, $^{67}$Cu, $^{19}$F, $^{66}$Ga, $^{72}$Ga, $^{44}$Sc, $^{47}$Sc, $^{86}$Y, $^{88}$Y and $^{45}$Ti. In some embodiments, the radionuclide is $^{68}$Ga. In some embodiments, the chelating compound is conjugated to a lysine of the diabody. In some embodiments, the method further comprises isolating the imaging agent from the chelating compound and/or the radionuclide.

In some embodiments, there is provided a method of preparing an imaging agent targeting PD-L1, comprising: (a) conjugating an anti-PD-L1 diabody as described herein to p-SCN-Bn-NOTA to provide an anti-PD-L1 diabody conjugate; (b) contacting $^{68}$Ga with the anti-PD-L1 diabody conjugate, thereby providing the imaging agent. In some embodiments, the method comprises incubating the diabody with p-SCN-Bn-NOTA at 37° C. In some embodiments, the incubation lasts at least about 20 minutes, 40 minutes, or 60 minutes. In some embodiments, the diabody conjugate is isolated by passing the mixture of the diabody and p-SCN-Bn-NOTA through a column (e.g., NAP-5 column). In some embodiments, the imaging agent is isolated by passing the mixture of $^{68}$Ga with the diabody conjugate through a column (e.g., NAP-5 column).

Diabody Expression and Production

The diabodies described herein can be prepared using any known methods in the art, including those described below and in the Examples.

In some embodiments, there is provided a method of producing an anti-PD-L1 diabody, comprising: a) culturing the isolated host cell as described herein under conditions effective to express the diabody; and b) obtaining the expressed diabody from the host cell. In some embodiments, the host cell is CHO cells.

Nucleic Acid Molecules Encoding diabodies

The present application further provides isolated nucleic acid molecules comprising polynucleotides that encode the diabodies or a portion of the diabodies described herein. In some embodiments, a nucleic acid molecule comprises a polynucleotide that encodes the heavy chain variable region or the light chain variable region of the first or the second polypeptide. In some embodiments, a nucleic acid molecule comprises a polynucleotide that encodes the first polypeptide and/or the second polypeptide of the diabodies described here. In some embodiments, a first nucleic acid molecule comprises a polynucleotide that encodes the first polypeptide of an anti-PD-L1 diabody described herein, and a second nucleic acid molecule comprises a second polynucleotide of the same diabody.

In some embodiments, the nucleic acid molecule further comprises a polynucleotide that encodes a signal sequence (such as the signal sequence of SEQ ID NO: 35).

In some embodiments, the nucleic acid molecule further comprises a second polynucleotide that encodes a tag (such as a His-tag).

In some embodiments, the nucleic acid molecule comprises a nucleic acid sequence of any one of SEQ ID NOs: 44, 45, 48-51, or a variant thereof having at least about 80% (such as at least about any one of 80%, 85%, 90%, 95%, 96%, 97%, 98%, or 99%) sequence identity to the nucleic acid sequence of any one of SEQ ID NO: 22-24.

Nucleic acid molecules may be constructed using recombinant DNA techniques conventional in the art. In some embodiments, a nucleic acid molecule is an expression vector that is suitable for expression in a selected host cell.

Vectors

Vectors comprising polynucleotides that encode diabodies described herein (e.g., anti-PD-L1 antibody moieties) are provided. Vectors comprising polynucleotides that encode a portion of the diabodies described herein (such as the heavy chain variable region or the light chain variable region of the first or second polypeptides of the diabodies) are also provided. Such vectors include, but are not limited to, DNA vectors, phage vectors, viral vectors, retroviral vectors, etc. In some embodiments, the vector comprises a polynucleotide sequence encoding the heavy chain variable region or the light chain variable region of the first or the second polypeptide of the diabody. In some embodiments, the vector comprises a polynucleotide sequence encoding the first or the second polypeptide of the diabody.

In some embodiments, a vector is selected that is optimized for expression of polypeptides in CHO or CHO-derived cells, or in NSO cells. Exemplary such vectors are described, e.g., in Running Deer et al., *Biotechnol. Prog.* 20:880-889 (2004).

Host Cells

In some embodiments, the diabodies described herein may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO-S, DG44. Lec13 CHO cells, and FUT8 CHO cells; PER.C6® cells (Crucell); and NSO cells. In some embodiments, the diabodies described herein may be expressed in yeast. See, e.g., U.S. Publication No. US 2006/0270045 A1. In some embodiments, a particular eukaryotic host cell is selected based on its ability to make desired post-translational modifications to the first and/or second polypeptides of the diabodies. For example, in some embodiments, CHO cells produce polypeptides that have a higher level of sialylation than the same polypeptide produced in 293 cells.

Introduction of one or more nucleic acids into a desired host cell may be accomplished by any method, including but not limited to, calcium phosphate transfection, DEAE-dextran mediated transfection, cationic lipid-mediated transfection, electroporation, transduction, infection, etc. Non-limiting exemplary methods are described, e.g., in Sambrook et al., Molecular Cloning, A Laboratory Manual, $3^{rd}$ ed. Cold Spring Harbor Laboratory Press (2001). Nucleic acids may be transiently or stably transfected in the desired host cells, according to any suitable method.

The invention also provides host cells comprising any of the polynucleotides or vectors described herein. In some embodiments, the invention provides a host cell comprising an anti-PD-L1 antibody. Any host cells capable of over-expressing heterologous DNAs can be used for the purpose of isolating the genes encoding the diabody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtillis*) and yeast (such as *S. cerevisae, S. pombe*; or *K. lactis*).

In some embodiments, the diabody is produced in a cell-free system. Non-limiting exemplary cell-free systems are described, e.g., in Sitaraman et al., *Methods Mol. Biol.* 498:229-44 (2009); Spirin, *Trends Biotechnol.* 22:538-45 (2004); Endo et al., *Biotechnol. Adv.* 21:695-713 (2003).

Purification of Diabodies

The anti-PD-L1 diabodies may be purified by any suitable method known in the art. Such methods include, but are not limited to, the use of affinity matrices or hydrophobic interaction chromatography. Exemplary affinity purification methods include, but are not limited to His-tagged protein purification. Hydrophobic interactive chromatography, for example, a butyl or phenyl column, may be suitable for purifying diabodies. Ion exchange chromatography (e.g. anion exchange chromatography and/or cation exchange chromatography) may also suitable for purifying diabodies. Mixed-mode chromatography (e.g. reversed phase/anion exchange, reversed phase/cation exchange, hydrophilic interaction/anion exchange, hydrophilic interaction/cation exchange, etc.) may also be suitable for purifying diabodies.

VI. Polynucleotide, Nucleic Acid Construct, Vector, Host Cell, and Culture Medium Polynucleotide In some embodiments, there is provided a polynucleotide encoding any one of diabodies described herein or a portion thereof. In some embodiments, there is provided a polynucleotide prepared using any one of the methods as described herein.

In some embodiments, the polynucleotide is a DNA. In some embodiments, the polynucleotide is an RNA. In some embodiments, the RNA is an mRNA. In some embodiments, the polynucleotide comprises a nucleic acid sequence having at least about 80% (such as at least about any one of 80%, 85%, 90%, 95%, 96%, 97%, 98%, or 99%) sequence identity to the nucleic acid sequence of any one of SEQ ID Nos: 2, 4, 6, 8, 10, 12, 14, 16, 18, and 20.

Nucleic Acid Construct

In some embodiments, there is provided a nucleic acid construct comprising any one of the polynucleotides described herein. In some embodiments, there is provided a nucleic acid construct prepared using any method described herein.

In some embodiments, the nucleic acid construct further comprises a promoter operably linked to the polynucleotide. In some embodiments, the polynucleotide corresponds to a gene, wherein the promoter is a wild-type promoter for the gene.

Vector

In some embodiments, there is provided a vector comprising any nucleic acid construct described herein. In some embodiments, there is provided a vector prepared using any method described herein.

In some embodiments, the vector is an expression vector.

In some embodiments, the vector is selected from the group consisting of a plasmid, bacteriophage, cosmid, S factor, retroelement, retrovirus, virus, artificial chromosome (e.g., YAC, BAC or MAC), mini chromosome and a chromosome.

Host Cell

In some embodiments, there is provided a host cell comprising any polypeptide, nucleic acid construct and/or vector described herein. In some embodiments, there is provided a vector prepared using any method described herein.

In some embodiments, the host cell is capable of producing any anti-PD-L1 diabody described herein under a fermentation condition.

In some embodiments, the host cell is a prokaryotic cell. In some embodiments, the host cell is a bacterial cell (e.g., E. coli cells). In some embodiments, the host cell is a eukaryotic cell. In some embodiments, the host cell is a yeast cell. In some embodiments, the host cell is an animal cell. In some embodiments, the host cell is a mammalian cell. In some embodiments, the host cell is a CHO cell.

Culture Medium

In some embodiments, there is provided a culture medium comprising any diabody, polynucleotide, nucleic acid construct, vector, and/or host cell described herein. In some embodiments, there is provided a culture medium prepared using any method described herein.

In some embodiments, the medium comprises hypoxanthine, aminopterin, and/or thymidine (e.g., HAT medium). In some embodiments, the medium does not comprise serum. In some embodiments, the medium comprises serum. In some embodiments, the medium is a D-MEM or RPMI-1640 medium.

VII. Compositions, Kits and Articles of Manufacture

Also provided herein are compositions (such as formulations) comprising any one of the diabodies and/or a labeling agent (e.g., a radionuclide compound) described herein, nucleic acid encoding any one of the diabodies, vector comprising the nucleic acid encoding any one of the diabodies, or host cells comprising the nucleic acid or vector.

Suitable formulations of anti-PD-L1 diabodies and/or a labeling agent (e.g., a radionuclide compound) described herein can be obtained by mixing the antibody agents (such as anti-PD-L1 antibody agents) and/or a labeling agent (e.g., a radionuclide compound) having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propylparaben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Lyophilized formulations adapted for subcutaneous administration are described in WO97/04801. Such lyophilized formulations may be reconstituted with a suitable diluent to a high protein concentration and the reconstituted formulation may be administered subcutaneously to the individual to be imaged, diagnosed, or treated herein.

The formulations to be used for in vivo administration must be sterile. This is readily accomplished by, e.g., filtration through sterile filtration membranes.

In some embodiments, there is provided a kit comprising any of the diabodies described herein and a chelating agent. In some embodiments, the kit further comprises a labeling agent (such as radionuclide).

Also provided are kits that comprise any one of the anti-PD-L1 diabody or diabody agents and/or a labeling agent (e.g., radionuclide compound) described herein. The kits may be useful for any of the methods of imaging, diagnosis and treatment described herein.

In some embodiments, there is provided a kit comprising an anti-PD-L1 diabody specifically binding PD-L1, and a conjugation moiety (e.g., TCO or Tz).

In some embodiments, there is provided a kit comprising a labeling agent comprising a label (e.g., a radionuclide, e.g., $^{68}$Ga), and a conjugation moiety (e.g., TCO or Tz). In some embodiments, the conjugation moiety further comprises a chelating agent (e.g., NOTA, DOTA or derivatives thereof) that chelates the radionuclide.

In some embodiments, the kit further comprises a device capable of delivering the diabody or diabody agent and/or the labeling agent. One type of device, for applications such as parenteral delivery, is a syringe that is used to inject the composition into the body of a subject. Inhalation devices may also be used for certain applications.

In some embodiments, the kit further comprises a therapeutic agent for treating a disease or condition, e.g., cancer, infectious disease, autoimmune disease, or metabolic disease. In some embodiments, the therapeutic agent is an inhibitor of PD-L1 or receptor thereof (e.g., PD-1). In some embodiments, the therapeutic agent is a radiolabeled molecule specifically binding PD-L1 or receptor thereof (e.g., PD-1).

The kits of the present application are in suitable packaging. Suitable packaging includes, but is not limited to, vials, bottles, jars, flexible packaging (e.g., sealed Mylar or plastic bags), and the like. Kits may optionally provide additional components such as buffers and interpretative information.

The present application thus also provides articles of manufacture. The article of manufacture can comprise a container and a label or package insert on or associated with the container. Suitable containers include vials (such as sealed vials), bottles, jars, flexible packaging, and the like. Generally, the container holds a composition, and may have a sterile access port (for example the container may be an intravenous solution bag or a vial having a stopper pierceable by a hypodermic injection needle). The label or package insert indicates that the composition is used for imaging, diagnosing, or treating a particular condition in an individual. The label or package insert will further comprise instructions for administering the composition to the individual and for imaging the individual. The label may indicate directions for reconstitution and/or use. The container holding the composition may be a multi-use vial, which allows for repeat administrations (e.g. from 2-6 administrations) of the reconstituted formulation. Package insert refers to instructions customarily included in commercial packages of diagnostic products that contain information about the indications, usage, dosage, administration, contraindications and/or warnings concerning the use of such diagnostic products. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kits or article of manufacture may include multiple unit doses of the compositions and instructions for use, packaged in quantities sufficient for storage and use in pharmacies, for example, hospital pharmacies and compounding pharmacies.

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

Exemplary Embodiments

1. An isolated anti-PD-L1 diabody comprising a first polypeptide and a second polypeptide, wherein the first polypeptide and the second polypeptide each comprises a heavy chain variable region ($V_H$) and a light chain variable region ($V_L$), wherein: a) the $V_H$ comprises an HC-CDR1 comprising the amino acid sequence of SEQ ID NO: 1, an HC-CDR2 comprising the amino acid sequence of SEQ ID NO: 6, and an HC-CDR3 comprising the amino acid sequence of any one of SEQ ID NO: 11, or a variant thereof comprising up to a total of about 5 amino acid substitutions in the HC-CDRs; and b) the $V_L$ comprises an LC-CDR1 comprising the amino acid sequence of SEQ ID NO: 14, an LC-CDR2 comprising the amino acid sequence of SEQ ID NO: 17, and an LC-CDR3 comprising the amino acid sequence of any one of SEQ ID NO: 20, or a variant thereof comprising up to a total of about 5 amino acid substitutions in the LC-CDRs.

2. The diabody of embodiment 1, wherein: a) the $V_H$ comprises an HC-CDR1 comprising the amino acid sequence of SEQ ID NO: 1, an HC-CDR2 comprising the amino acid sequence of SEQ ID NO: 6, and an HC-CDR3 comprising the amino acid sequence of SEQ ID NO: 11; and b) the $V_L$ comprises an LC-CDR1 comprising the amino acid sequence of SEQ ID NO: 14, an LC-CDR2 comprising the amino acid sequence of SEQ ID NO: 17, and an LC-CDR3 comprising the amino acid sequence of SEQ ID NO: 20.

3. An isolated anti-PD-L1 diabody comprising a first polypeptide and a second polypeptide, wherein the first polypeptide and the second polypeptide each comprises a heavy chain variable region ($V_H$) and a light chain variable region ($V_L$), and wherein a) the $V_H$ and the $V_L$ of the first polypeptide, b) the $V_H$ and the $V_L$ of the second polypeptide, c) the $V_H$ of the first polypeptide and the $V_L$ of the second polypeptide, or d) the $V_H$ of the second polypeptide and the $V_L$ of the first polypeptide form a binding domain that specifically binds to PD-L1 competitively with an anti-PD-L1 antibody comprising a second heavy chain variable region ($V_{H-2}$) and a second light chain variable region ($V_{L-2}$), wherein: a) the $V_{H-2}$ comprises an HC-CDR1 comprising the amino acid sequence of SEQ ID NO: 1, an HC-CDR2 comprising the amino acid sequence of SEQ ID NO: 6, and an HC-CDR3 comprising the amino acid sequence of SEQ ID NO: 11; and b) the $V_{L-2}$ comprises an LC-CDR1 comprising the amino acid sequence of SEQ ID NO: 14, an LC-CDR2 comprising the amino acid sequence of SEQ ID NO: 17, and an LC-CDR3 comprising the amino acid sequence of SEQ ID NO: 20.

4. An isolated anti-PD-L1 diabody comprising a first polypeptide and a second polypeptide, wherein the first polypeptide and the second polypeptide each comprises a heavy chain variable region ($V_H$) and a light chain variable region ($V_L$), wherein: a) the $V_H$ comprises a HC-CDR1, a HC-CDR2, and a HC-CDR3, respectively comprising the amino acid sequences of a CDR1, a CDR2, and a CDR3 within a second heavy chain variable region ($V_{H-2}$) having the sequence set forth in any of SEQ ID NOs: 22-24; and b) the $V_L$ comprises a LC-CDR1, a LC-CDR2, and a LC-CDR3, respectively comprising the amino acid sequences of a CDR1, a CDR2, and a CDR3 within a second light chain variable region ($V_{L-2}$) having the sequence set forth in any of SEQ ID NOs: 25-27.

5. The diabody of any one of embodiments 1-4, wherein the first polypeptide and the second polypeptide are linked via a covalent bond.

6. The diabody of embodiment 5, wherein the covalent bond comprises a covalent bond between the $V_H$ of the first polypeptide and the $V_L$ of the second polypeptide, and/or a covalent bond is between the $V_L$ of the first polypeptide and the $V_H$ of the second polypeptide.

7. The diabody of any one of embodiments 1-6, wherein the first polypeptide and the second polypeptide are linked via two or more covalent bonds.

8. The diabody of embodiment 7, wherein the two or more covalent bonds comprise a) a first covalent bond between the $V_H$ of the first polypeptide and the $V_L$ of the second polypeptide; and b) a second covalent bond between the $V_H$ of the first polypeptide and the $V_L$ of the second polypeptide.

9. The diabody of any one of embodiments 5-8, wherein the covalent bond comprises a disulfide bond.

10. The diabody of embodiment 7, wherein the two or more covalent bonds comprise at least two disulfide bonds.

11. The diabody of embodiment 10, wherein the at least two disulfide bonds comprise a) a first disulfide bond between the $V_H$ of the first polypeptide and the $V_L$ of the second polypeptide; and b) a second disulfide bond between the $V_H$ of the first polypeptide and the $V_L$ of the second polypeptide.

12. The diabody of any one of embodiments 9-11, wherein the disulfide bond or one of the at least two disulfide bonds is formed by a) a cysteine residue in a HC-FR2 of the first polypeptide and a cysteine residue in a LC-FR4 of the second polypeptide, and/or b) a cysteine residue in a LC-FR4 of the first polypeptide and a cysteine residue in a HC-FR2 of the second polypeptide.

13. The diabody of any one of embodiments 1-12, wherein the $V_H$ in the first polypeptide and/or the second polypeptide comprises a G44C mutation or a Q105C mutation according to the Kabat numbering system.

14. The diabody of any one of embodiments 1-13, wherein the $V_L$ in the first polypeptide and/or the second polypeptide comprises a Q100C mutation or an A43C mutation according to the Kabat numbering system.

15. The diabody of any one of embodiments 1-14, wherein the $V_H$ in the first polypeptide and the second polypeptide each comprises a G44C mutation, and wherein the $V_L$ in the first polypeptide and the second polypeptide each comprises a Q100C mutation, wherein the G44C in the $V_H$ of the first polypeptide and the Q100C in the $V_L$ of the second polypeptide form a first disulfide bond, and wherein the Q100C in the $V_L$ of the first polypeptide and the G44C in the $V_H$ of the second polypeptide form a second disulfide bond.

16. The diabody of any one of embodiments 1-14, wherein the $V_H$ in the first polypeptide and the second polypeptide each comprises a Q105C mutation, and wherein the $V_L$ in the first polypeptide and the second polypeptide each comprises an A43C mutation.

17. The diabody of any one of embodiments 1-16, wherein the $V_H$ and the $V_L$ of the first polypeptide are fused to each other via a peptide linker.

18. The diabody of any one of embodiments 1-17, wherein the $V_H$ and the $V_L$ of the second polypeptide are fused to each other via a peptide linker.

19. The diabody of embodiment 17 or embodiment 18, wherein the peptide linker has a length of about one to thirty amino acids.

20. The diabody of any one of embodiments 17-19, wherein the peptide linker comprises the amino acid sequence of any one of SEQ ID NOs: 28-34.

21. The diabody of any one of embodiments 1-20, wherein the first polypeptide or the second polypeptide further comprises a signal peptide fused to the N-terminal of the polypeptide.

22. The diabody of embodiment 21, wherein the signal peptide comprises the amino acid sequence of SEQ ID NO: 35.

23. The diabody of any one of embodiments 1-22, wherein the $V_H$ comprises the amino acid sequence of any one of SEQ ID NOs: 22-24.

24. The diabody of any one of embodiments 1-23, wherein the $V_L$ comprises the amino acid sequence of any one of SEQ ID NOs: 25-27.

25. The diabody of any one of embodiments 1-24, wherein the first polypeptide and/or the second polypeptide further comprises a tag.

26. The diabody of embodiment 25, wherein the tag is fused to the C-terminal of the first polypeptide and/or the second polypeptide.

27. The diabody of embodiment 25 or embodiment 26, wherein the tag comprises a His-tag.

28. The diabody of any one of embodiments 25-27, wherein the tag is fused to the polypeptide via a second linker.

29. The diabody of embodiment 28, wherein the second linker has a length of about four to fifteen amino acids.

30. The diabody of embodiment 28 or embodiment 29, wherein the second linker comprises an amino acid sequence of GGGGS (SEQ ID NO: 56).

31. The diabody of any one of embodiments 1-30, wherein the first polypeptide and/or the second polypeptide comprises the amino acid sequence of any one of SEQ ID NOs: 36-43.

32. A pharmaceutical composition comprising the diabody of any one of embodiments 1-31, and a pharmaceutical acceptable carrier.

33. A polynucleotide encoding the diabody of any one of embodiments 1-31.

34. A nucleic acid construct, comprising the polynucleotide of embodiment 33, optionally further comprising a promoter in operative connection with the polynucleotide.

35. A vector comprising the nucleic acid construct of embodiment 34.

36. An isolated host cell comprising the polynucleotide according to embodiment 33, the nucleic acid construct according embodiment 34, or the vector according to embodiment 35.

37. A culture medium comprising the diabody of any one of embodiments 1 to 31, the polynucleotide according to embodiment 33, the nucleic acid construct according embodiment 34, the vector according to embodiment 35, or the host cell according to embodiment 36.

38. A method of producing an anti-PD-L1 diabody, comprising: a) culturing the isolated host cell of embodiment 36 under conditions effective to express the diabody; and b) obtaining the expressed diabody from the host cell.

39. A method of determining the distribution of PD-L1 in an individual, comprising: a) administering to the individual an imaging agent comprising the diabody of any one of embodiments 1-31 labeled with a radionuclide; and b) imaging the imaging agent in the individual with a non-invasive imaging technique.

40. A method of diagnosing an individual having a disease or condition, comprising: a) determining the distribution of PD-L1 in the individual using the method of embodiment 39; and b) diagnosing the individual as positive for PD-L1 if signal of the imaging agent is detected at a tissue of interest, or diagnosing the individual as negative for PD-L1 if signal of the imaging agent is not detected at a tissue of interest.

41. A method of treating an individual having a disease or condition, comprising: a) diagnosing the individual using the method of embodiment 40; and b) administering to the individual an effective amount of a therapeutic agent targeting PD-L1, if the individual is diagnosed as positive for PD-L1.

42. A method of treating an individual having a disease or condition, comprising administering to the individual an effective amount of the diabody of any one of embodiments 1-31 or the pharmaceutical composition of embodiment 32.

43. An imaging agent comprising the diabody of any one of embodiments 1-31 labeled with a radionuclide.

44. A method of preparing an imaging agent targeting PD-L1, comprising: a) conjugating a chelating compound to the diabody of any one of embodiments 1-31 to provide an anti-PD-L1 diabody conjugate; b) contacting a radionuclide with the anti-PD-L1 diabody conjugate, thereby providing the imaging agent.

45. A kit comprising: a) the diabody of any one of embodiments 1-31; b) a chelating agent.

46. The kit of embodiment 45, further comprising a radionuclide.

47. A method of determining the distribution of PD-L1 in an individual, comprising: administering to the individual an effective amount of a diabody agent comprising a diabody of any one of embodiments 1-31 and a first conjugation moiety; subsequently administering to the individual an effective amount of a radionuclide compound comprising a radionuclide and a second conjugation moiety, wherein the first conjugation moiety and the second conjugation moiety are conjugated to each other in vivo to provide an imaging agent; and imaging the imaging agent in the individual with a non-invasive imaging technique.

48. The method of embodiment 47, wherein the first conjugation moiety and the second conjugation moiety each comprise a member of a click chemistry pair, and are conjugated to each other via click chemistry.

EXAMPLES

The examples below are intended to be purely exemplary of the invention and should therefore not be considered to limit the invention in any way. The following examples and detailed description are offered by way of illustration and not by way of limitation.

Example 1. Generation of Anti-hPD-L1 scFv

Schematic diagrams of the construct designs for anti-hPD-L1 scFvs is shown in FIG. 1. Specifically, fragments containing $V_H$ and $V_L$ antigen binding domains from the humanized anti-hPD-L1 antibody and a peptide linker in between were artificially synthesized. See construct A in FIG. 1. In addition, single chain disulfide-stabilized Fv fragments (sc-dsFvs) were also constructed by introducing single mutations at $V_H44/V_L100$ or $V_H105/V_L43$ (according to the Kabat numbering system). See construct B and construct C in FIG. 1. See Table 3 for $V_H$ and $V_L$ sequences of the three constructs. The fragments containing $V_H$ and $V_L$ also included restriction endonuclease HindIII and EcoRI recognition sites at the 5' and 3' ends, respectively, as well as a His tag sequence fused to the C-terminus via a short peptide linker. The fused heavy chain and light chain were then cloned into the corresponding HindIII and EcoRI recognition sites of the PXC17.4 expression vector.

TABLE 3

Sequences of anti-PD-L1 scFvs

| | Sequences | SEQ ID NO |
|---|---|---|
| Construct A $V_H$ | QVQLVQSGAEVKKPGASVKV SCKASGFNIKDTYMYWVRQA PGQGLEWMGRIDPANDNTKY AQKFQGRVTITADTSTSTAY MELSSLRSEDTAVYYCARAK NLLNYFDYWGQGTLVTVSS | 22 |
| Construct A $V_L$ | DIQMTQSPSSLSASVGDRVT ITCRASQEISGYLSWLQQKP GKAPKRLIYATSTLQSGVPS RFSGSRSGTDYTLTISSLQP EDFATYYCLQYAIYPLTFGQ GTKLEIKR | 25 |
| CDR-H1 | GFNIKDTY | 1 |
| CDR-H2 | IDPANDNT | 6 |
| CDR-H3 | ARAKNLLNYFDY | 11 |
| CDR-L1 | QEISGY | 14 |
| CDR-L2 | ATS | 17 |
| CDR-L3 | LQYAIYPLT | 21 |
| Construct B $V_H$ (G44C) | QVQLVQSGAEVKKPGASVKV SCKASGFNIKDTYMYWVRQA PGQC LEWMGRIDPANDNTKY AQKFQGRVTITADTSTSTAY MELSSLRSEDTAVYYCARAK NLLNYFDYWGQGTLVTVSS | 23 |

TABLE 3-continued

Sequences of anti-PD-L1 scFvs

| | Sequences | SEQ ID NO |
|---|---|---|
| Construct B $V_L$ (Q100C) | DIQMTQSPSSLSASVGDRVT ITCRASQEISGYLSWLQQKP GKAPKRLIYATSTLQSGVPS RFSGSRSGTDYTLTISSLQP EDFATYYCLQYAIYPLTFGC GTKLEIKR | 26 |
| Construct C $V_H$ (Q105C) | QVQLVQSGAEVKKPGASVKV SCKASGFNIKDTYMYWVRQA PGQGLEWMGRIDPANDNTKY AQKFQGRVTITADTSTSTAY MELSSLRSEDTAVYYCARAK NLLNYFDYWGCGTLVTVSS | 24 |
| Construct C $V_L$ (A43C) | DIQMTQSPSSLSASVGDRVT ITCRASQEISGYLSWLQQKP GKCPKRLIYATSTLQSGVPS RFSGSRSGTDYTLTISSLQP EDFATYYCLQYAIYPLTFGQ GTKLEIKR | 27 |

Example 2. Anti-PD-L1 Diabody Construction and Expression

Figure 2:
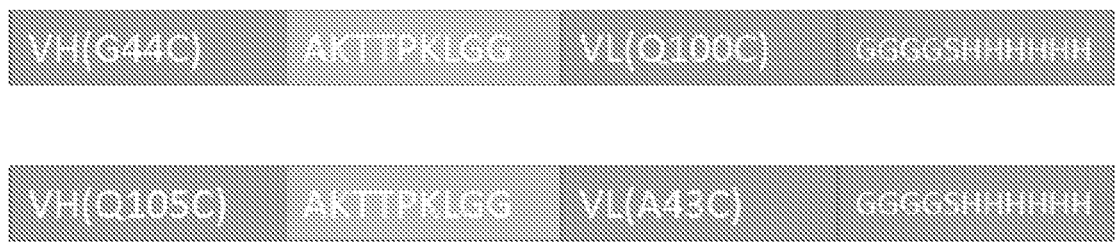
FIG. 2 shows a schematic diagram of monomer forms corresponding to the exemplary anti-PD-L1 diabodies (SEQ ID NO: 28 (AKTTPKLGG); SEQ ID NO: 57 (GGGGSHHHHHH)).

A scheme of the monomer forms corresponding to the diabody constructions was shown in FIG. 2. Specifically, $V_H$ (G44C) and $V_L$ (Q100C) gene fragments were generated by PCR from construct B in FIG. 1. $V_H$ (Q105C) and $V_L$ (A43C) gene fragments were generated by PCR from construct C in FIG. 1. $V_H$ (G44C) and $V_L$ (Q100C) gene fragments were fused together by overlapping PCR and named as H44/L100; $V_H$ (Q105C) and $V_L$ (A43C) gene fragments were fused together by overlapping PCR and named as H105/L43. See Table 4 for the PCR primers used during PCR and overlapping PCR.

TABLE 4

PCR Primers

| Name | Sequence |
|---|---|
| F-$V_H$ | 5' AAGCTTGCCACCATGGA CCCCAAGGGCAGCCTG 3' (SEQ ID NO: 52) |
| R-$V_H$ (overlap) | 5' GTTTCGGGGTGGTTTTC GCTGAGGAGACTGTGACAAG 3' (SEQ ID NO: 53) |
| F-$V_L$ (overlap) | 5' CCACCCCGAAACTGGGCG GCGACATCCAGATGACCCAG 3' (SEQ ID NO: 54) |
| R-$V_L$ | 5' GAATTCTTATCAATGGTG ATGGTG 3' (SEQ ID NO: 55) |

H44/L100 and H105/L43 PCR products were digested by HindIII and EcoRI respectively. Digested products were inserted into PXC17.4 expression vector. The expression of the two products was evaluated in CHO cells five days after transient transfection. Cell culture supernatants were harvested and protein products generated from the expression of H44/L100 or H105/L43 digested PCR products were purified by CaptoL affinity column. The expression results were shown in Table 5. The purified protein for H44/L100 was analyzed for the ratio of the diabody form and the monomer form. About 85% of the total protein is in the diabody form. The diabody form was purified by size exclusion chromatography or ion exchange chromatograph with 100% purity.

TABLE 5

| Product in 30 ml culture medium | Amount of purified protein (diabody and monomer) |
|---|---|
| H44/L100 | ~5 mg |
| H105/L43 | <50 μg |

Example 3. PD-L1 Binding Affinity of Anti-PD-L1-Diabody and Anti-PD-L1 scFv

Anti-PD-L1 diabody (H44/L100) generated as illustrated in Example 2, anti-PD-L1 scFv generated from construct A in FIG. 1, and an anti-PD-L1 IgG antibody (with the same CDRs) were tested for their PD-L1 binding affinity. As shown in Table 6, the diabody form has an unexpectedly higher binding affinity to PD-L1 than the scFv form.

TABLE 6

| Sample | $K_D$ range (M) | Relatively binding activity |
|---|---|---|
| scFv form | $5 \times 10^{-8} - 10^{-7}$ | + |
| Diabody form | $10^{-10} - 10^{-9}$ | ++++ |
| IgG form | $10^{-11} - 10^{-10}$ | +++++ |

Example 4. Coupling of Anti-PD-L1-ScFv and NOTA and Labeling NOTA-Anti-PD-L1 scFv with $^{68}$Ga NOTA was coupled with the anti-PD-L1 scFv generated from construct A in FIG. 1. After coupling, the anti-PD-L1 scFv was labeled with the isotope $^{68}$Ga. Specifically, a total volume of 400 μL anti-PD-L1-scFv was added into 100 μL 0.05M NaHCO$_3$—Na$_2$CO$_3$ buffer with a pH of 8.7, followed by centrifugation at 16000 rpm for 20 minutes. The supernatant was removed to achieve a final volume of 100 μL. The above steps were repeated one more time and the final solution was transferred to a 1.5 mL centrifuge tube. A volume of 2.75 μL of p-SCN-Bn-NOTA was then added to the centrifuge tube, followed by incubation for one hour at 37° C.

The scFv/NOTA solution was added to a NAP-5 column that has been pre-balanced with PBS. The column was then washed with 0.4 mL of PBS and eluted with 0.5 mL of PBS. The eluate was aliquoted into portions with a volume of 0.05 mL and stored at −20° C.

$^{68}$Ga was eluted to 0.05N HCl with a final concentration of 2.4 mCi/1 mL HCl. A volume of 93 μL of 1.25M sodium acetate was then added to adjust the pH of $^{68}$Ga solution to 4.0. A volume of 50 μL of NOTA-anti-PD-L1 scFv (0.05 mg/ml) was mixed with 350 μL $^{68}$Ga solution, followed by incubation for 10 min at 25° C. Labeling rate was determined by development on a thin layer chromatography paper using 0.1M sodium citrate as a developing solvent. NAP-5 column was equilibrated with PBS, and then a volume of 400 μL of the labeled product was added. After filtration, 400 μL PBS was not collected. Then 400 μL PBS was added and the filtrate was collected. The radiochemical purity of the product was determined by development on an instant thin-layer chromatography-silicone gel (ITLC-SG) using 0.1M sodium citrate as a developing solvent. The origin corresponded to the product and the developing solvent front corresponded to free $^{68}$Ga.

Figure 3A:
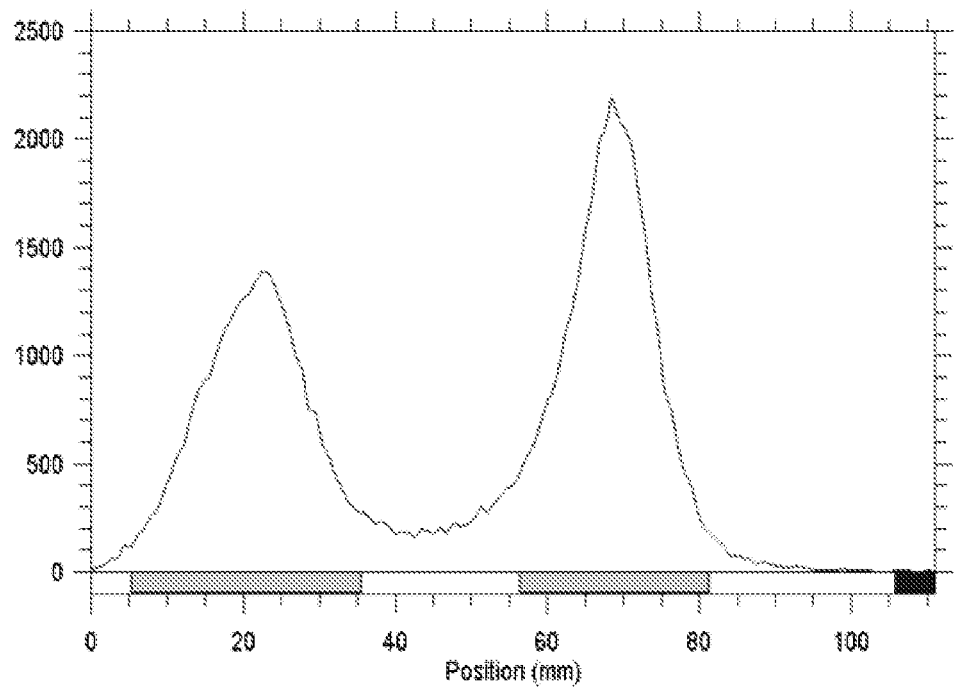
FIGS. 3A-3B show the yield of $^{68}$Ga-NOTA-anti-PD-L1-scFv (FIG. 3A) and the radiochemical purity of the scFv after purification (FIG. 3B) as measured using instant thin layer chromatography on Silica Gel.
Figure 3B:
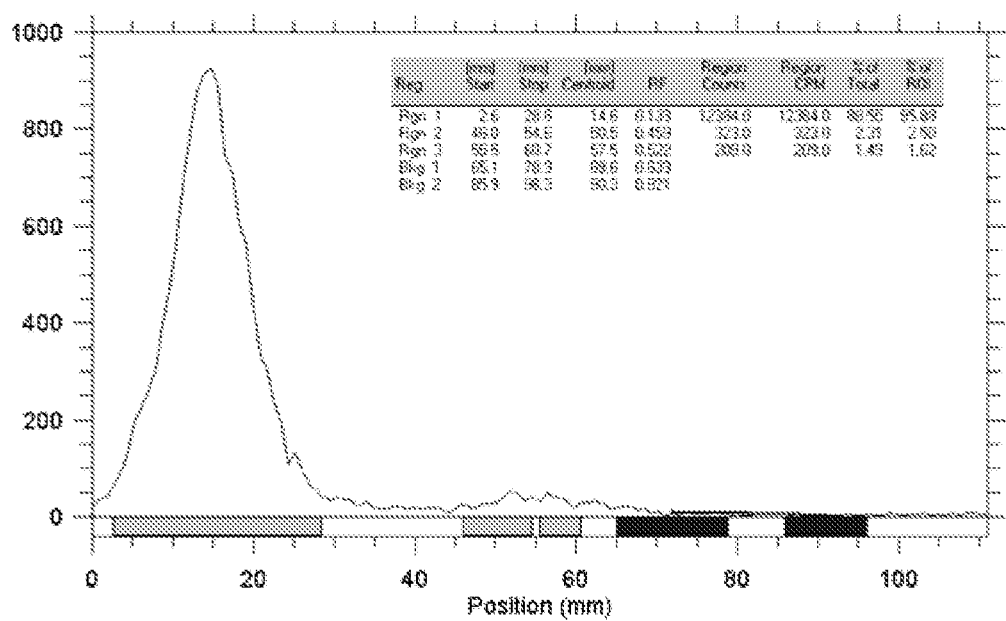

As shown in FIGS. 3A-3B, labeling rate of $^{68}$Ga-NOTA-anti-PD-L1-scFv was 66.9%. After purification, the radiochemical purity was 95.9%.

Example 5. Cell Binding of $^{68}$Ga-Anti-PD-L1-ScFv

Figure 4A:
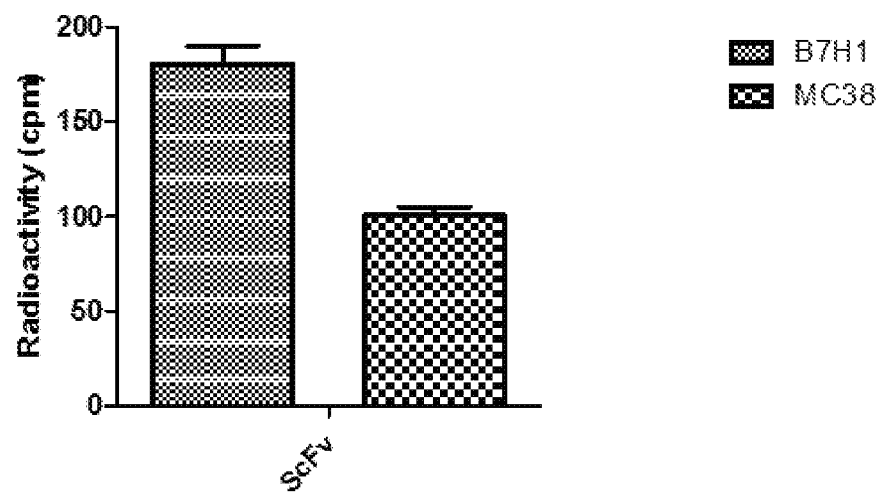
FIGS. 4A-4B show the binding of $^{68}$Ga-NOTA-anti-PD-L1-scFv to MC38 or MC38-B7H1 cells without the blocking of unlabeled anti-PD-L1 scFv (FIG. 4A) or with the blocking of unlabeled anti-PD-L1 scFv (FIG. 4B)

MC38 and MC38-B7H1 cells were digested with trypsin and then cultivated and counted. Each type of cells was plated into 24-well plates with $2.5 \times 10^5$ cells/0.5 mL per well. After overnight incubation at 37° C., $^{68}$Ga-NOTA-anti-PD-L1-ScFv was added to each type of cell at a final concentration of 36 nM and the cells were kept at 37° C. for 0.5 hour. Subsequently, ice chilled PBS was added to wash the cells for three times. The cells were then lysed with 0.1M NaOH. Cell lysate was collected and counted. Data analysis and plotting were conducted using the GraphPad Prism software. The binding of $^{68}$Ga-NOTA-anti-PD-L1-ScFv to MC38-B7H1 cells or MC38 cells were shown in FIG. 4A.

Figure 4B:
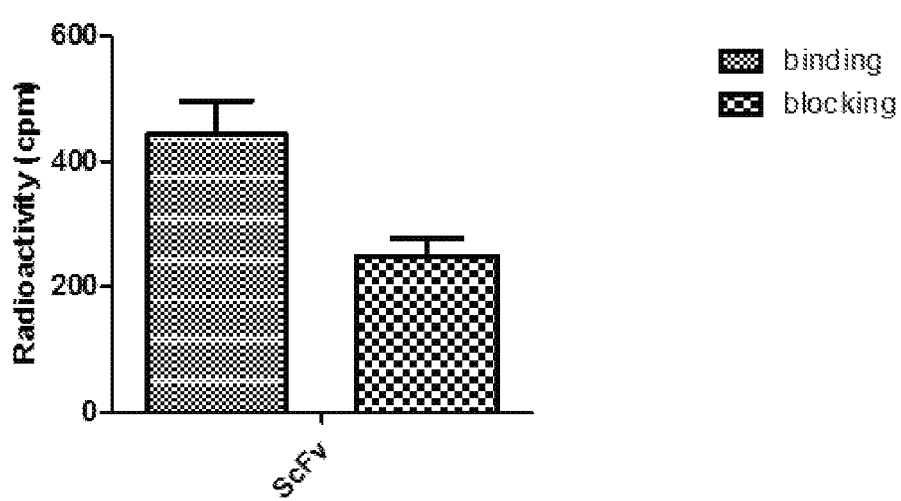

In a separate experiment, MC38-B7H1 cells were digested with trypsin and then cultivated and counted. Cells were plated into 24-well plates with $2.5 \times 10^5$ cells/0.5 mL per well. After overnight incubation at 37° C., $^{68}$Ga-NOTA-anti-PD-L1-ScFv was added to the cell at a final concentration of 36 nM in the presence or absence of an unlabeled anti-PD-L1 scFv with a final concentration of 1.8 μM. The cells were then kept at 37° C. for 0.5 h. Subsequently, ice chilled PBS was added to wash the cells for three times. The cells were then lysed with 0.1M NaOH. Cell lysate was collected and counted. Data analysis and plotting were conducted using the GraphPad Prism software. As shown in FIG. 4B, the binding of $^{68}$Ga-NOTA-anti-PD-L1-ScFv to MC38-B7H1 cells was blocked by the unlabeled anti-PD-L1-scFv significantly.

Example 6. In Vivo Imaging of $^{68}$Ga-Anti-PD-L1-scFv

A total of ten male mice of about six to eight weeks old were administered with MC38 cells and MC38-B7H1 cells simultaneously. Specifically, 0.4 million MC38 cells were injected into the left flanks of the mice and 0.4 million MC38-B7H1 cells were injected into right flanks. Seven days after the injection, tumors grew to a size of about 0.5 cm in diameter. The mice were then used for in vivo imaging. Five mice were administered with 40 μCi $^{68}$Ga-anti-anti-PD-L1-scFv via the tail vein. The other five mice were concurrently administered with 40 μCi $^{68}$Ga-anti-anti-PD-L1-scFv and an unlabeled cold anti-PD-L1 antibody at a mole ratio of 1:50. The mice were imaged at one hour and two hours after the injection.

Figure 5A:
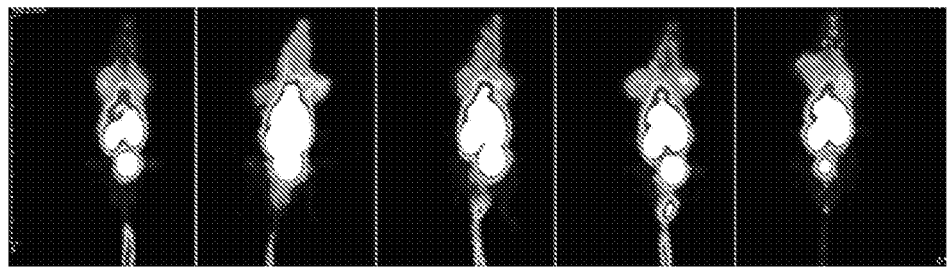
FIGS. 5A-5B show in vivo imaging results of tumors in mice 1 hour (top panel) or 2 hours (bottom panel) after the injection of $^{68}$Ga-NOTA-anti-PD-L1-scFv without the blocking of unlabeled anti-PD-L1 scFv (FIG. 5A) or with the blocking of the unlabeled anti-PD-L1-scFv (FIG. 5B). The tumors were induced by the pre-administration of MC38 cells and MC38-B7H1 cells, respectively, into the left franks and right franks of the mice.
Figure 5A:
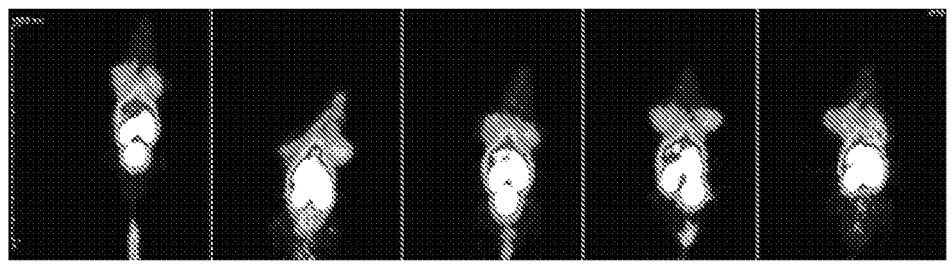
Figure 5B:
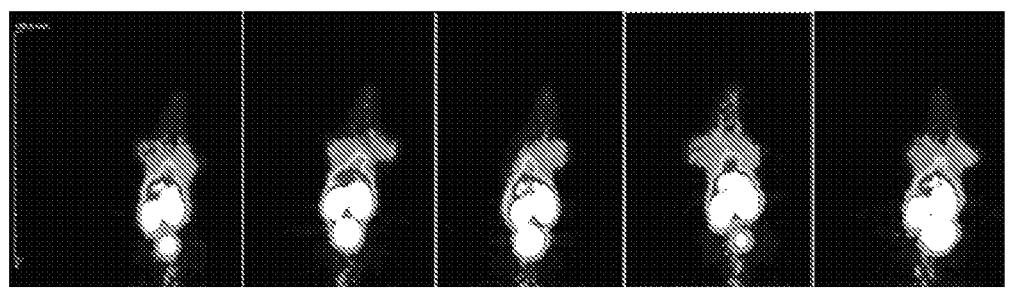
Figure 5B:
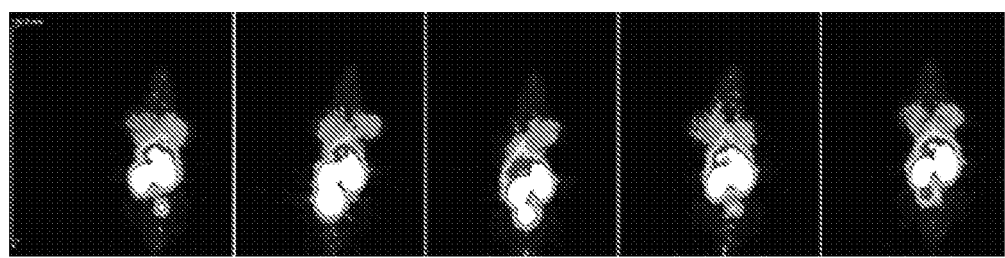

Following injection of $^{68}$Ga-NOTA-anti-PD-L1-scFv only, MC38-B7H1 tumors (right flank) were intensely stained. MC38 tumors (left flank) were weakly stained with the highest intake in kidneys. Images at 120 minutes after injection had increased sensitivity than those at 60 minutes after injection. See FIG. 5A. As shown in FIG. 5B, fifty times excessive unlabeled anti-PD-L1 antibody blocked the imaging of B7-H1 positive tumors in mice injected with both unlabeled anti-PD-L1 antibodies and $^{68}$Ga-NOTA-anti-PD-L1-scFv. See FIG. 5B.

Example 7. Coupling of Anti-PD-L1 Diabody and NOTA and $^{68}$Ga Labeling of NOTA-Anti-PD-L1-Diabody NOTA was coupled with the anti-PD-L1 diabody produced from H44/L100 products as illustrated in Example 2. After coupling, the anti-PD-L1 diabody was labeled with the isotope $^{68}$Ga. Specifically, 400 μL anti-PD-L1 diabody was added into 100 μL 0.05M NaHCO$_3$—Na$_2$CO$_3$ buffer that has a pH of 8.7, followed by centrifugation at 16000 rpm for 20 min and concentrated to 100 μL. It is then added into 400 μL 0.05M NaHCO$_3$—Na$_2$CO$_3$ buffer for centrifugation at 16000 rpm for 20 minutes. The supernatant was removed to achieve a final volume of 100 μL. The final solution was transferred to a 1.5 mL centrifuge tube. A volume of 2.75 μL of p-SCN-Bn-NOTA was then added to the centrifuge tube, followed by incubation for one hour at 37° C.

The diabody/NOTA solution was added to a NAP-5 column that has been pre-balanced with PBS. The column was then washed with 0.4 mL of PBS and eluted with 0.5 mL of PBS. The eluate was aliquoted into portions with a volume of 0.05 mL and stored at −20° C.

$^{68}$Ga was eluted to 0.05N HCl with a final concentration of 2.4 mCi/1 mL HCl. A volume of 93 μL of 1.25M sodium acetate was then added to adjust the pH of $^{68}$Ga solution to 4.0. A volume of 50 μL of NOTA-anti-PD-L1 diabody (1.0 mg/ml) was mixed with 350 μL $^{68}$Ga solution, followed by incubation for 10 min at 25° C. Labeling rate was determined by development on a thin layer chromatography paper using 0.1M sodium citrate as a developing solvent. NAP-5 column was equilibrated with PBS, and then a volume of 400 μL of the labeled product was added. After filtration, 400 μL PBS was added. Filtrate was not collected. Then 400 μL PBS was added and the filtrate was collected. The radiochemical purity of the product was determined by development on an instant thin-layer chromatography-silicone gel (ITLC-SG) using 0.1M sodium citrate as a developing solvent. The origin corresponded to the product and the developing solvent front corresponded to free $^{68}$Ga.

Figure 6A:
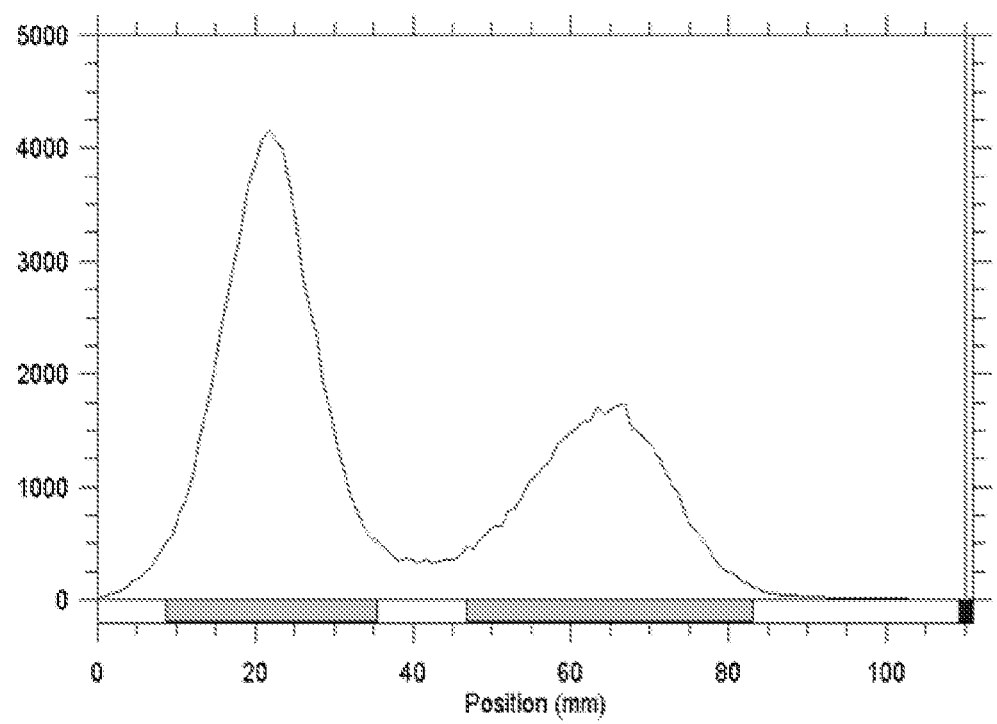
FIGS. 6A-6B show the yield of $^{68}$Ga-NOTA-anti-PD-L1 diabody (FIG. 6A) and the radiochemical purity of the diabody after purification (FIG. 6B) as measured using instant thin layer chromatography on Silica Gel.
Figure 6B:
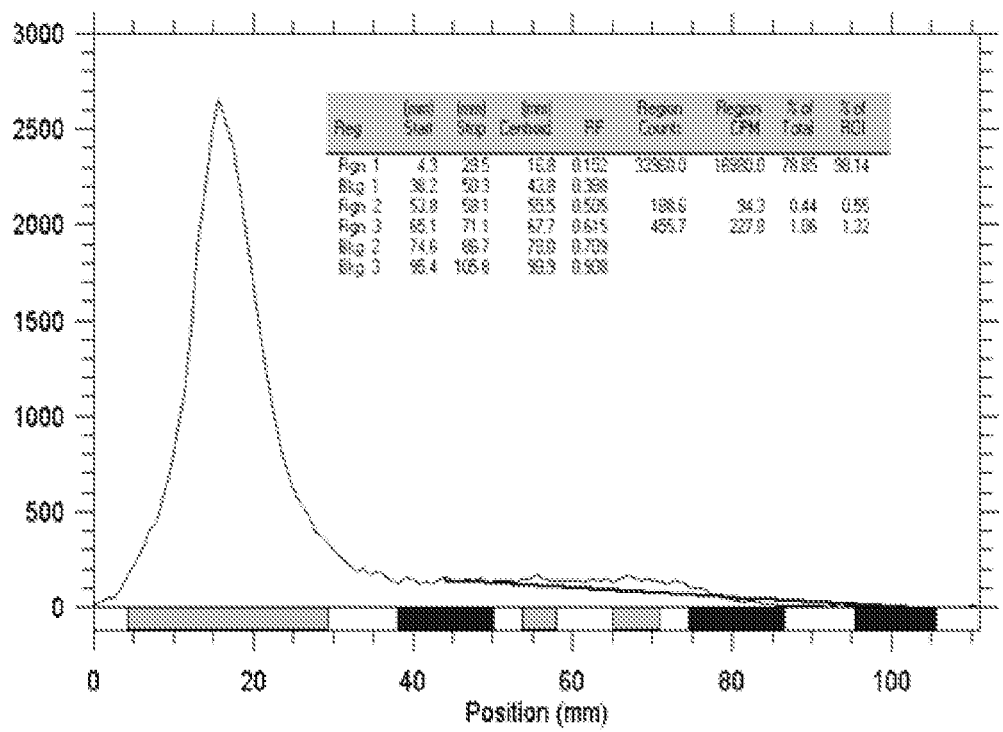

As shown in FIGS. 6A-6B, labeling rate of $^{68}$Ga-NOTA-anti-PD-L1-diabody was 62.0%. After purification, the radiochemical purity of $^{68}$Ga-NOTA-anti-PD-L1-diabody was 98.1%.

Example 8. Cell Binding Experiment for $^{68}$Ga-Anti-PD-L1-Diabody

Figure 7A:
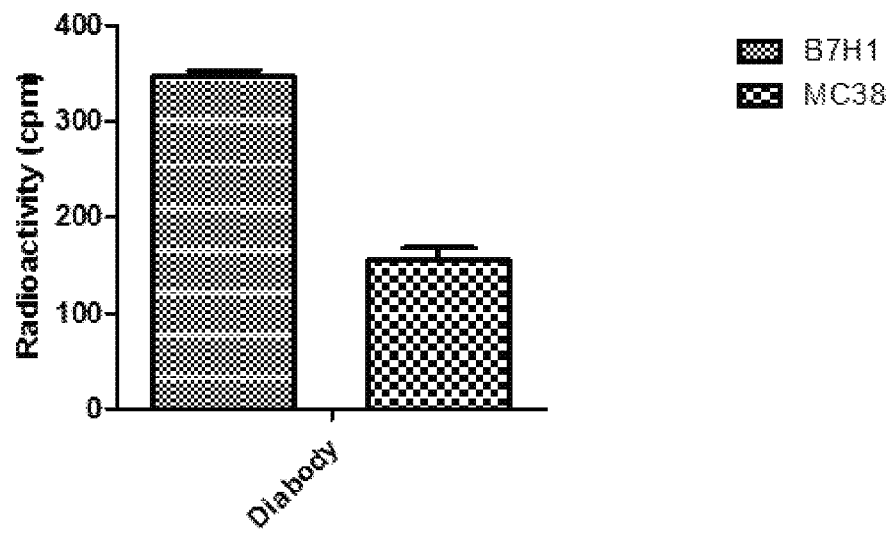
FIGS. 7A-7B show the binding of $^{68}$Ga-NOTA-anti-PD-L1-diabody to MC38 or MC38-B7H1 cells without the blocking of unlabeled anti-PD-L1 diabody (FIG. 7A) or with the blocking of unlabeled anti-PD-L1 diabody (FIG. 7B)
Figure 7B:
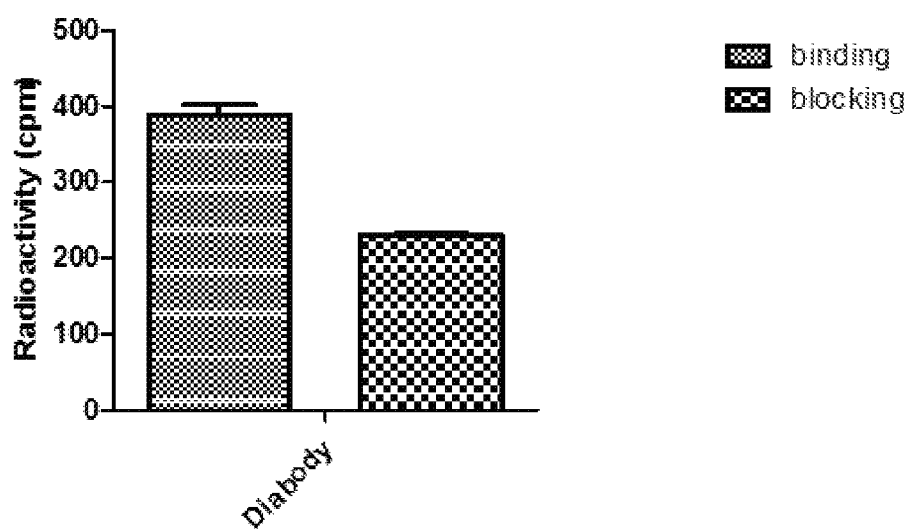

MC38 and MC38-B7H1 cells were digested with trypsin and then cultivated and counted. Each type of cells was plated into 24-well plates with 2.5×10$^5$ cells/0.5 mL per well. After overnight incubation at 37° C., $^{68}$Ga-NOTA-anti-PD-L1-diabody was added to each type of cell at a final concentration of 36 nM and the cells were kept at 37° C. for 0.5 hour. Subsequently, ice chilled PBS was added to wash the cells for three times. The cells were then lysed with 0.1M NaOH. Cell lysate was collected and counted. Data analysis and plotting were conducted using the GraphPad Prism software. As shown in FIG. 7A, the binding of $^{68}$Ga-NOTA-anti-PD-L1-diabody to MC38-B7H1 cells were higher than its binding to MC38 cells In a separate experiment, MC38-B7H1 cells were digested with trypsin and then cultivated and counted. Cells were plated into 24-well plates with 2.5×10$^5$ cells/0.5 mL per well. After overnight incubation at 37° C., $^{68}$Ga-NOTA-anti-PD-L1-diabody was added to the cell at a final concentration of 36 nM in the presence or absence of an unlabeled anti-PD-L1 diabody with a final concentration of 1.8 μM. The cells were then kept at 37° C. for 0.5 h. Subsequently, ice chilled PBS was added to wash the cells for three times. The cells were then lysed with 0.1M NaOH. Cell lysate was collected and counted. Data analysis and plotting were conducted using the GraphPad Prism software. The binding of $^{68}$Ga-NOTA-anti-PD-L1-diabody to MC38-B7H1 cells was blocked by unlabeled anti-PD-L1 diabody significantly. See FIG. 7B.

Example 9. In Vivo Imaging of $^{68}$Ga-Anti-PD-L1-Diabody

A total of ten male mice of about six to eight weeks old were administered with MC38 cells and MC38-B7H1 cells simultaneously. Specifically, 0.4 million MC38 cells were injected into the left flanks of the mice and 0.4 million MC38-B7H1 cells were injected into right flanks. Seven days after the injection, tumors grew to a size of about 0.5 cm in diameter. The mice were then used for in vivo imaging. Five mice were administered with 40 uCi $^{68}$Ga-anti-anti-PD-L1-diabody via the tail vein. The other five mice were concurrently administered with 40 uCi $^{68}$Ga-anti-anti-PD-L1-diabody and an unlabeled cold anti-PD-L1 antibody at a mole ratio of 1:50. The mice were imaged at one hour and two hours after the injection.

Figure 8A:
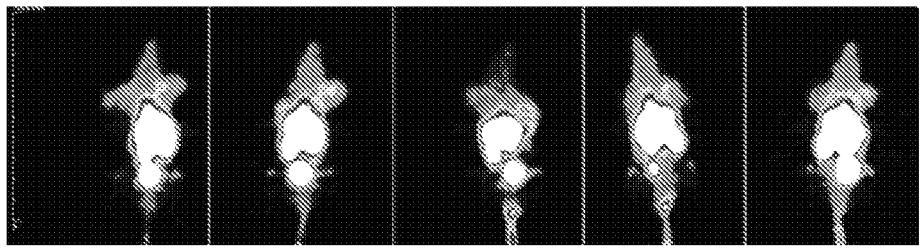
FIGS. 8A-8B show in vivo imaging results of tumors in mice 1 hour (top panel) or 2 hours (bottom panel) after the injection of $^{68}$Ga-NOTA-anti-PD-L1-diabody without the blocking of unlabeled anti-PD-L1 diabody (FIG. 8A) and with the blocking of unlabeled anti-PD-L1 diabody (FIG. 8B). The tumors were induced by the pre-administration of MC38 cells and MC38-B7H1 cells, respectively, into the left franks and right franks of the mice.
Figure 8A:
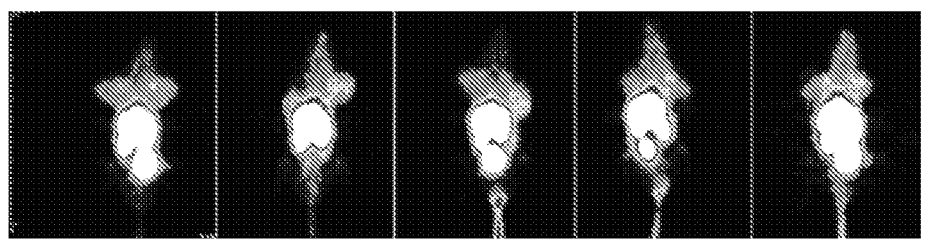
Figure 8B:
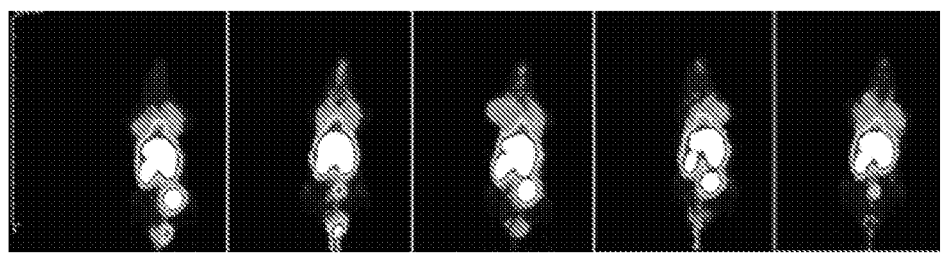
Figure 8B:
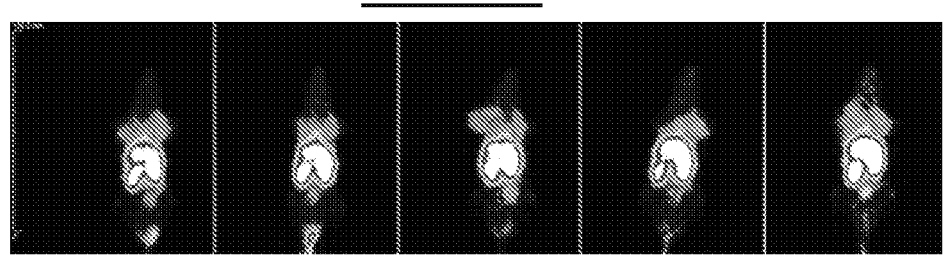

Following injection of $^{68}$Ga-NOTA-anti-PD-L1-diabody only, MC38-B7H1 tumors (right flank) were intensely stained. MC38 tumors (left flank) were weakly stained with the highest intake in kidneys. Images at 120 minutes after injection had increased sensitivity than those at 60 minutes after injection. See FIG. 8A. Fifty times excessive unlabeled anti-PD-L1 antibodies blocked the imaging of B7H1 positive tumors in mice injected with both unlabeled anti-PD-L1 antibodies and $^{68}$Ga-NOTA-anti-PD-L1 diabody. See FIG. 8B.

Figure 9:
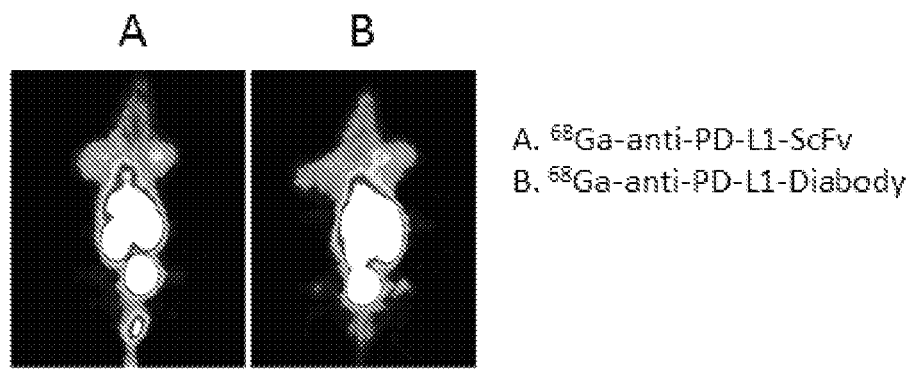
FIG. 9 shows a comparison of the imaging at one hour following the injection of $^{68}$Ga-NOTA-anti-PD-L1-scFv or $^{68}$Ga-NOTA-anti-PD-L1-diabody.

Example 10. Comparison of Imaging by $^{68}$Ga-Anti-PD-L1-scFv and $^{68}$Ga-Anti-PD-L1-Diabody Comparison of representative imaging at one hour following injection of $^{68}$Ga-anti-PD-L1-scFv, and $^{68}$Ga-anti-PD-L1-Diabody indicated that $^{68}$Ga-anti-PD-L1-Diabody was better than $^{68}$Ga-anti-PD-L1-scFv with clearer imaging. See FIG. 9. It also had higher liver intake.

The above examples at least demonstrated that $^{68}$Ga labeled diabody can be used for imaging PD-L1 positive tumors.

SEQUENCE TABLE

| SEQ ID NO | Description | Sequences |
| --- | --- | --- |
| 1 | CDR-H1 | GFNIKDTY |
| 2 | CDR-H1 (Kabat) | DTYMY |
| 3 | CDR-H1 (Chothia) | GFNIKDT |
| 4 | CDR-H1 (AbM) | GFNIKDTYMY |
| 5 | CDR-H1 (Contact) | KDTYMY |

| SEQ ID NO | Description | Sequences |
|---|---|---|
| 6 | CDR-H2 | IDPANDNT |
| 7 | CDR-H2 (Kabat) | RIDPANDNTKYAQKFQG |
| 8 | CDR-H2 (Chothia) | DPANDN |
| 9 | CDR-H2 (AbM) | RIDPANDNTK |
| 10 | CDR-H2 (Contact) | WMGRIDPANDNTK |
| 11 | CDR-H3 | ARAKNLLNYFDY |
| 12 | CDR-H3 (Kabat/Abm/Chothia) | AKNLLNYFDY |
| 13 | CDR-H3 (Contact) | ARAKNLLNYFD |
| 14 | CDR-L1 | QEISGY |
| 15 | CDR-L1 (Kabat/Abm/Chothia) | RASQEISGYLS |
| 16 | CDR-L1 (Contact) | SGYLSWL |
| 17 | CDR-L2 | ATS |
| 18 | CDR-L2 (Kabat/Abm/Chothia) | ATSTLQS |
| 19 | CDR-L2 (Contact) | RLIYATSTLQ |
| 20 | CDR-L3 (Kabat/Abm/Chothia) | LQYAIYPLT |
| 21 | CDR-L3 (Contact) | LQYAIYPL |
| 22 | $V_H$ | QVQLVQSGAEVKKPGASVKVSCKASGFNIKDTYMYWVRQAPGQGLEWMGRIDPANDNTKYAQKFQGRVTITADTSTSTAYMELSSLRSEDTAVYYCARAKNLLNYFDYWGQGTLVTVSS |
| 23 | $V_H$ (G44C) | QVQLVQSGAEVKKPGASVKVSCKASGFNIKDTYMYWVRQAPGQC LEWMGRIDPANDNTKYAQKFQGRVTITADTSTSTAYMELSSLRSEDTAVYYCARAKNLLNYFDYWGQGTLVTVSS |
| 24 | $V_H$ (Q105C) | QVQLVQSGAEVKKPGASVKVSCKASGFNIKDTYMYWVRQAPGQGLEWMGRIDPANDNTKYAQKFQGRVTITADTSTSTAYMELSSLRSEDTAVYYCARAKNLLNYFDYWGCGTLVTVSS |
| 25 | $V_L$ | DIQMTQSPSSLSASVGDRVTITCRASQEISGYLSWLQQKPGKAPKRLIYATSTLQSGVPSRFSGSRSGTDYTLTISSLQPEDFATYYCLQYAIYPLTFGQGTKLEIKR |
| 26 | $V_L$ (Q100C) | DIQMTQSPSSLSASVGDRVTITCRASQEISGYLSWLQQKPGKAPKRLIYATSTLQSGVPSRFSGSRSGTDYTLTISSLQPEDFATYYCLQYAIYPLTFGCGTKLEIKR |
| 27 | $V_L$ (A43C) | DIQMTQSPSSLSASVGDRVTITCRASQEISGYLSWLQQKPGKCPKRLIYATSTLQSGVPSRFSGSRSGTDYTLTISSLQPEDFATYYCLQYAIYPLTFGQGTKLEIKR |
| 28 | Linker | AKTTPKLGG |
| 29 | Linker (L10) | SAKTTPKLGG |
| 30 | Linker (L6) | SAKTTP |
| 31 | Linker (K6) | RADAAP |
| 32 | Linker (K9) | RADAAPTVS |
| 33 | Linker (SL) | RADAAAAGGPGS |
| 34 | Linker (LL) | RADAAAA(G4S)4 |
| 35 | Signal sequence | MDPKGSLSWRILLFLSLAFELSYG |
| 36 | $V_H$ (G44C)-Linker-$V_L$ (Q100C) | QVQLVQSGAEVKKPGASVKVSCKASGFNIKDTYMYWVRQAPGQCLEWMGRIDPANDNTKYAQKFQGRVTITADTSTSTAYMELSSLRSEDTAVYYCARAKNLLNYFDYWGQGTLVTVSSAKTTPKLGGDIQMTQSPSSLSASVGDRVTITCRASQEISGYLSWLQQKPGKAPKRLIYATSTLQSGVPSRFSGSRSGTDYTLTISSLQPEDFATYYCLQYAIYPLTFGCGTKLEIKR |
| 37 | $V_H$ (G44C)-Linker-$V_L$ (Q100C) | QVQLVQSGAEVKKPGASVKVSCKASGFNIKDTYMYWVRQAPGQCLEWMGRIDPANDNTKYAQKFQGRVTITADTSTSTAYMELSSLRSEDTAVYYCARAKNLLNYFDYWGQGTLVTVSSAKTTPKLGGDIQMTQSPSSLSASVGDRVTITCRASQEISGYLSWLQQKPGKAPKRLIYATSTLQSGVPSRFSGSRSGTDYTLTISSLQPEDFATYYCLQYAIYPLTFGCGTKLEIKRGGGGS |
| 38 | $V_H$ (Q105C)-Linker-$V_L$ (A43C) | QVQLVQSGAEVKKPGASVKVSCKASGFNIKDTYMYWVRQAPGQGLEWMGRIDPANDNTKYAQKFQGRVTITADTSTSTAYMELSSLRSEDTAVYYCARAKNLLNYFDYWGCGTLVTVSSAKTTPKLGGDIQMTQSPSSLS |

-continued

| SEQ ID NO | Description | Sequences |
|---|---|---|
| | | ASVGDRVTITCRASQEISGY LSWLQQKPGKCPKRLIYATS TLQSGVPSRFSGSRSGTDYT LTISSLQPEDFATYYCLQYA IYPLTFGQGTKLEIKR |
| 39 | $V_H$ (Q105C) -Linker- $V_L$ (A43C) | QVQLVQSGAEVKKPGASVKV SCKASGFNIKDTYMYWVRQA PGQGLEWMGRIDPANDNTKY AQKFQGRVTITADTSTSTAY MELSSLRSEDTAVYYCARAK NLLNYFDYWGCGTLVTVSSA KTTPKLGGDIQMTQSPSSLS ASVGDRVTITCRASQEISGY LSWLQQKPGKCPKRLIYATS TLQSGVPSRFSGSRSGTDYT LTISSLQPEDFATYYCLQYA IYPLTFGQ GTKLEIKRGGGGS |
| 40 | SS-$V_H$ (G44C) -Linker- $V_L$ (Q100C) | MDPKGSLSWRILLFLSLAFE LSYGQVQLVQSGAEVKKPGA SVKVSCKASGFNIKDTYMYW VRQAPGQCLEWMGRIDPAND NTKYAQKFQGRVTITADTST STAYMELSSLRSEDTAVYYC ARAKNLLNYFDYWGQGTLVT VSSAKTTPKLGGDIQMTQSP SSLSASVGDRVTITCRASQE ISGYLSWLQQKPGKAPKRLI YATSTLQSGVPSRFSGSRSG TDYTLTISSLQPEDFATYYC LQYAIYPLTFGCGTKLEIKR |
| 41 | SS-$V_H$ (G44C)- Linker- $V_L$ (Q100C) | MDPKGSLSWRILLFLSLAFE LSYGQVQLVQSGAEVKKPGA SVKVSCKASGFNIKDTYMYW VRQAPGQCLEWMGRIDPAND NTKYAQKFQGRVTITADTST STAYMELSSLRSEDTAVYYC ARAKNLLNYFDYWGQGTLVT VSSAKTTPKLGGDIQMTQSP SSLSASVGDRVTITCRASQE ISGYLSWLQQKPGKAPKRLI YATSTLQSGVPSRFSGSRSG TDYTLTISSLQPEDFATYYC LQYAIYPLTFGCGTKLEIKR GGGGS |
| 42 | SS-$V_H$ (Q105C) -Linker- $V_L$ (A43C) | MDPKGSLSWRILLFLSLAFE LSYGQVQLVQSGAEVKKPGA SVKVSCKASGFNIKDTYMYW VRQAPGQGLEWMGRIDPAND NTKYAQKFQGRVTITADTST STAYMELSSLRSEDTAVYYC ARAKNLLNYFDYWGCGTLVT VSSAKTTPKLGGDIQMTQSP SSLSASVGDRVTITCRASQE ISGYLSWLQQKPGKCPKRLI YATSTLQSGVPSRFSGSRSG TDYTLTISSLQPEDFATYYC LQYAIYPLTFGQGTKLEIKR |
| 43 | SS-$V_H$ (Q105C) -Linker- $V_L$ (A43C) | MDPKGSLSWRILLFLSLAFE LSYGQVQLVQSGAEVKKPGA SVKVSCKASGFNIKDTYMYW VRQAPGQGLEWMGRIDPAND NTKYAQKFQGRVTITADTST STAYMELSSLRSEDTAVYYC ARAKNLLNYFDYWGCGTLVT VSSAKTTPKLGGDIQMTQSP SSLSASVGDRVTITCRASQE ISGYLSWLQQKPGKCPKRLI YATSTLQSGVPSRFSGSRSG TDYTLTISSLQPEDFATYYC |
| | | LQYAIYPLTFGQGTKLEIKR GGGGS |
| 44 | $V_H$ (G44C) | CAGGTTCAGCTGGTGCAGTC TGGGGCAGAGGTTAAGAAGC CAGGGGCCTCAGTCAAGGTG TCCTGCAAGGCTTCTGGCTT CAACATTAAAGACACCTATA TGTACTGGGTGAGGCAGGCA CCTGGACAGTGCCTGGAGTG GATGGGAAGGATTGATCCTG CCAATGATAATACTAAATAT GCCCAGAAGTTCCAGGGCAG GGTCACTATAACAGCAGACA CATCCACCAGCACAGCCTAC ATGGAGCTCTCCAGTCTGAG ATCTGAGGACACTGCCGTCT ATTACTGTGCTAGAGCCAAG AATTT GTTAAATTACTTTGACTACT GGGGCCAAGGCACCCTTGTC ACAGTCTCCTCA |
| 45 | $V_L$ (Q100C) | GACATCCAGATGACCCAGTC TCCATCCTCCTTATCTGCCT CTGTGGGAGATAGAGTCACT ATCACTTGTCGGGCAAGTCA GGAAATTAGTGGTTACTTAA GCTGGCTTCAGCAGAAACCA GGTAAGGCTCCTAAACGCCT GATCTACGCCACATCCACTT TACAGTCTGGTGTCCCAAGT AGGTTCAGTGGCAGTAGGTC TGGGACAGATTATACTCTCA CCATCAGCAGCCTTCAGCCT GAAGATTTTGCAACCTATTA CTGTCTACAATATGCTATTT ATCCTCTCACCTTCGGTTGT GGGACCAAGCTGGAGATCAA ACGG |
| 46 | Linker | GCGAAAACCACCCCGAAACT GGGCGGG |
| 47 | Signal sequence | ATGGACCCCAAGGGCAGCCT GAGCTGGAGAATCCTGCTGT TCCTGAGCCTGGCCTTCGAG CTGAGCTACGGC |
| 48 | $V_H$ (G44C) -Linker- $V_L$ (Q100C) | CAGGTTCAGCTGGTGCAGTC TGGGGCAGAGGTTAAGAAGC CAGGGGCCTCAGTCAAGGTG TCCTGCAAGGCTTCTGGCTT CAACATTAAAGACACCTATA TGTACTGGGTGAGGCAGGCA CCTGGACAGTGCCTGGAGTG GATGGGAAGGATTGATCCTG CCAATGATAATACTAAATAT GCCCAGAAGTTCCAGGGCAG GGTCACTATAACAGCAGACA CATCCACCAGCACAGCCTAC ATGGAGCTCTCCAGTCTGAG ATCTGAGGACACTGCCGTCT ATTACTGTGCTAGAGCCAAG AATTTGTTAAATTACTTTGA CTACTGGGGCCAAGGCACCC TTGTCACAGTCTCCTCAGCC AAAACCACCCCGAAACTGGG CGGCGACATCCAGATGACCC AGTCTCCATCCTCCTTATCT GCCTCTGTGGGAGATAGAGT CACTATCACTTGTCGGGCAA GTCAGGAAATTAGTGGTTAC |

SEQUENCE TABLE

| SEQ ID NO | Description | Sequences |
|---|---|---|
| | | TTAAGCTGGCTTCAGCAGAA ACCAGGTAAGGCTCCTAAAC GCCTGATCTACGCCACATCC ACTTTACAGTCTGGTGTCCC AAGTAGGTTCAGTGGCAGTA GGTCTGGGACAGATTATACT CTCACCATCAGCAGCCTTCA GCCTGAAGATTTTGCAACCT ATTACTGTCTACAATATGCT ATTTATCCTCTCACCTTCGG TTGTGGGACCAAGCTGGAGA TCAAACGG |
| 49 | $V_H$ (G44C) -Linker- $V_L$ (Q100C) | CAGGTTCAGCTGGTGCAGTC TGGGGCAGAGGTTAAGAAGC CAGGGGCCTCAGTCAAGGTG TCCTGCAAGGCTTCTGGCTT CAACATT AAAGACACCTATATGTACTG GGTGAGGCAGGCACCTGGAC AGTGCCTGGAGTGGATGGGA AGGATTGATCCTGCCAATGA TAATACTAAATATGCCCAGA AGTTCCAGGGCAGGGTCACT ATAACAGCAGACACATCCAC CAGCACAGCCTACATGGAGC TCTCCAGTCTGAGATCTGAG GACACTGCCGTCTATTACTG TGCTAGAGCCAAGAATTTGT TAAAATTACTTTGACTACTGG GGCCAAGGCACCCTTGTCAC AGTCTCCTCAGCGAAAACCA CCCCGAAACTGGGCGGCGAC ATCCAGATGACCCAGTCTCC ATCCTCCTTATCTGCCTCTG TGGGAGATAGAGTCACTATC ACTTGTCGGGCAAGTCAGGA AATTAGTGGTTACTTAAGCT GGCTTCAGCAGAAACCAGGT AAGGCTCCTAAACGCCTGAT CTACGCCACATCCACTTTAC AGTCTGGTGTCCCAAGTAGG TTCAGTGGCAGTAGGTCTGG GACAGATTATACTCTCACCA TCAGCAGCCTTCAGCCTGAA GATTTTGCAACCTATTACTG TCTACAATATGCTATTTATC CTCTCACCTTCGGTTGTGGG ACCAAGCTGGAGATCAAACG GGGAGGTGGTGGGTCT |
| 50 | SS-$V_H$ (G44C) -Linker- $V_L$ (Q100C) | <u>ATGGACCCCAAGGGCAGCCT GAGCTGGAGAATCCTGCTGT TCCTGAGCCTGGCCTTCGAG CTGAGCTACGGCCAGGTTCA</u> GCTGGTGCAGTCTGGGGCAG AGGTTAAGAAGCCAGGGGCC TCAGTCAAGGTGTCCTGCAA GGCTTCTGGCTTCAACATTA AAGACACCTATATGTACTGG GTGAGGCAGGCACCTGGACA GTGCCTGGAGTGGATGGGAA GGATTGATCCTGCCAATGAT AATACTAAATATGCCCAGAA GTTCCAGGGCAGGGTCACTA TAACAGCAGACACATCCACC AGCACAGCCTACATGGAGCT CTCCAGTCTGAGATCTGAGG ACACTGCCGTCTATTACTGT GCTAGAGCCAAGAATTTGTT AAAATTACTTTGACTACTGGG GCCAAGGCACCCTTGTCACA GTCTCCTCAGCGAAAACCAC |
| 51 | SS-$V_H$ (G44C) -Linker- $V_L$ (Q100C) | CCCGAAACTGGGCGGCGACA TCCAGATGACCCAGTCTCCA TCCTCCTTATCTGCCTCTGT GGGAGATAGAGTCACTATCA CTTGTCGGGCAAGTCAGGAA ATTAGTGGTTACTTAAGCTG GCTTCAGCAGAAACCAGGTA AGGCTCCTAAACGCCTGATC TACGCCACATCCACTTTACA GTCTGGTGTCCCAAGTAGGT TCAGTGGCAGTAGGTCTGGG ACAGATTATACTCTCACCAT CAGCAGCCTTCAGCCTGAAG ATTTTGCAACCTATTACTGT CTACAATATGCTATTTATCC TCTCACCTTCGGTTGTGGGA CCAAGCTGGAGATCAAACGG <u>ATGGACCCCAAGGGCAGCCT GAGCTGGAGAATCCTGGTGT TCCTGAGCCTGGCCTTCGAG CTGAGCTACGGCCAGGTTCA</u> GCTGGTGCAGTCTGGGGCAG AGGTTAAGAAGCCAGGGGCC TCAGTCAAGGTGTCCTGCAA GGCTTCTGGCTTCAACATTA AAGACACCTATATGTACTGG GTGAGGCAGGCACCTGGACA GTGCCTGGAGTGGATGGGAA GGATTGATCCTGCCAATGAT AATACTAAATATGCCCAGAA GTTCCAGGGCAGGGTCACTA TAACAGCAGACACATCCACC AGCACAGCCTACATGGAGCT CTCCAGTCTGAGATCTGAGG ACACTGCCGTCTATTACTGT GCTAGAGCCAAGAATTTGTT AAAATTACTTTGACTACTGGG GCCAAGGCACCCTTGTCACA GTCTCCTCAGCGAAAACCAC CCCGAAACTGGGCGGCGACA TCCAGATGACCCAGTCTCCA TCCTCCTTATCTGCCTCTGT GGGAGATAGAGTCACTATCA CTTGTCGGGCAAGTCAGGAA ATTAGTGGTTACTTAAGCTG GCTTCAGCAGAAACCAGGTA AGGCTCCTAAACGCCTGATC TACGCCACATCCACTTTACA GTCTGGTGTCCCAAGTAGGT TCAGTGGCAGTAGGTCTGGG ACAGATTATACTCTCACCAT CAGCAGCCTTCAGCCTGAAG ATTTTGCAACCTATTACTGT CTACAATATGCTATTTATCC TCTCACCTTCGGTTGTGGGA CCAAGCTGGAGATCAAACGG GGAGGTGGTGGGTCT |
| 52 | F-$V_H$ | AAGCTTGCCACCATGGACCC CAAGGGCAGCCTG |
| 53 | R-$V_H$ (overlap) | GTTTCGGGGTGGTTTTCGCT GAGGAGACTGTGACAAG |
| 54 | F-$V_L$ (overlap) | CCACCCCGAAACTGGGCGGC GACATCCAGATGACCCAG |
| 55 | R-$V_L$ | GAATTCTTATCAATGGTGAT GGTG |
| 56 | linker | GGGGS |

The invention claimed is:

1. An isolated anti-PD-L1 diabody comprising a first polypeptide and a second polypeptide, wherein the first polypeptide comprises a first heavy chain variable region ($V_{H-1}$) and a first light chain variable region ($V_{L-1}$), and wherein the second polypeptide comprises a second heavy chain variable region ($V_{H-2}$) and a second light chain variable region ($V_{L-2}$), and wherein:
   a) the $V_{H-1}$ and the $V_{H-2}$ each comprises an HC-CDR1 comprising the amino acid sequence of SEQ ID NO: 1, an HC-CDR2 comprising the amino acid sequence of SEQ ID NO: 6, and an HC-CDR3 comprising the amino acid sequence of SEQ ID NO: 11; and
   b) the $V_{L-1}$ and the $V_{L-2}$ each comprises an LC-CDR1 comprising the amino acid sequence of SEQ ID NO: 14, an LC-CDR2 comprising the amino acid sequence of SEQ ID NO: 17, and an LC-CDR3 comprising the amino acid sequence of SEQ ID NO: 20.

2. An isolated anti-PD-L1 diabody comprising a first polypeptide and a second polypeptide, wherein the first polypeptide comprises a first heavy chain variable region ($V_{H-1}$) and a first light chain variable region ($V_{L-1}$), and wherein the second polypeptide comprises a second heavy chain variable region ($V_{H-2}$) and a second light chain variable region ($V_{L-2}$), and wherein:
   a) the $V_{H-1}$ and the $V_{H-2}$ each comprises a HC-CDR1, a HC-CDR2, and a HC-CDR3, respectively comprising the amino acid sequences of a CDR1, a CDR2, and a CDR3 within a heavy chain variable region ($V_H$) having the sequence set forth in any of SEQ ID NOs: 22-24; and
   b) the $V_{L-1}$ and the $V_{L-2}$ each comprises a LC-CDR1, LC-CDR2, and a LC-CDR3, respectively comprising the amino acid sequences of a CDR1, a CDR2, and a CDR3 within a light chain variable region ($V_L$) having the sequence set forth in any of SEQ ID NOs: 25-27.

3. The diabody of claim 1, wherein the first polypeptide and the second polypeptide are linked via a covalent bond.

4. The diabody of claim 3, wherein the covalent bond comprises a disulfide bond.

5. The diabody of claim 4, wherein the disulfide bond is formed by a) a cysteine residue in a HC-FR2 of the first polypeptide and a cysteine residue in a LC-FR4 of the second polypeptide, and b) a cysteine residue in a LC-FR4 of the first polypeptide and a cysteine residue in a HC-FR2 of the second polypeptide.

6. The diabody of claim 1, wherein:
   a) the $V_{H-1}$ in the first polypeptide and the $V_{H-2}$ in the second polypeptide comprises a G44C mutation or a Q105C mutation according to the Kabat numbering system; and/or
   b) the $V_{L-1}$ in the first polypeptide and the $V_{L-2}$ in the second polypeptide comprises a Q100C mutation or an A43C mutation according to the Kabat numbering system.

7. The diabody of claim 1, wherein the $V_{H-1}$ and the $V_{L-1}$ of the first polypeptide and the $V_{H-2}$ and the $V_{L-2}$ of the second polypeptide are fused to each other via a peptide linker.

8. The diabody of claim 1, wherein the $V_{H-1}$ and $V_{H-2}$ comprises the amino acid sequence of any one of SEQ ID NOs: 22-24, and the $V_{L-1}$ and $V_{L-2}$ comprises the amino acid sequence of any one of SEQ ID NOs: 25-27.

9. The diabody of claim 1, wherein the first polypeptide and the second polypeptide comprises the amino acid sequence of any one of SEQ ID NOs: 36-43.

10. A pharmaceutical composition comprising the diabody of claim 1, and a pharmaceutical acceptable carrier.

11. A polynucleotide encoding the diabody of claim 1.

12. A nucleic acid construct, comprising the polynucleotide of claim 11.

13. A vector comprising the nucleic acid construct of claim 12.

14. An isolated host cell comprising the polynucleotide according to claim 11.

15. A culture medium comprising the diabody of claim 1.

16. A method of producing an anti-PD-L1 diabody, comprising:
   a) culturing the isolated host cell of claim 14 under conditions effective to express the diabody; and
   b) obtaining the expressed diabody from the host cell.

17. A method of determining the distribution of PD-L1 in an individual, comprising:
   a) administering to the individual an imaging agent comprising the diabody of claim 1 labeled with a radionuclide; and
   b) imaging the imaging agent in the individual with a non-invasive imaging technique.

18. A method of diagnosing an individual having a PD-L1 associated disease or condition, comprising:
   determining the distribution of PD-L1 in the individual using the method of claim 17,
   wherein the individual is positive for PD-L1 if signal of the imaging agent is detected at a tissue of interest, or the individual is negative for PD-L1 if signal of the imaging agent is not detected at a tissue of interest.

19. A method of treating an individual having a PD-L1 associated disease or condition, comprising:
   a) diagnosing the individual using the method of claim 18; and
   b) administering to the individual an effective amount of a therapeutic agent targeting PD-L1, if the individual is positive for PD-L1.

20. A method of treating an individual having a disease or condition, comprising administering to the individual an effective amount of the diabody of claim 1.

21. An imaging agent comprising the diabody of claim 1 labeled with a radionuclide.

22. A method of preparing an imaging agent targeting PD-L1, comprising:
   a) conjugating a chelating compound to the diabody of claim 1 to provide an anti-PD-L1 diabody conjugate; and
   b) contacting a radionuclide with the anti-PD-L1 diabody conjugate, thereby providing the imaging agent.

23. A method of determining the distribution of PD-L1 in an individual, comprising:
   (a) administering to the individual an effective amount of a diabody agent comprising the diabody of claim 1 and a first conjugation moiety;
   (b) subsequently administering to the individual an effective amount of a radionuclide compound comprising a radionuclide and a second conjugation moiety, wherein the first conjugation moiety and the second conjugation moiety is conjugated to each other in vivo to provide an imaging agent; and
   (c) imaging the imaging agent in the individual with a non-invasive imaging technique.

24. The diabody of claim 8, wherein:
   a) the $V_{H-1}$ and $V_{H-2}$ comprises the amino acid sequence of SEQ ID NO: 22, and the $V_{L-1}$ and $V_{L-2}$ comprises the amino acid sequence of SEQ ID NO: 25;

b) the $V_{H-1}$ and $V_{H-2}$ comprises the amino acid sequence of SEQ ID NO: 23, and the $V_{L-1}$ and $V_{L-2}$ comprises the amino acid sequence of SEQ ID NO: 26; or
c) the $V_{H-1}$ and $V_{H-2}$ comprises the amino acid sequence of SEQ ID NO: 24, and the $V_{L-1}$ and $V_{L-2}$ comprises the amino acid sequence of SEQ ID NO: 27.

* * * * *